(12) United States Patent
Shin et al.

(10) Patent No.: US 8,809,012 B2
(45) Date of Patent: Aug. 19, 2014

(54) LABELING AGENT AND METHODS FOR SIMULTANEOUS SEQUENCING AND QUANTIFICATION OF MULTIPLE PEPTIDES AND PROTEINS USING THE SAME

(75) Inventors: Seung Koo Shin, Gyeongsangbuk-do (KR); Hye Joo Yoon, Gyeongsangbuk-do (KR); Yong Sik Jung, Daejeon (KR); Hee Yoon Lee, Daejeon (KR); Min Soo Suh, Gyeongsangbuk-do (KR); Jong Cheol Seo, Seoul (KR)

(73) Assignee: Postach Academy-Industry Foundation, Gyeongsangbuk-do (KR)

( * ) Notice: Subject to any disclaimer, the term of this patent is extended or adjusted under 35 U.S.C. 154(b) by 0 days.

(21) Appl. No.: 13/818,489

(22) PCT Filed: Aug. 23, 2011

(86) PCT No.: PCT/KR2011/006225
§ 371 (c)(1),
(2), (4) Date: Apr. 1, 2013

(87) PCT Pub. No.: WO2012/026743
PCT Pub. Date: Mar. 1, 2012

(65) Prior Publication Data
US 2013/0183704 A1    Jul. 18, 2013

(30) Foreign Application Priority Data

Aug. 23, 2010  (KR) .................. 10-2010-0081659
Oct. 14, 2010  (KR) .................. 10-2010-0100538

(51) Int. Cl.
*C12Q 1/37* (2006.01)
*C07C 237/12* (2006.01)
*C07C 237/20* (2006.01)

(52) U.S. Cl.
CPC ............. *C07C 237/12* (2013.01); *C07C 237/20* (2013.01)
USPC ........................................................... 435/23

(58) Field of Classification Search
CPC ........................... C07C 237/12; C07C 237/20
See application file for complete search history.

(56) References Cited

U.S. PATENT DOCUMENTS

| 5,432,267 A | 7/1995 | Kusama et al. |
| 2005/0148087 A1 | 7/2005 | Pappin et al. |
| 2006/0148093 A1 | 7/2006 | Gygi et al. |

FOREIGN PATENT DOCUMENTS

| KR | 10-2010-0009466 A | 1/2010 |
| KR | 10-2010-0009479 A | 1/2010 |
| WO | WO 95/09634 A1 | 4/1995 |
| WO | WO 97/27331 | 7/1997 |
| WO | WO 2005/068446 | 7/2005 |
| WO | WO 2010/008159 | 1/2010 |

OTHER PUBLICATIONS

Galemmo, Jr., Robert A. et al. "(N-acryl-N-alkyl)glycyl Borolysine Analogs: a new class of potent thrombin inhibitors." Bioorganic & Medicinal Chemistry Letters 1996, vol. 6(24), pp. 2913-2918.

*Primary Examiner* — Marcela M Cordero Garcia
*Assistant Examiner* — Sergio Coffa
(74) *Attorney, Agent, or Firm* — Brinks Gilson & Lione

(57) ABSTRACT

The present invention provides a compound that can utilize hydrogen isotope and, at the same time, can quantify multiplexed samples at one time, as well as decreasing the cost for synthesis of the labeling agent. In addition, the present invention provides a novel method for quantitatively analyzing protein and peptide analytes having different quantities form each other using the labeling agent, wherein y-type fragment ions having a high mass which comprises the analyte remained after coupling the labeling agent with the analyte and then removing a part of the labeling agent through tandem mass spectrometry are utilized to conduct the quantitative analysis.

11 Claims, 52 Drawing Sheets

(a)

(b) tag α

X₁–X₄: H/D (c) tag β

(d) tag γ

(e) tag δ

TMS acetylene: trimethylsilylacetylene
THF: tertrahydrofuran
TBSCl: tert-butyldimethylsilyl chloride
EtOAc: ethyl acetate
TBAF: tetra-n-butylammonium fluoride
MsCl: methanesulfonyl chloride
DCM: dichloromethane
DMF: *N,N*-dimethylformamide a)
Activation b)
Coupling Reaction Isotope-coded groups $R_A/R_C$ or $R_B/R_C$ ized using Matrix-Assisted Laser Desorption/Ionization (MALDI) or Electrospray Ionization (ESI) and then subjected to mass analysis to accurately measure the mass thereof and be compared with the peptide information provided by the genetic sequences to reveal the identity of proteins. More specifically, some peptide ions were selected and decomposed by collision in the mass spectrometer to obtain the sequences of peptides from fragment ions, thereby revealing the identity of proteins.

LABELING AGENT AND METHODS FOR SIMULTANEOUS SEQUENCING AND QUANTIFICATION OF MULTIPLE PEPTIDES AND PROTEINS USING THE SAME

This application is a National Stage of International Application of PCT/KR2011/006225 filed Aug. 23, 2011, which claims the benefit of the filing date of Korean Patent Application No. 10-2010-0081659, filed Aug. 23, 2010 and of Korean Patent Application No. 10-2010-0100538, filed Oct. 14, 2010. The entirety of these applications is hereby incorporated by reference.

TECHNICAL FIELD

The present invention relates to a labeling agent and methods for simultaneous sequencing and quantification of multiple peptides and proteins using the same. More specifically, the present invention relates to a labeling agent capable of displaying a strong quantitation signal and methods for simultaneous sequencing and quantification of multiple peptides and proteins using the same.

BACKGROUND ART

Mass spectrometry has been widely used for the identification and quantitative analysis of proteins and peptides. For example, peptides produced from the enzymatic digestion of proteins were ionized using Matrix-Assisted Laser Desorption/Ionization (MALDI) or Electrospray Ionization (ESI) and then subjected to mass analysis to accurately measure the mass thereof and be compared with the peptide information provided by the genetic sequences to reveal the identity of proteins. More specifically, some peptide ions were selected and decomposed by collision in the mass spectrometer to obtain the sequences of peptides from fragment ions, thereby revealing the identity of proteins.

For the quantitative analysis of proteins and peptides, the method of labeling proteins and peptides to be analyzed with chemical labels comprising stable isotopes has been widely used to analyze the mass. When the same kinds of chemical labels with different isotopes were attached to the same kinds of many protein and peptide samples for quantitative comparison and subjected to mass analysis, the masses of each of the samples are different on the mass spectrum or tandem mass spectrum due to the difference in the masses of isotopes so that they cannot be analyzed simultaneously.

To simultaneously conduct the identification and quantitative analysis of proteins and peptides, chemical labeling with isobars has been employed. In US Patent Publication No. US 2005/0148087 and International Patent Publication No. WO 2005/068446 and the like, isobaric chemical labels have been disclosed designed to display quantitation signals on tandem mass spectrum through attaching to peptides and collision and decomposition. However, because the labeling agents presented in said references use isotopes such as carbon-13, nitrogen-15, or oxygen-18, etc., there are problems that the synthesis of various isobars is limited and the price is too high. Further, the quantitative analysis using isobaric labeling agents disclosed in the prior art cannot be employed in quadrupole ion trap mass spectrometer such as Paul trap, linear ion trap, etc. Thus, there is a need to provide a new isobaric labeling agent that can simultaneously identify the peptide sequence and the protein quantity using various hydrogen isotopes which can substitute for hydrogen and have a relatively low price.

Meanwhile, quadrupole ion trap mass spectrometers have been widely used to reveal the identity of proteins and peptides since they are cheaper, easy to maintain and manage, and convenient to use as compared with other mass spectrometers. They also have an ability to conduct tandem mass spectrometry several times by collecting ions in the gas phase. For this reason, quadrupole ion trap mass spectrometers have been most widely provided and managed in the field of proteome study. As a general summary, tandem mass spectrometry using such quadrupole ion traps generally consists of a technology called Resonant Excitation Collision-Induced Dissociation (RE-CID). In such a case, when the mass-to-charge ratio of fragment ions is less than about ⅓rd of the mass-to-charge ratio of parent ions, ions are not stably collected in the ion trap and thus cannot be detected. It is referred to as the 'low-mass cutoff' effect. The isobaric labeling agents employed in the prior technology use small fragment ions having the mass of about 100-200 Da as a quantitation signal and thus have the problem that they are not detected as a quantitation signal ion in quadrupole ion trap mass spectrometers due to the low-mass cutoff effect. Furthermore, accurate quantitative analysis may not be possible, since in the mass region of 100-200 Da there is a very great possibility that the internal fragment ions having small mass, which can be derived from the analyte proteins or peptides, interfere with the quantitation signal ions.

Thus, the materials disclosed in the above-mentioned patents can be used only for analysis of fragment ions having small mass and therefore have a critical limitation in that they cannot be used in quadrupole ion trap mass spectrometers. For this reason, the invention relating to the isobaric labels that can be used in most widely distributed quadrupole ion trap mass spectrometers without any limitation and the analytical methods using the same is needed. In addition, in order to overcome said limit the quantitation signal needs to be displayed as the fragment ions having a sufficiently high mass. Since the fragment ions having high mass have a very low possibility that they are disturbed by noise signal, as compared to the fragment ions having low mass, and are not restricted by the low-mass cutoff, which can be caused in quadrupole ion trap mass spectrometers, they have high applicable value.

Meanwhile, in Korean Patent Application No. 2008-0070272 the present inventors have disclosed the new isobaric labeling agents named Mass-balanced isotope tag (MBIT) that uses only hydrogen isotope, can control the mass of quantitation signal, and has a dipeptide structure. In addition, Korean Published Patent No. 2010-0009466, Korean Patent Publication No. 2010-0009479, and International Patent Publication No. WO 10/008,159 have proposed a mass-variable labeling agent and a set of mass-variable labeling agents, wherein the mass controlling group is modified to diversify the properties and quantitation signal mass of the isobaric labeling agents, and further provided the multiplexed quantitative analytical method using the same, that is, the multi 2-plex quantitative method, which is a simultaneous, multiplexed quantitative analytical method for three or more samples using two or more kinds of the labeling agents. Although by utilizing said method the isobaric labeling agents can be easily and inexpensively synthesized, and further, multiplexed samples can also be quantified, when the multiplexed quantification is accomplished according to the multi 2-plex quantitative method, the drawbacks are that too much of the standard samples are consumed and the total quantity of the samples to be analyzed at a time is also increased.

Thus, the present inventors have researched a labeling agent that utilizes hydrogen isotope and, at the same time, can quantify multiplexed samples at the same time as well as decreasing the cost for synthesis of the labeling agent. As a result, we have identified that such purposes can be achieved through a new chemical structure, thereby completing the present invention. In addition, even in cases where the multiplexed samples are analyzed, we have identified that such a new chemical structure can improve the shortcomings of the prior art in that the quantitative intensity is weakened and the quantitative accuracy is lowered, to strongly provide the quantitation signal in the tandem mass spectrometer, thereby completing the present invention. Further, the present inventors have studied the analytical method that can also be applied to the quadrupole ion trap mass spectrometer using the isobaric labeling agent provided by the present inventors, and then, identified the method wherein the analysis can be conducted via the quantitation signal ion having a high mass, and further identified a method that can quantify the relative quantity of peptides and proteins in all kinds of mass spectrometers including quadrupole ion trap mass spectrometer using this technology. Thereby, the present invention is finally completed.

DISCLOSURE OF INVENTION

Technical Problem

The purpose of the present invention is to provide a novel chemical compound that utilizes hydrogen isotope and, at the same time, can quantify multiplexed samples simultaneously as well as decreasing the cost for synthesis of the labeling agent.

Another purpose of the present invention is to provide a composition comprising two or more kinds of said compounds.

Further, the purpose of the present invention is to provide a novel quantitative analytical method that enables simultaneous quantitative analysis of two or more kinds of the analytes using said compound or said composition.

Still another purpose of the present invention is to provide a quantitative analytical method via a quantitative analytical signal which can be detected at a mass value higher than the analyte using the isobaric mass-variable labeling agent comprising hydrogen isotope and for simultaneous multiplexed quantitative analysis of two or more peptide sequences and proteins.

Technical Solution

To solve said technical problem, the present invention provides a compound represented by the following chemical formula 1:

[Chemical Formula 1]

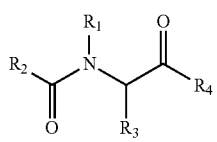

wherein,
$R_1$ is $C_{1-10}$ alkyl or

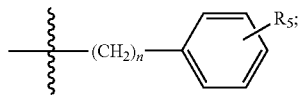

$R_2$ is $C_{1-10}$ alkyl or

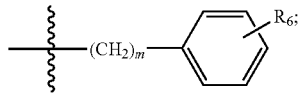

$R_3$ is a side chain of amino acid residue;
$R_4$ is hydroxy or a reactive linker;
$R_5$ is hydrogen, $C_{1-4}$ alkyl or $C_{2-4}$ alkynyl;
$R_6$ is hydrogen, $C_{1-4}$ alkyl or $C_{2-4}$ alkynyl;
n and m are independently of each other an integer of 1 to 4; and
said $R_1$ and $R_2$ do not comprise deuterium or at least one of said $R_1$ and $R_2$ comprises deuterium.

Examples of the compound represented by above formula 1 are illustrated with reference to FIG. 1. As shown in FIG. 1, when the compound represented by above formula 1 is used for tandem mass spectrometry, it produces an ion displaying quantitation signal and, in particular, $R_1^+$ and $R_1$—$NH^+$=CH—$R_3$ turn to an ion displaying quantitation signal. According to one embodiment of the present invention, if benzyl group is substituted in $R_1$, it could be identified that $R_1^+$ displays a strong quantitation signal.

Preferably, the quantitation signal of the compound represented by above formula 1 is a 4-(1-propynyl)benzyl cation. When $R_1$ comprises deuterium, the quantitation signal can be varied. By way of example, the quantitation signal can be 129 Th($CH_3C{\equiv}CC_6H_4CH_2^+$), 131 Th($CH_3C{\equiv}CC_6H_4CD_2^+$) 132 Th($CD_3C{\equiv}CC_6H_4CH_2^+$) or 134 Th($CD_3C{\equiv}CC_6H_4CD_2^+$).

Preferably, in said formula 1
$R_1$ is $C_{6-9}$ alkyl or

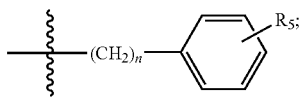

$R_2$ is $C_{6-9}$ alkyl or

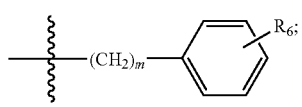

$R_5$ is hydrogen, propyl or prop-1-ynyl;
$R_6$ is hydrogen, propyl or prop-1-ynyl); and
n and m are independently of each other an integer of 1 to 4.

More preferably, in the above formula 1, $R_1$ is octyl; and $R_2$ is heptyl.

In addition, in the above formula 1, $R_1$ and $R_2$ are preferably the same, i.e. it is preferable that $R_1$ is $C_{1-10}$ alkyl and $R_2$ is $C_{1-10}$ alkyl; or $R_1$ is

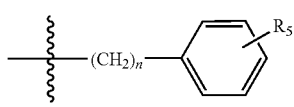

and $R_2$ is

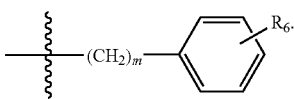

Further, it is preferable that said $R_1$ and $R_2$ are $CH_3C\equiv CC_6H_4CH_2$ and $CD_3C\equiv CC_6H_4CD_2CH_2$, respectively;

$CH_3C\equiv CC_6H_4CD_2$ and $CD_3C\equiv CC_6H_4CH_2CH_2$, respectively;

$CD_3C\equiv CC_6H_4CH_2$ and $CH_3C\equiv CC_6H_4CD_2CH_2$, respectively; or $CD_3C\equiv CC_6H_4CD_2$ and $CH_3C\equiv CC_6H_4CH_2CH_2$, respectively.

In the above formula 1, $R_3$ is a side chain of amino acid residue which is originated from the fact that the formula 1 has the structure substituted with $R_1$ and $R_2$ on amine group of amino acid.

As used in the present invention, the term "amino acid" denotes natural amino acids or artificial amino acids, preferably natural amino acids. For example, said amino acid denotes glycine, alanine, serine, valine, leucine, isoleucine, methionine, glutamine, asparagine, cysteine, histidine, phenylalanine, arginine, tyrosine or tryptophan.

In addition, as used in the present invention, the term "side chain of amino acid residue" denotes the remaining structure excluding $NH_2CH_2COOH$ from the structure of amino acid, i.e. the group substituted on $CH_2$ of $NH_2CH_2COOH$. For example, in the case of glycine the side chain of glycine residue denotes hydrogen; and in the case of serine the side chain of serine residue denotes hydroxymethyl. In the procedures for preparing the compound of said formula 1, said $R_3$ can be freely controlled depending on the kinds of amino acids, and according to this, the quantitation signal can also be adjusted.

In the above formula 1, $R_4$ is hydroxy or a reactive linker.

As used in the present invention, the term "a reactive linker" denotes a reactive group which can allow the compound of the above formula 1 to couple with the analyte. In the present invention, when the compound of the above formula 1 is used for analysis of proteins or peptides, the reactive groups able to react with the amine group or hydroxy group present in proteins or peptides are preferable. For example, the reactive groups can include, but are not limited to, succinimid-N-oxy, 3-sulfosuccinimid-N-oxy, benzotriazol-1-yloxy, pentahalobenzyloxy, 4-nitrophenoxy or 2-nitrophenoxy. Further, when $R_4$ is hydroxy, the above formula 1 totally represents the compounds having carboxy group and therefore said carboxy group can be converted into a carbonyl group substituted with the reactive linker.

Examples of preferable compounds among the compounds represented by the above formula 1 are as follows:

1) 2-(N-(4-(prop-1-ynyl)benzyl)-3-(4-(prop-1-ynyl)phenyl) propanamido)acetic acid;
2) 2-(N-(4-(prop-1-ynyl)benzyl)-3-(4-(prop-1-ynyl-3,3,3-$d_3$)phenyl)propanamido-3,3-$d_2$)acetic acid;
3) 2-(N-(4-(prop-1-ynyl)benzyl-1,1-$d_2$)-3-(4-(prop-1-ynyl-3,3,3-$d_3$)phenyl)propanamido)acetic acid;
4) 2-(N-(4-(prop-1-ynyl-3,3,3-$d_3$)benzyl)-3-(4-(prop-1-ynyl)phenyl)propanamido-3,3-$d_2$)acetic acid;
5) 2-(N-(4-(prop-1-ynyl-3,3,3-$d_3$)benzyl-1,1-$d_2$)-3-(4-(prop-1-ynyl)phenyl)propanamido)acetic acid;
6) 2-(N-(4-propylbenzyl)-2-(4-propylphenyl)acetamido) acetic acid;
7) 2-(5-phenyl-N-(3-phenylpropyl)pentanamido)acetic acid; and
8) 2-(N-octyloctanamido)acetic acid.

In addition, the present invention provides a composition comprising two or more kinds of the compounds represented by the above formula 1.

As used in the present invention, the term "two or more kinds" denotes that two or more kinds of the compounds having chemical structures different from each other are included. Preferably, two to four kinds of the compounds are included. More preferably, it is preferable to include two or more kinds of the compounds which have chemical structures which differ from each other only in relation to the substitution of deuterium and hydrogen.

Preferably, said two or more kinds of the compounds have the same number of deuterium as each other. Since their chemical structures are not identical to each other, but the number of deuterium is identical with one another, a difference in the masses of ions displaying the quantitation signals may arise to display the masses of each of samples at the positions different from each other on a mass spectrum or tandem mass spectrum thereby making it possible to quantitatively analyze the samples by comparing the relative abundance of the samples.

Examples of said compositions can include the compositions comprising at least one of the compounds selected from the group consisting of the followings:

1) 2-(N-(4-(prop-1-ynyl)benzyl)-3-(4-(prop-1-ynyl-3,3,3-$d_3$) phenyl)propanamido-3,3-$d_2$)acetic acid;
2) 2-(N-(4-(prop-1-ynyl)benzyl-1,1-$d_2$)-3-(4-(prop-1-ynyl-3,3,3-$d_3$)phenyl)propanamido)acetic acid;
3) 2-(N-(4-(prop-1-ynyl-3,3,3-$d_3$)benzyl)-3-(4-(prop-1-ynyl)phenyl)propanamido-3,3-$d_2$)acetic acid; and
4) 2-(N-(4-(prop-1-ynyl-3,3,3-$d_3$)benzyl-1,1-$d_2$)-3-(4-(prop-1-ynyl)phenyl)propanamido)acetic acid.

Further, the present invention provides a method for quantitatively analyzing the analyte using the compound represented by the above formula 1 or the composition comprising two or more kinds of the compounds represented by the above formula 1. To quantitatively analyze the analyte, said compounds should be coupled with the analyte, wherein the coupling of said compound to the analyte is accomplished by reacting the linker with amine group of the analyte while serving the linker as the leaving group to be separated.

Said analyte is characterized as being proteins, carbohydrates, or lipids. In addition, said analyte is characterized as being peptides. Further, said analyte is characterized as being nucleic acids or nucleic acid derivatives. In addition, said analyte is characterized as being steroids.

Further, the present invention provides an analytical method for simultaneous peptide sequencing and protein quantification which comprises the step of coupling the composition comprising two or more kinds of the compounds represented by the above formula 1 to the analyte; and the step of decomposing said analyte to quantify said analyte.

The decomposition method for said quantification is preferably tandem mass spectrometry. The quantitation signal providing said quantitation signal mass is $R_1^+$ or the internal fragment of $R_1NH^+=CHR_3$. As the preferable embodiment, the quantitation signal providing said quantitation signal mass is a 4-(1-propynyl)benzyl cation.

Preferably, the quantitation signal providing said quantitation signal mass is 129 Th($CH_3C\equiv CC_6H_4CH_2^+$), 131 Th($CH_3C\equiv CC_6H_4CD_2^+$), 132 Th($CD_3C\equiv CC_6H_4CH_2^+$) or 134 Th($CD_3C\equiv CC_6H_4CD_2^+$).

In addition, the present invention provides a method for preparing the compound represented by the above formula 1, wherein the specific method is illustrated with reference to FIGS. 3 to 5.

As shown in FIG. 3, the compound represented by the above formula 1 can be synthesized using a reporter unit in the form of haloalkane, a balance unit in the form of carboxylic acid, and an esterified amino acid.

In addition, the compound represented by the above formula 1 comprising deuterium can be prepared by introducing deuterium into the reporter unit and the balance unit and then using the deuterium-introduced units. As the method for introducing deuterium, any method known in the technical field to which the present invention belongs can be used. Specifically, the method shown in FIG. 2 can be used. The method for introducing one deuterium includes the method for substituting hydrogen of terminal alkyne in basic heavy water ($D_2O$) with deuterium, and the method for partially reducing one carbonyl group with sodium borodeuteride ($NaBD_4$) or aluminum lithium deuteride ($LiAlD_4$). The method for introducing two deuteriums includes the method for reducing alkene with deuterium gas ($D_2$) in the presence of a metal catalyst, the method for reducing carbonyl group of peptide bond or ester bond with $LiAlD_4$, and the method for introducing deuterium into the alpha position of the ester compound using sodium methoxide ($NaOCD_3$). Three deuteriums can be introduced through the method of alkylating secondary amine or terminal alkyne using iodomethane-$d_3$ ($CD_3I$). The method for introducing four deuteriums includes the method for reducing two carbonyl groups with $LiAlD_4$ and the method for reducing alkyne with $D_2$ in the presence of a metal catalyst. As one embodiment, the present invention synthesized the quadruple isobaric labeling agent (FIG. 1(b), tag a) by combining the method for introducing two deuteriums by reducing carbonyl group of ester bond with $LiAlD_4$, and the method for introducing three deuteriums by alkylating alkyne with $CD_3I$.

According to one embodiment of the present invention, the reporter unit is first synthesized, and a part of the synthesized reporter unit is modified through three-step additional reaction to synthesize the balance unit, wherein the specific methods for preparing the reporter unit and the balance unit are illustrated with reference to FIG. 4.

First, the method for synthesis of the reporter unit is as follows.

Trimethylsilyl (TMS)-protected alkyne is introduced into 4-bromobenzoic acid methyl ester via Sonogashira coupling using palladium catalyst and cuprous iodide. Then, the ester is reduced to the alcohol. In this case, when aluminum lithium hydride ($LiAlH_4$) or aluminum lithium deuteride ($LiAlD_4$) is used, the compound substituted with two hydrogens or deuteriums, is produced.

The resulting alcohol is protected with tert-butyldimethylsilane (TBS) by treating with tert-butyldimethylsilane chloride (TBSCl), and only alkyne-protecting TMS is selectively removed using potassium carbonate. Using iodomethane-$d_0$ ($CH_3I$) or -$d_3$ ($CD_3I$) methyl-$d_0$ or -$d_3$ is introduced into the terminal alkyne thus produced. Then, TBS is removed using tetra-n-butylammonium fluoride (TBAF).

The resulting compound is treated with methanesulfonic acid chloride, and substituted with iodine using sodium iodide to synthesize the reporter unit. During the reaction, a total of 4 kinds of the reporter units are obtained depending on the combinations of $LiAlH_4/LiAlD_4$ and $CH_3I/CD_3I$. When $LiAlH_4$ and $CH_3I$ are used, the reporter-$d_0$ having no deuterium is produced; when $LiAlD_4$ and $CH_3I$ are used, the reporter-$d_2$ comprising two deuteriums is produced; when $LiAlH_4$ and $CD_3I$ are used, the reporter-$d_3$ comprising three deuteriums is produced; and when $LiAlD_4$ and $CD_3I$ are used, the reporter-$d_5$ comprising five deuteriums is produced.

Next, the method for synthesis of the balance unit is as follows.

Diethyl malonate is alkylated using a part of the reporter unit as synthesized. After removing one carboxyl group of malonic acid through reflux, ethyl ester is hydrolyzed with aqueous sodium hydroxide solution to synthesize the balance unit. Since deuterium is not used in the course of modifying the reporter unit to the balance unit, the number of deuterium in the balance unit depends on the reporter unit as used.

The reporter unit and the balance unit as prepared above can be used to prepare the compound comprising deuterium as represented by the above formula 1, according to the method shown in FIG. 3, wherein the total number of deuteriums contained in the reporter unit and the balance unit is maintained. That is, for the case of quadruple isobaric labeling agent tag α as shown in FIG. 6, for example, when the reporter-$d_n$ is used, the balance unit (balance-$d_{5-n}$) comprising 5-n deuteriums is used to synthesize the isobar. Amine of glycine methyl ester is alkylated with the reporter-$d_n$ (n=0, 2, 3, and 5). The compound as synthesized and the balance-$d_{5-n}$ are combined using 1-ethyl-3-(3-dimethylaminopropyl) carbodiimide (EDC), 1-hydroxybenzotriazole (HOBt), and N,N-diisopropyl ethylamine (DIPEA), and then the methyl ester is hydrolyzed with aqueous sodium hydroxide solution to obtain the acid-form isobaric labeling agent tag $\alpha_{129+n}$ having 129+n as the mass value of the quantitation signal. In addition, according to the similar method as above, tag β can be prepared as shown in FIG. 5.

Further, the present invention provides the method for quantifying the analyte which comprises the step of coupling a labeling agent comprising a compound represented by the following formula 2 with the analyte (step 1); the step of ionizing and decomposing said coupled product to produce a fragment ion (step 2); and the step of quantifying the fragment ion comprising the analyte and $R_C$ among said fragment ions (step 3):

[Chemical Formula 2]

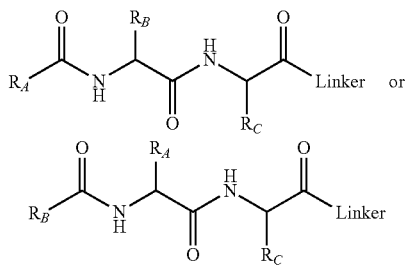

wherein, $R_A$ is a straight or branched $C_1$-$C_{18}$ alkyl, $R_B$ is a mass controlling group, $R_C$ is a straight or branched $C_1$-$C_{18}$ alkyl, Linker is a reactive linker to induce the coupling with the analyte, and $R_A$ and $R_C$ are the same alkyl, but at least one thereof contains one or more deuterium.

Said step 1 is a step of coupling the labeling agent represented by the above formula 2 with the analyte, wherein the coupling of the labeling agent with the analyte is for the subsequent quantitative analysis. Said coupling is to bind the labeling agent to the analyte through reaction of Linker of the labeling agent with amine group of the analyte. The coupling method is as disclosed in Korean Patent Publication Nos. 2010-0009466 and 2010-0009479, and International Patent Publication No. WO 10/008,159, and can be accomplished through the coupling reaction of amine group with Linker as known in the relevant technical field. When the analyte contains two or more amine groups, two or more of the labeling agent represented by the above formula 2 can be coupled.

As used in the present invention, the term "labeling agent" denotes the compounds represented by the above formula 2 as disclosed in Korean Patent Publication Nos. 2010-0009466 and 2010-0009479, and International Patent Publication No. WO 10/008,159, all of said patent publications are incorporated herein by reference.

Specifically, the term "Linker" as used in the present invention denotes an active ester which becomes the leaving group due to the nucleophilic attack of amine. Said amine is characterized as being a primary amine. In addition, said reactive linker can be selected from the group consisting of N-hydroxysuccinimidyl group, N-hydroxysulfosuccinimidyl group, benzotriazol-1-yloxy group, pentahalobenzyl group, 4-nitrophenyl group and 2-nitrophenyl group.

In addition, the term "mass controlling group ($R_B$)" denotes a group as introduced so that the quantitation signal is not overlapped with other fragments on the spectrum by controlling the mass of N-acylated amino acid fragment when being decomposed in the course of the quantitative analysis after coupling with the analyte. By changing the kinds of $R_B$, the mass of quantitation signal can be variously altered. Said mass controlling group can be one of the side chains of natural or artificial amino acid residues having similar or identical properties. In addition, said mass controlling group is characterized as having similar or identical properties. In addition, said mass controlling group can be a straight or branched $C_{1-18}$ alkyl, for example, straight or branched alkyls including methyl, ethyl, propyl, butyl, pentyl, hexyl, heptyl or octyl.

Said $R_A$ and $R_C$ are the same alkyl, wherein at least one thereof comprises deuterium, and play a role in enabling the quantitative analysis due to a difference in masses of isotopes. Preferably, it is characterized in that said $R_A$ and $R_C$ are methyl or methyl containing one or more deuterium, or each of said $R_A$ and $R_C$ is ethyl, and at least one of $R_A$ and $R_C$ comprises one or more deuterium. In addition, said $R_A$ and $R_C$ are alkyls having the same number of carbons, but have different numbers of deuterium as included. In this respect, it is preferable that said $R_A$ and $R_C$ are $CH_3$ and $CD_3$, or $CD_3$ and $CH_3$, respectively. That is, it is preferable that for $R_A$ and $R_C$ in said compounds $R_C$ is $CD_3$ when $R_A$ is $CH_3$, and $R_A$ is $CD_3$ when $R_C$ is $CH_3$. Alternatively, it is preferable that said $R_A$ and $R_C$ are $C_2H_5$ and $C_2D_5$, respectively, or $C_2D_5$ and $C_2H_5$, respectively. In other words, for $R_A$ and $R_C$ in the above compounds $R_C$ is $C_2D_5$ when $R_A$ is $C_2H_5$, and $R_A$ is $C_2D_5$ when $R_C$ is $C_2H_5$.

The above formula 2 is characterized as being a dipeptide labeled with an isotope, wherein N-terminal is acylated and the linker, which becomes a leaving group due to the nucleophilic attack of amine, is attached to C-terminal. In addition, said dipeptide is characterized as being a dipeptide labeled with deuterium.

The chemical structure and analytical theory of said "labeling agent" are illustrated with reference to FIGS. 13 to 15.

FIG. 13 schematically shows the chemical structure of the labeling agent. The compound disclosed in Korean Patent Publication Nos. 2010-0009466 and 2010-0009479, and International Patent Publication No. WO 10/008,159 was designated as "MBIT" which has the structure of dipeptide of which N-terminal is acylated and C-terminal has the linker as attached, without wishing to theoretically limit thereto.

FIG. 14 schematically shows the coupling pattern of MBIT material in peptides and proteins, without wishing to theoretically limit thereto. The coupling can also be accomplished with the primary amine of lysine side chain as well as with the primary amine of the N-terminal in peptides and proteins. Therefore, when the labeling agent is coupled with one peptide or protein, two or more labeling agents can be multiply coupled depending on the number of lysine included in protein and peptide. Although the analyte may not be necessarily proteins or peptides, the same number of the labeling agents as the number of primary or secondary amines included in the analyte can be maximally coupled with the analyte.

Particularly, in the present invention, it is preferable that two or more kinds of the compounds represented by the above formula 2 having the uniform number of total deuterium included in $R_A$ and $R_C$, preferably said two kinds of the compounds in the form of a set is used. When the compound pairs forming said set are designated as being the first compound and the second compound, it is preferable that said first compound and second compound have the same mass controlling group ($R_B$). In addition, in the compound pairs, when one of $R_A$ and $R_C$ of the first compound comprises many deuteriums as compared to the other, it is preferable that the second compound have $R_C$ of the first compound as $R_A$, and $R_A$ of the first compound as R. For example, in the compound pairs, when $R_A$ and $R_C$ of the first compound is $CH_3$ and $CD_3$, respectively, $R_A$ and $R_C$ of the second compound can be $CD_3$ and $CH_3$, respectively. Alternatively, in the compound pairs, when $R_A$ and $R_C$ of the first compound is $C_2H_5$ and $C_2D_5$, respectively, $R_A$ and $R_C$ of the second compound can be $C_2D_5$ and $C_2H_5$, respectively. Particularly, for quantification using $y_S$ ion in the present invention it is preferable that only $R_C$ of one of the first and second compounds comprises deuterium.

When the analyte each discriminately labeled with the first and second compounds of said set of labeling agents is analyzed by means of tandem mass spectrometry, in cases where the labeling agent is decomposed to separate $R_A$ and $R_C$, the fragment ions produced through decomposition exhibits a difference as much as a difference in masses of deuterium in $R_A$ and $R_C$, and the result thereof is displayed on the spectrum of tandem mass spectrometry. By comparing the relative intensities thereof, the relative quantity of the analyte can be quantified. In general, each of the two complementary fragment ions different from each other as separated and produced in the course of tandem mass spectrometry can be generally utilized as the independent quantitation signal.

As used in the present invention, the term "analyte" denotes the materials to be analyzed with the labeling agent according to the present invent ion. Said analytes can be proteins, carbohydrates, lipids, peptides, nucleic acids or nucleic acid derivatives, or steroids.

Said step 2 is the step of ionizing and decomposing said coupled product to produce a fragment ion, wherein the fragment ions are produced by breaking the amide bond present in the coupled product.

As the fragment ions that can be produced by breaking the amide bond of the coupled product of the present invention, the fragment ion comprising $R_A$ and $R_B$, and the fragment ion comprising $R_C$ and the analyte can be produced. In the present invention, the fragment ion comprising $R_A$ and $R_B$ is designated as the '$b_S$ ion', and the fragment ion comprising $R_C$ and the analyte is designated as '$y_S$ ion'. It will be illustrated with reference to FIGS. 15 and 16.

FIG. 15 is a diagram showing the fragment ions produced when the coupled product is decomposed in the course of tandem mass spectrometry. In this case, a pair of MBIT reagents having the same molecular formula but different regions labeled with deuterium is classified into $^H$MBIT and $^L$MBIT, wherein MBIT reagent labeled on $R_A$ or $R_B$ with deuterium calls $^H$MBIT, and MBIT reagent labeled on $R_C$ with deuterium calls $^L$MBIT. The total weight of the analyte coupled with $^H$MBIT is identical to that coupled with $^L$MBIT.

Two isotope encoding groups were selected, the one comprising deuterium and the other not comprising deuterium were marked H and L, respectively, as the superscripts on the left top. As depicted in FIG. 15, in general, the coupled product can be separated into the fragment ion ($b_S$) comprising $R_A$ and $R_B$, and the fragment ion ($y_S$) comprising $R_C$ and the analyte while breaking the amide bond between two amino acids of dipeptide in the course of tandem mass spectrometry. The fragment ion produced by removing only the portion corresponding to the formula 2 from the analyte is designated as "–tag".

FIG. 16 depicts the spectrum of tandem mass spectrometry that can be theoretically developed when peptides coupled with two or more compounds of formula 2 are analyzed with tandem mass spectrometry. As shown in FIG. 16, when two or more amine groups including amino acids on N-terminal and C-terminal of peptides are coupled with the compound of formula 2, the masses of all b- and y-type sequence ions that can be produced from peptides have the smaller mass value as compared to the mass of –tag. Therefore, $y_S$ ion having the mass higher than that of –tag is displayed in the range of the masses which are not disturbed by other fragment ions theoretically derived from peptides. When proteins are enzymatically digested with trypsin or LysC as most widely used proteolytic enzymes, peptides comprising lysine on C-terminal can be obtained, and thus, two compounds of formula 2 can be coupled with amine group on N-terminal and amine group of C-terminal lysine side chain.

Said step 3 is the step of quantifying the fragment ion ($y_S$) comprising the analyte and $R_C$ among said fragment ions, i.e. the step of analyzing the analyte as the fragment ions having a high mass.

Since the mass value of $y_S$ quantitation signal is at least ⅓ of the mass value of parent ions, $y_S$ ions can be detected regardless of the low-mass cutoff even in case of tandem mass spectrometry using the resonant excitation collision-induced dissociation in an ion trap mass spectrometer. Therefore, contrary to other isobaric labels using the quantitation signals having low mass values in the prior art, the present invention is characterized in that the quantitative analysis using $y_S$ quantitation signals can also be conducted even in a quadrupole ion trap mass spectrometer.

According to one embodiment of the present invention by said analytical method, it can be identified that the quantitative analysis as $y_S$ fragment ions having a high mass value is possible using the compound of formula 2. Particularly, since the fragment ions having a mass higher than that of the analyte itself is used, even in a quadrupole ion trap mass spectrometer the quantitative analysis is possible and the signal intensity is also amplified. Thus, according to the present invention, the more effective analysis as compared to the analysis using the compound of formula 2 in the prior art can be made.

Advantageous Effects

The present invention provides a novel compound that comprises hydrogen isotope, can display a strong intensity of the quantitation signal, and can quantitatively analyze two or more proteins at the same time, and a composition comprising two or more kinds of said compounds. Further, the present invention can provide an analytical method for simultaneously analyzing the peptides sequence and quantifying the quantity of proteins using said labeling agent or composition.

In addition, the present invention can provide a new method for simultaneously analyzing the amino acid sequence of peptides and quantifying the quantity of peptides using the isobaric labeling agent. In case of other isobaric labeling agents used in the prior art, the labeling agent is coupled with the analyte and the bond present in the middle of the labeling agent is then decomposed by tandem mass spectrometry and the fragment ions having a low mass but not comprising the analyte are used to conduct the quantitative analysis. On the contrary, the present invention is characterized by the fact that the isobaric labeling agent according to the present invention is used to decompose the coupling of the labeling agent in the course of tandem mass spectrometry, and then the fragment ions ($y_S$) having a high mass value and comprising the analyte among the fragment ions thus produced can be used to conduct the quantitative analysis. According to this, the present invention can accomplish the quantitative analysis with strong signal intensity maximally 5 times or more the prior case where the quantitation signal ions having low mass value are used and quantify the relative quantities of peptides and proteins in all kinds of mass spectrometers including a quadrupole ion trap mass spectrometer.

BRIEF DESCRIPTION OF DRAWINGS

FIG. 1(a) shows the representative structure of the compound according to the present invention, and the structure of quantitation signals produced from said compound. FIGS. 1(b) to 1(e) show four structures of the compound according to one example of the present invention. FIG. 1(b) is the structure synthesized as the multiplexed isobar using hydrogen isotope, wherein each of $X_1$-$X_4$ shows the position selectively substituted with hydrogen isotope.

FIG. 8 shows the tandem mass spectra of the model peptide (DRVYIHPF) coupled with the compound according to one example of the present invention.

FIG. 10(a) shows the result obtained from the sample comprising peptides labeled with the multiplexed isobar as mixed at a ratio of 2:1:2:1 (tag $\alpha_{129}$:$\alpha_{131}$:$\alpha_{132}$:$\alpha_{134}$), and FIG. 10(b) shows the result from the sample comprising peptides as mixed at a ratio of 1:2:1:2 (tag $\alpha_{129}$:$\alpha_{131}$:$\alpha_{132}$:$\alpha_{134}$).

FIG. 12(a) shows the intensity of parent ions observed by MALDI mass spectrometer with time at which each of peptides is eluted by LC, and FIG. 12(b) shows the comparison of the quantity of quantitation signals measured in each of peptides with the quantity of quantitation signal of tag $\alpha_{129}$. It is the result obtained from 6 kinds of peptides (FGER, VASLR, QEPER, AWSVAR, SEIAHR and YLYEIAR) in tryptic BSA labeled with the isobar.

FIG. 23(c) shows the intensity ratio of $b_S$ quantitation signal displayed when parent ion having +1 charge of the model peptide LISFYAGR labeled with the labeling agent according to one example of the present invention is produced by MALDI ionization and then subjected to tandem mass spectrometry in TOF/TOF apparatus.

BEST MODE FOR CARRYING OUT THE INVENTION

Hereinafter, the compounds according to the present invention and the analytical methods for simultaneous peptides sequencing and protein quantification using the same are specifically illustrated with reference to Examples and drawings as attached. However, the present invention is not limited the following descriptions, and can be embodied in various different forms by a person having an ordinary knowledge in the relevant technical field within the scope which does not deviate the technical concept of the present invention.

Example 1

Figure 1:
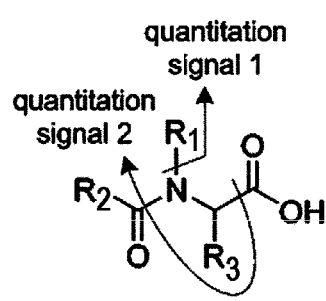
FIG. 1 shows the structure of the compound according to the present invention.
Figure 1:
Figure 1:
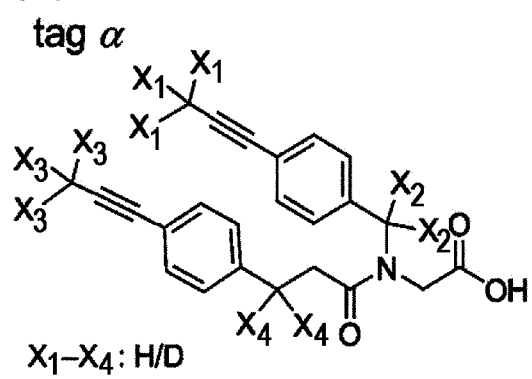
Figure 1:
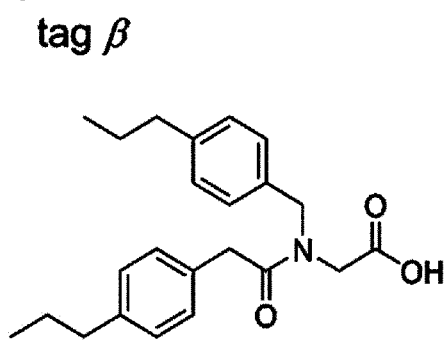
Figure 1:
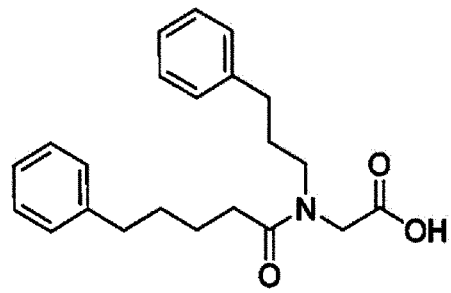
Figure 1:
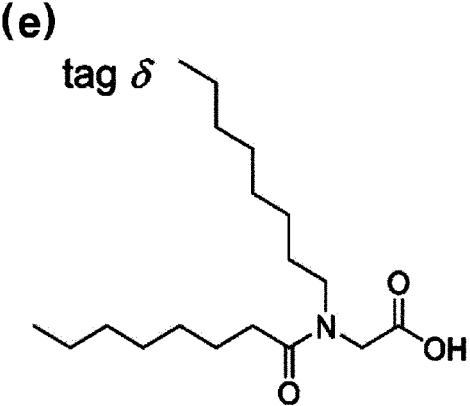
Figure 2:
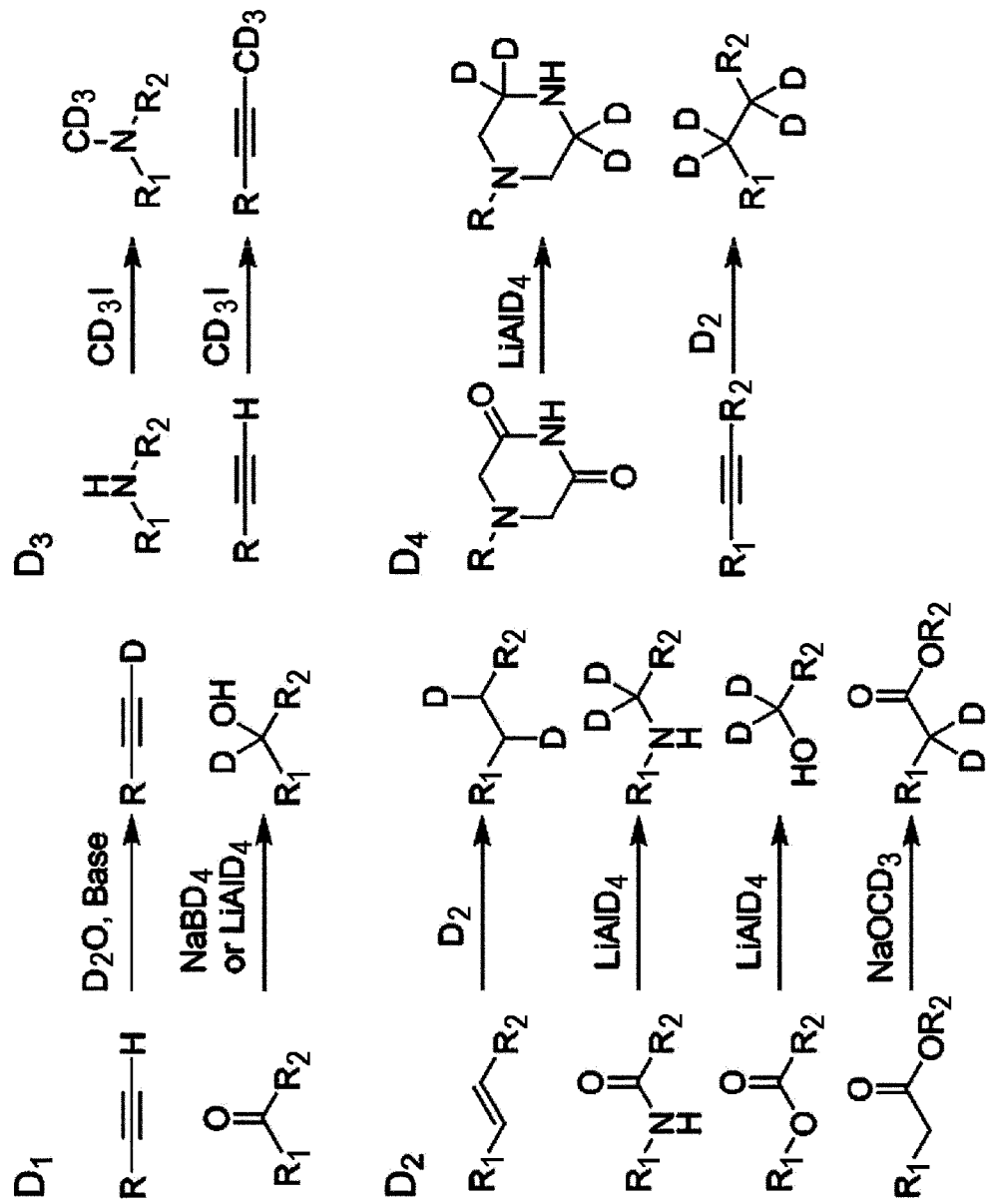
FIG. 2 shows the representative deuterium addition and substitution reaction, which can be utilized for preparing the compound according to the present invention as the isobaric labeling agent using hydrogen isotope.

In the compound (labeling agent) represented by FIG. 1(a), various structures or functional groups can be introduced into the positions of R$_1$, R$_2$, and R$_3$. In the present invention, as shown in FIG. 1(b) to FIG. 1(e) by way of examples, the compounds (tag α-δ) having four kinds of the structures were synthesized and then the quantitation signals depending on each of structures or functional groups were identified.

Of said four kinds of the structures, FIG. 1(b) is the example of synthesis of the isobaric labeling agent able to quantify the multiplexed protein using hydrogen isotope. In FIG. 1(b), X$_1$ to X$_4$ represent the positions of deuterium as substituted.

Example 1-1

Synthesis of Non-Isobaric Labeling Agent

Figure 3:
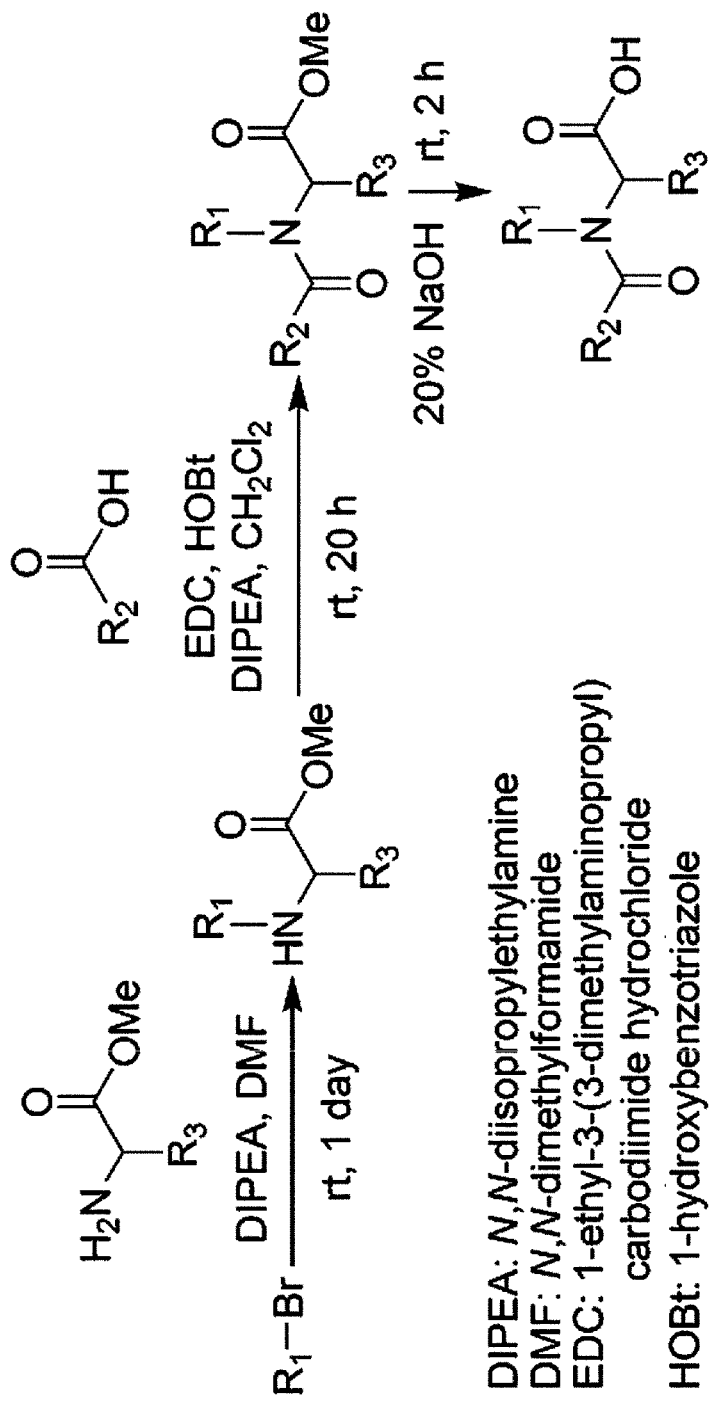
FIG. 3 shows the procedures for synthesis of the compound of the present invention. Said compound is synthesized using the reporter unit ($R_1$—Br) in the form of haloalkane, and the balance unit ($R_2$—COOH) in the form of a carboxylic acid, and esterified amino acid.
Figure 4:
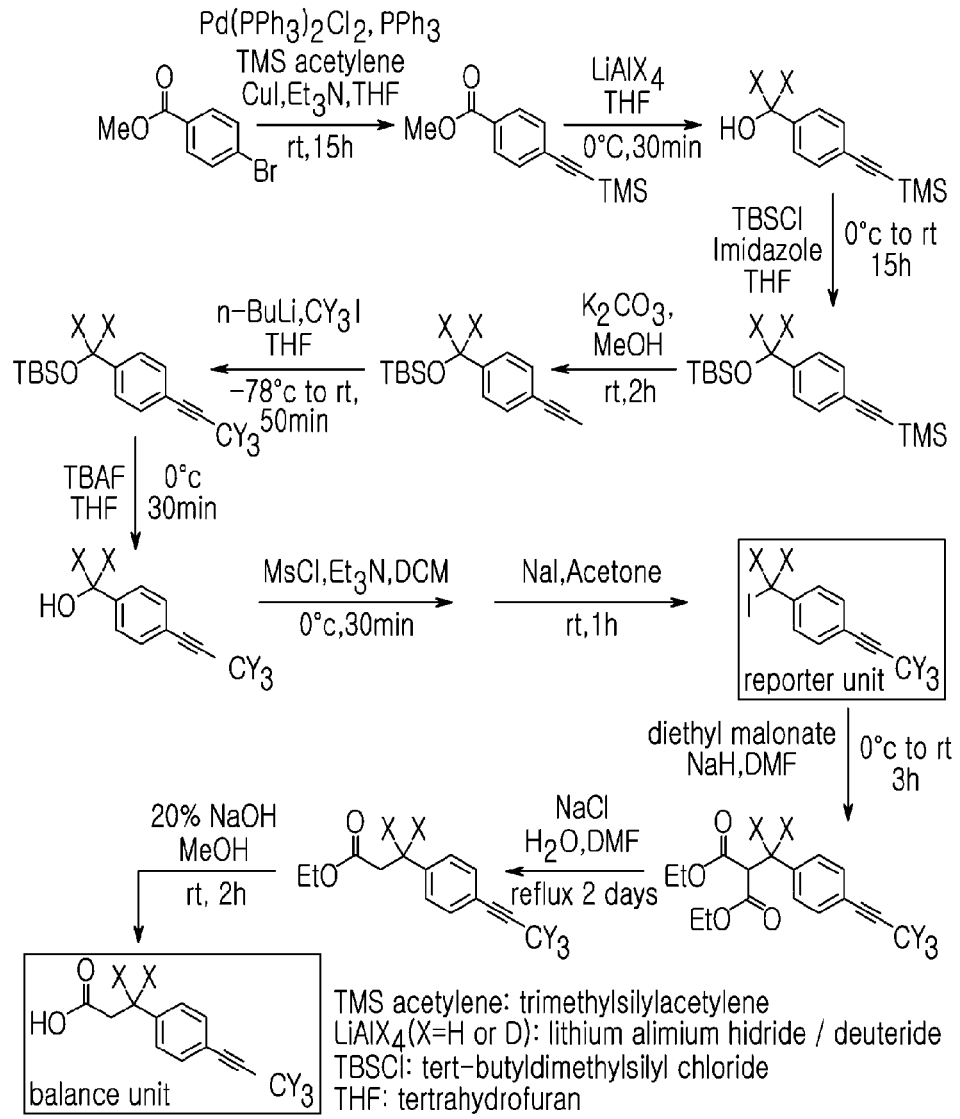
FIG. 4 shows the procedures for synthesis of the reporter unit and the balance unit required for synthesis of the compound (tag a) according to one example of the present invention, using deuterium addition and substitution reaction. The balance unit is synthesized through modification of the reporter unit. Two kinds of deuterium introducing methods (method for introducing two deuteriums by reducing carbonyl group of ester bond with $LiAlD_4$, and method for introducing three deuteriums by alkylating alkyne with $CD_3I$) are combined to synthesize 4 kinds of the reporter and balance units.
Figure 5:
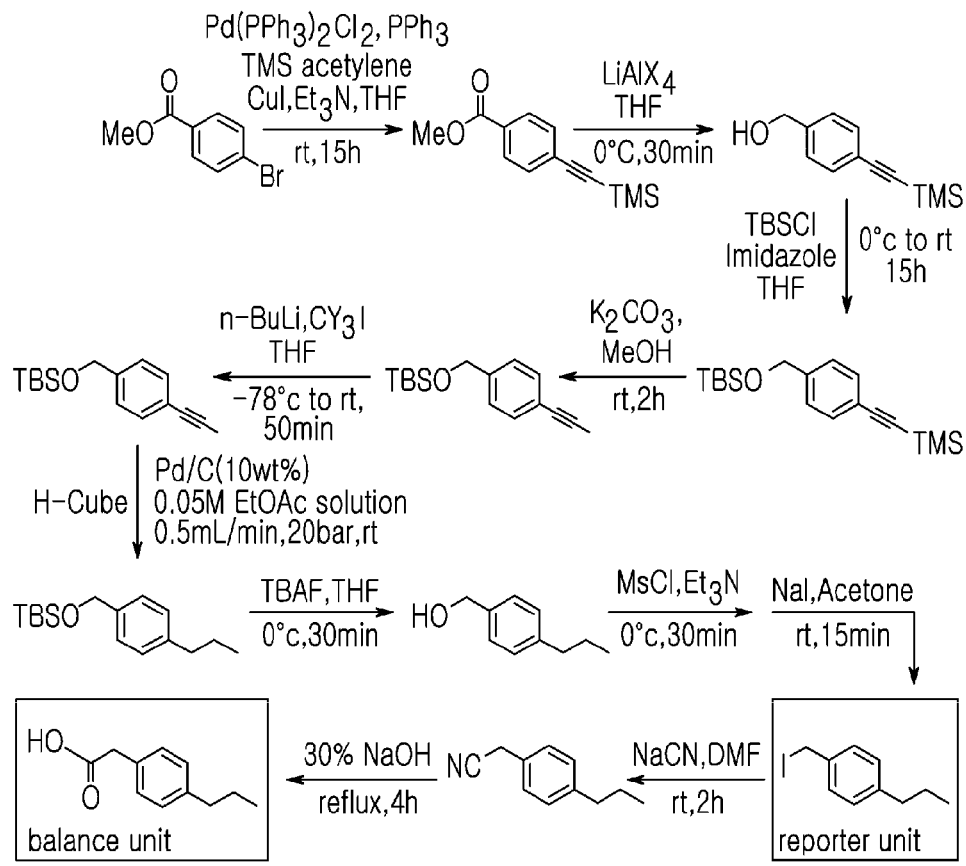
FIG. 5 shows the procedures for synthesis of the reporter unit and the balance unit required for synthesis of the compound (tag I) according to one example of the present invention. The balance unit is synthesized through modification of the reporter unit.
Figure 6:
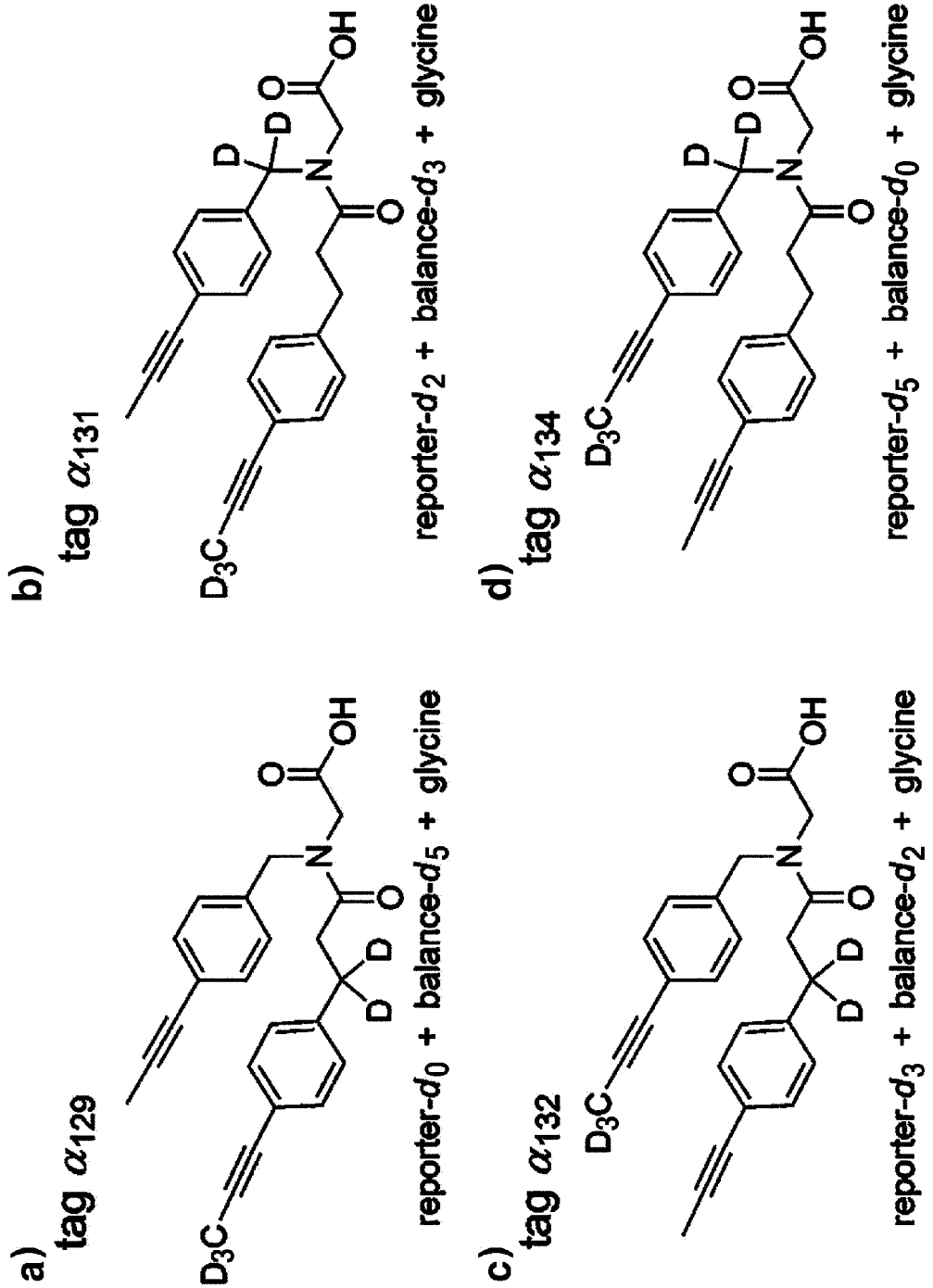
FIG. 6 shows the structures of the compounds according to one example of the present invention. They are synthesized using reporter-$d_n$ comprising n deuterium, balance-$d_{5-n}$ comprising 5-n deuterium, and glycine, wherein tag $\alpha_m$ denotes tag $\alpha$ having the mass value m of quantitation signal.

The labeling agent was synthesized in the order as shown in FIG. 3. In the non-isobaric labeling agent, reporter unit and balance unit of tag γ and tag δ (reporter unit of γ, 3-iodopropylbenzene; reporter unit of δ, 1-iodooctane; balance unit of γ, 5-phenylpentanoic acid; and balance unit of δ, octanoic acid) were purchased to synthesize each of the labeling agents; and for tag β the reporter unit (1-(iodomethyl)-4-propylbenzene) and the balance unit (2-(4-propylphenyl)acetic acid) constituting the labeling agent were synthesized according to the procedures of FIG. 5, and then used to synthesize tag β.

Synthesis of Tag β

First, procedures for synthesis of the reporter unit and the results of nuclear magnetic resonance (NMR) of the compounds produced from respective steps are shown in the following steps 1 to 8.

Step 1: Synthesis of 4-((trimethylsilyl)ethynyl)benzoic acid methyl ester

Under argon condition, 4-bromobenzoic acid methyl ester (500 mg, 2.33 mmol), bis(triphenylphosphine)palladium dichloride (Pd(PPh$_3$)$_2$Cl$_2$; 86.1 mg, 0.116 mmol), triphenylphosphine (PPh$_3$; 18.3 mg, 0.0698 mmol), trimethylsilyl acetylene (TMS acetylene; 493 µL, 3.49 mmol), and triethylamine (Et$_3$N; 486 µL, 3.49 mmol) were dissolved in 10 mL of well-dried tetrahydrofuran (dry THF) and stirred for 20 minutes at room temperature. To this was added again cuprous iodide (CuI; 8.86 mg, 0.0465 mmol) and the reaction mixture was stirred for 15 hours at room temperature. Upon completion of the reaction, the solvent was removed by distillation under reduced pressure, and 20 mL of n-pentane was added to the residue. The mixture was filtered through celite pad to remove the precipitate. The resulting solution was concentrated by distillation under reduced pressure and purified by column chromatography to obtain 503 mg (2.16 mmol, 93%) of the desired compound.

$^1$H NMR (300 MHz, CDCl$_3$): d 7.93 (dd, 2H, J=6.8 Hz, J=1.7 Hz), 7.48 (dd, 2H, J=6.7 Hz, J=1.8 Hz), 3.88 (s, 3H), 0.22 (s, 9H).

Step 2: Synthesis of (4-((trimethylsilyl)ethynyl)phenyl)methanol

Under argon condition, 4-((trimethylsilyl)ethynyl)benzoic acid methyl ester (316 mg, 1.36 mmol) was dissolved in 5 mL of dry THF and then cooled to 0° C. and LiAlH$_4$ (2.04 mL, 1.0 M solution in THF, 2.04 mmol) was slowly added thereto. Upon completion of the reaction after stirring for 30 minutes at 0° C., the reaction was terminated by adding 77 µL of water, 154 µL of 10% aqueous sodium hydroxide solution and 231 µL of water in order. When the white viscous precipitate was produced, the mixture was filtered through silica pad to remove the precipitate. The resulting solution was concentrated by distillation under reduced pressure, and purified by column chromatography to obtain 258 mg (1.26 mmol, 93%) of the desired compound.

$^1$H NMR (300 MHz, CDCl$_3$): d 7.44 (d, 2H, J=8.2 Hz), 7.27 (d, 2H, J=8.1 Hz), 4.66 (s, 2H), 1.67 (br, 1H), 0.23 (s, 9H).

Step 3: Synthesis of tert-butyldimethyl((4-((trimethylsilyl)ethynyl)benzyl)oxy)silane Under argon condition, (4-((trimethylsilyl)ethynyl)phenyl) methanol (258 mg, 1.26 mmol) was dissolved in 5 mL of dry THF and then cooled to 0° C., and imidazole (103 mg, 1.52 mmol) and TBSCl (228 mg, 1.52 mmol) dissolved in 3 mL of dry THF were added thereto. Thereafter, the temperature was raised to room temperature, and the reaction mixture was stirred for 15 hours at room temperature. Upon completion of the reaction, the reaction was terminated by adding 10 mL of aqueous saturated ammonium chloride solution. The reaction mixture was extracted with ethyl acetate (10 mL×4), and the organic layer thus obtained was treated with anhydrous magnesium sulfate to remove water. The precipitate was filtered out and the resulting solution was concentrated by distillation under reduced pressure, and purified by column chromatography to obtain 383 mg (1.20 mmol, 95%) of the desired compound.

$^1$H NMR (300 MHz, CDCl$_3$): d 7.41 (d, 2H, J=8.2 Hz), 7.23 (d, 2H, J=8.1 Hz), 4.70 (s, 2H), 0.90 (s, 9H), 0.22 (s, 9H), 0.00 (s, 6H).

Step 4: Synthesis of tert-butyl((4-ethynylbenzyl)oxy)dimethylsilane

Under argon condition, tert-butyldimethyl((4-((trimethylsilyl)-ethynyl)benzyl)oxy)silane (383 mg, 2.40 mmol) and potassium carbonate (332 mg, 2.40 mmol) were dissolved in 4 mL of methanol, and then stirred for 2 hours at room temperature. Upon completion of the reaction, the reaction was terminated by adding 10 mL of aqueous saturated ammonium chloride solution. The reaction mixture was extracted with ethyl acetate (5 mL×4) and the organic layer thus obtained was treated with anhydrous magnesium sulfate to remove water. The precipitate was filtered out and the resulting solution was concentrated by distillation under reduced pressure, and purified by column chromatography to obtain 280 mg (1.14 mmol, 95%) of the desired compound.

$^1$H NMR (300 MHz, CDCl$_3$): d 7.44 (d, 2H, J=8.2 Hz), 7.25 (d, 2H, J=8.5 Hz), 4.72 (s, 2H), 3.02 (s, 1H), 0.92 (s, 9H), 0.01 (s, 6H).

Step 5: Synthesis of tert-butyldimethyl((4-(prop-1-yn-1-yl)benzyl)oxy)-silane

Under argon condition, tert-butyl((4-ethynylbenzyl)oxy)dimethyl-silane (247 mg, 1.00 mmol) was dissolved in 5 mL of dry THF, cooled to −78° C., and n-butyl lithium (805 μL, 2.49 M solution in n-hexane, 2.00 mmol) was slowly added thereto. After stirring for 20 minutes at −78° C., iodomethane (313 μL, 5.00 mmol) was added again thereto. Thereafter, the temperature was raised to room temperature and the reaction mixture was stirred for 30 minutes at room temperature. Upon completion of the reaction, the reaction was terminated by adding 10 mL of aqueous saturated ammonium chloride solution. The reaction mixture was extracted with ethyl acetate (5 mL×4) and the organic layer thus obtained was treated with anhydrous magnesium sulfate to remove water. The precipitate was filtered out, and the resulting solution was concentrated by distillation under reduced pressure, and purified by column chromatography to obtain 253 mg (0.971 mmol, 97%) of the desired compound.

$^1$H NMR (300 MHz, CDCl$_3$): d 7.35 (d, 2H, J=8.2 Hz), 7.22 (d, 2H, J=8.2 Hz), 4.70 (s, 2H), 2.03 (s, 3H), 0.93 (s, 9H), 0.07 (s, 6H).

Step 6: Synthesis of tert-butyldimethyl((4-propylbenzyl)oxy)silane tert-butyldimethyl((4-(prop-1-yn-1-yl)benzyl)oxy)silane (252 mg, 0.968 mmol) was dissolved in 20 mL of ethyl acetate, and then passed through H-Cube apparatus equipped with 10% Pd/C catridge under 20 bar of hydrogen pressure at a speed of 0.5 mL/min. The solution thus passed was concentrated by distillation under reduced pressure to obtain 251 mg (0.949 mmol, 98%) of the desired compound.

$^1$H NMR (300 MHz, CDCl$_3$): d 7.23 (d, 2H, J=8.1 Hz), 7.12 (d, 2H, J=8.1 Hz), 4.69 (s, 2H), 2.26 (t, 2H, J=7.4 Hz), 1.65-1.58 (m, 2H), 0.94-0.85 (m, 12H), 0.08 (s, 6H).

Step 7: Synthesis of (4-propylphenyl)methanol

Under argon condition, tert-butyldimethyl((4-propylbenzyl)oxy)-silane (275 mg, 1.04 mmol) was dissolved in 5 mL of dry THF, and then n-butylammonium fluoride (TBAF; 1.56 mL, 1.0 M solution in tetrahydrofuran, 1.56 mmol) were slowly added thereto, and the mixture was stirred for 30 minutes at 0° C. Upon completion of the reaction, the reaction was terminated by adding 5 mL of aqueous saturated ammonium chloride solution. The reaction mixture was extracted with ethyl acetate (5 mL×4) and the organic layer thus obtained was treated with anhydrous magnesium sulfate to remove water. The precipitate was filtered out and the resulting solution was concentrated by distillation under reduced pressure and purified by column chromatography to obtain 198 mg (0.838 mmol, 95%) of the desired compound.

$^1$H NMR (300 MHz, CDCl$_3$): d 7.25 (d, 2H, J=8.0 Hz), 7.18 (d, 2H, J=8.0 Hz), 4.57 (s, 2H), 2.97 (s, 1H), 2.62 (t, 2H, J=7.4 Hz), 1.74-1.62 (m, 2H), 0.99 (t, 3H, J=7.4 Hz).

Step 8: Synthesis of 1-(iodomethyl)-4-propylbenzene (4-propylphenyl)methanol (100 mg, 0.666 mmol) was dissolved in 3 mL of well-dried dichloromethane (DCM) under argon condition and then cooled to 0° C., and methanesulfonyl chloride (MsCl; 62.1 μL, 0.799 mmol) and triethylamine (Et$_3$N; 140 μL, 0.999 mmol) were added thereto. Upon completion of the reaction after stirring for 30 minutes at 0° C., the reaction was terminated by adding 5 mL of water. The reaction mixture was extracted with DCM (3 mL×3), and the organic layer thus obtained was treated with anhydrous magnesium sulfate to remove water. The precipitate was filtered out, and the resulting solution was concentrated by distillation under reduced pressure. The residue was dissolved again in 6 mL of acetone and then sodium iodide (NaI; 150 mg, 0.999 mmol) was added thereto. Upon completion of the reaction after stirring for 15 minutes at room temperature, the solvent was dried by distillation under reduced pressure. 10 mL of water was added to the residue and the mixture was extracted with ethyl acetate (5 mL×3). The organic layer thus obtained was treated with anhydrous magnesium sulfate to remove water. The precipitate was filtered out, and the resulting solution was concentrated by distillation under reduced pressure, and purified by column chromatography to obtain 157 mg (0.604 mmol, 90%) of the desired compound (tag β reporter unit).

$^1$H NMR (300 MHz, CDCl$_3$): d 7.27 (d, 2H, J=8.1 Hz), 7.08 (d, 2H, J=8.0 Hz), 4.44 (s, 2H), 2.53 (t, 2H, J=7.4 Hz), 1.67-1.54 (m, 2H), 0.92 (t, 3H, J=7.4 Hz)

The procedures for synthesis of the balance unit from the reporter unit of tag β as synthesized above and the NMR results of the compounds produced from respective steps are shown in the following steps 9 and 10.

Step 9: Synthesis of 2-(4-propylphenyl)acetonitrile

Under argon condition, 1-(iodomethyl)-4-propylbenzene (73.6 mg, 0.283 mmol) was dissolved in 1 mL of well-dried N,N-dimethylformamide (dry DMF) and then sodium cyanide (NaCN; 27.7 mg, 0.566 mmol) was added and the reaction mixture was stirred for 2 hours at room temperature.

Upon completion of the reaction, the reaction was terminated by adding 3 mL of water and the mixture was extracted with diethyl ether (3 mL×3). The organic layer thus obtained was treated with anhydrous magnesium sulfate to remove water. The precipitate was filtered out and the resulting solution was concentrated by distillation under reduced pressure and purified by column chromatography to obtain 41.0 mg (0.257 mmol, 91%) of the desired compound.

$^1$H NMR (300 MHz, CDCl$_3$): d 7.23-7.16 (m, 4H), 3.69 (s, 2H), 2.58 (t, 2H, J=7.3 Hz), 1.69-1.57 (m, 2H), 1.93 (t, 3H, J=7.3 Hz).

Step 10: Synthesis of 2-(4-propylphenyl)acetic acid 2-(4-propylphenyl)acetonitrile (41.0 mg, 0.257 mmol) was dissolved in 1 mL of 30% aqueous sodium hydroxide solution and stirred under reflux condition for 4 hours. Upon completion of the reaction, the reaction solution was acidified by adding 3 mL of 10% aqueous hydrogen chloride solution and extracted with diethyl ether (3 mL×3). The organic layer thus obtained was treated with anhydrous magnesium sulfate to remove water. The precipitate was filtered out and the resulting solution was concentrated by distillation under reduced pressure and purified by column chromatography to obtain 34.8 mg (0.195 mmol, 76%) of the desired compound (balance unit of tag β).

$^1$H NMR (300 MHz, CDCl$_3$): d 7.24-7.13 (m, 4H), 3.16 (s, 2H), 2.58 (t, 2H, J=7.3 Hz), 1.70-1.58 (m, 2H), 0.95 (t, 3H, J=7.4 Hz).

Using the reporter unit and the balance unit, tag β was synthesized according to the procedures as shown in FIG. 3. Specific synthetic procedures and the NMR results of the compounds synthesized from respective steps are shown in the following steps 11 to 13.

Step 11: Synthesis of methyl 2-((4-propylbenzyl)amino)acetate

Under argon condition, glycine methyl ether (448 mg, 3.57 mmol) was dissolved in 5 mL of dry DMF and then N,N-diisopropylethylamine (DIPEA; 777 μL, 4.46 mmol) and 1-(iodomethyl)-4-propylbenzene (232 mg, 0.892 mmol) were added. The reaction mixture was then stirred for one day at room temperature. Upon completion of the reaction, the reaction was terminated by adding 10 mL of water and the reaction mixture was extracted with diethyl ether (10 mL×4). The organic layer thus obtained was treated with anhydrous magnesium sulfate to remove water. The precipitate was filtered out and the resulting solution was concentrated by distillation under reduced pressure and purified by column chromatography to obtain 152 mg (0.687 mmol, 77%) of the desired compound.

$^1$H NMR (300 MHz, CDCl$_3$): d 7.20 (d, 2H, J=7.9 Hz), 7.10 (d, 2H, J=7.9 Hz), 3.73 (s, 2H), 3.68 (s, 3H), 3.38 (s, 2H), 2.54 (t, 2H, J=7.4 Hz), 1.94 (br, 1H), 1.67-1.54 (m, 2H), 0.91 (t, 3H, J=7.3 Hz).

Step 12: Synthesis of methyl 2-(N-(4-propylbenzyl)-2-(4-propylphenyl) acetamido)acetate Methyl 2-((4-propylbenzyl)amino)acetate (24.5 mg, 0.0983 mmol) and 2-(4-propylphenyl)acetic acid (17.5 mg, 0.0983 mmol) were dissolved in 1 mL of well-dried DCM under argon condition and then EDC (56.5 mg, 0.295 mmol), HOBt (39.8 mg, 0.295 mmol) and DIPEA (84.3 μL, 0.491 mmol) were added and the reaction mixture was stirred for 20 hours at room temperature. Upon completion of the reaction, the reaction was terminated by adding 3 mL of water, and the reaction mixture was extracted with DCM (3 mL×4). The organic layer thus obtained was treated with anhydrous magnesium sulfate to remove water. The precipitate was filtered out and the resulting solution was concentrated by distillation under reduced pressure and purified by column chromatography to obtain 31.1 mg (0.0789 mmol, 80%) of the desired compound.

Major isomer: $^1$H NMR (300 MHz, CDCl$_3$): d 7.24-7.10 (m, 6H), 6.96-6.94 (m, 2H), 4.55 (s, 2H), 4.20 (s, 2H), 3.80 (s, 2H), 3.69 (s, 3H), 2.57-2.51 (m, 4H), 1.67-1.54 (m, 4H), 1.94-1.88 (m, 6H). Minor isomer: $^1$H NMR (300 MHz, CDCl$_3$): d 7.24-7.10 (m, 6H), 6.96-6.94 (m, 2H), 4.62 (s, 2H), 3.90 (s, 2H), 3.67 (s, 2H), 3.61 (s, 3H), 2.57-2.51 (m, 4H), 1.67-1.54 (m, 4H), 1.94-1.88 (m, 6H).

Step 13: Synthesis of 2-(N-(4-propylbenzyl)-2-(4-propylphenyl)acetamido)-acetic acid Methyl 2-(N-(4-propylbenzyl)-2-(4-propylphenyl)acetamido)-acetate (30.0 mg, 0.0786 mmol) was dissolved in 0.5 mL of methanol, and then 100 μL of 20% aqueous sodium hydroxide solution was added, and the reaction mixture was stirred for 2 hours at room temperature. Upon completion of the reaction, the reaction solution was diluted with 2 mL of ethyl acetate and neutralized by adding 200 μL of 10% aqueous hydrogen chloride solution. After removing water with anhydrous magnesium sulfate and filtering out the precipitate, the resulting solution was concentrated by distillation under reduced pressure and purified by column chromatography to obtain 26.4 mg (0.0718 mmol, 91%) of the desired compound.

Major isomer: $^1$H NMR (300 MHz, CDCl$_3$): d 7.24-6.88 (m, 8H), 4.54 (s, 2H), 3.98 (s, 2H), 3.77 (s, 2H), 2.55-2.47 (m, 4H), 1.64-1.51 (m, 4H), 0.93-0.87 (m, 6H). Minor isomer: $^1$H NMR (300 MHz, CDCl$_3$): d 7.24-6.88 (m, 8H), 4.58 (s, 2H), 3.83 (s, 2H), 3.63 (s, 2H), 2.55-2.47 (m, 4H), 1.64-1.51 (m, 4H), 0.93-0.87 (m, 6H).

Synthesis of Tag γ

The synthesis of tag γ was conducted using the purchased reporter and balance units according to the procedures as shown in FIG. 3. Specific synthetic procedures and the NMR results of the compounds synthesized from respective steps are shown in the following steps 1 to 3.

Step 1: Synthesis of methyl 2-((3-phenylpropyl)amino)acetate

Under argon condition, glycine methyl ester (330 mg, 2.63 mmol) was dissolved in 3 mL of dry DMF and then DIPEA (573 μL, 3.29 mmol) and 1-bromo-3-phenylpropane (100 μL, 0.658 mmol) were added. The reaction mixture was then stirred for one day at room temperature. Upon completion of the reaction, the reaction was terminated by adding 5 mL of water, and the reaction mixture was extracted with diethyl ether (4 mL×4). The organic layer thus obtained was treated with anhydrous magnesium sulfate to remove water. The precipitate was filtered out and the resulting solution was concentrated by distillation under reduced pressure and purified by column chromatography to obtain 19.6 mg (0.0946 mmol, 14%) of the desired compound.

$^1$H NMR (300 MHz, CDCl$_3$): d 7.28-7.23 (m, 2H), 7.18-7.13 (m, 3H), 3.70 (s, 3H), 3.39 (s, 2H), 2.68-2.60 (m, 4H), 1.86-1.76 (m, 2H).

Step 2: Synthesis of methyl 2-(5-phenyl-N-(3-phenylpropyl)pentanamido)-acetate

Methyl 2-((3-phenylpropyl)amino)acetate (20.0 mg, 0.0965 mmol) and 5-phenylvaleric acid (22.0 mg, 0.116 mmol) were dissolved in 1 mL of well-dried DCM under argon condition, and EDC (55.5 mg, 0.289 mmol), HOBt (39.1 mg, 0.289 mmol) and DIPEA (82.7 μL, 0.482 mmol) were added and the reaction mixture was stirred for 20 hours at room temperature. Upon completion of the reaction, the reaction was terminated by adding 3 mL of water, and the reaction mixture was extracted with DCM (3 mL×4). The organic layer thus obtained was treated with anhydrous magnesium sulfate to remove water. The precipitate was filtered out and the resulting solution was concentrated by distillation under reduced pressure, and purified by column chromatography to obtain 34.2 mg (0.0931 mmol, 96%) of the desired compound.

Major isomer: $^1$H NMR (300 MHz, CDCl$_3$): d 7.31-7.23 (m, 4H), 7.21-7.14 (m, 6H), 4.01 (s, 2H), 3.69 (s, 3H), 3.30 (t, 2H, J=7.9 Hz), 2.62-2.56 (m, 4H), 2.24 (t, 2H, J=6.9 Hz), 1.90-1.85 (m, 2H), 1.68-1.59 (m, 4H). Minor isomer: $^1$H NMR (300 MHz, CDCl$_3$): d 7.31-7.23 (m, 4H), 7.21-7.14 (m, 6H), 3.95 (s, 2H), 3.72 (s, 3H), 3.42 (t, 2H, J=7.9 Hz), 2.62-2.56 (m, 4H), 2.18 (t, 2H, J=6.9 Hz), 1.90-1.85 (m, 2H), 1.68-1.59 (m, 4H).

Step 3: Synthesis of 2-(5-phenyl-N-(3-phenylpropyl)pentanamido)acetic acid

Methyl 2-(5-phenyl-N-(3-phenylpropyl)pentanamido)acetate (34.2 mg, 0.0931 mmol) was dissolved in 0.5 mL of methanol and then 100 μL of 20% aqueous sodium hydroxide solution was added. The reaction mixture was then stirred for 2 hours at room temperature. Upon completion of the reaction, the reaction solution was diluted with 3 mL of ethyl acetate and neutralized by adding 200 μL of 10% aqueous hydrogen chloride solution. After removing water with anhydrous magnesium sulfate and filtering out the precipitate, the resulting solution was concentrated by distillation under reduced pressure and purified by column chromatography to obtain 26.2 mg (0.0741 mmol, 80%) of the desired compound.

Major isomer: $^1$H NMR (300 MHz, CDCl$_3$): d 7.26-7.12 (m, 10H), 3.99 (s, 2H), 3.28 (t, 2H, J=7.7 Hz), 2.61-2.52 (m, 4H), 2.21 (t, 2H, J=6.5 Hz), 1.91-1.76 (m, 2H), 1.61-1.55 (m, 4H). Minor isomer: $^1$H NMR (300 MHz, CDCl$_3$): d 7.26-7.12 (m, 10H), 3.91 (s, 2H), 3.40 (t, 2H, J=7.3 Hz), 2.61-2.52 (m, 4H), 2.21 (t, 2H, J=6.5 Hz), 1.91-1.76 (m, 2H), 1.61-1.55 (m, 4H).

Synthesis of Tag δ

The synthesis of tag δ was conducted using the purchased reporter and balance units according to the procedures as shown in FIG. 3. Specific synthetic procedures and the NMR results of the compounds synthesized from respective steps are shown in the following steps 1 to 3.

Step 1: Synthesis of methyl 2-(octylamino)acetate

Under argon condition, glycine methyl ester (358 mg, 2.85 mmol) was dissolved in 2 mL of dry DMF, and then DIPEA (620 μL, 3.56 mmol) and 1-bromooctane (123 μL, 0.712 mmol) were added, and the reaction mixture was stirred for one day at room temperature. Upon completion of the reaction, the reaction was terminated by adding 5 mL of water, and the reaction mixture was extracted with diethyl ether (4 mL×4). The organic layer thus obtained was treated with anhydrous magnesium sulfate to remove water. The precipitate was filtered out and the resulting solution was concentrated by distillation under reduced pressure and purified by column chromatography to obtain 31.6 mg (0.157 mmol, 22%) of the desired compound.

$^1$H NMR (300 MHz, CDCl$_3$): d 3.68 (s, 3H), 3.36 (s, 2H), 2.54 (t, 2H, J=7.1 Hz), 1.77 (s, 1H), 1.47-1.40 (m, 2H), 1.24-1.22 (m, 10H), 0.83 (t, 3H, J=6.5 Hz)

Step 2: Synthesis of methyl 2-(N-octyloctanamido)acetate

Methyl 2-(octylamino)acetate (31.6 mg, 0.157 mmol) and n-octanoic acid (30.0 μL, 0.188 mmol) were dissolved in 1 mL of well-dried DCM under argon condition and EDC (90.3 mg, 0.471 mmol), HOBt (63.6 mg, 0.471 mmol) and DIPEA (135 μL, 0.785 mmol) were added. The reaction mixture was then stirred for 12 hours at room temperature. Upon completion of the reaction, the reaction was terminated by adding 5 mL of water and the reaction mixture was extracted with DCM (4 mL×4). The organic layer thus obtained was treated with anhydrous magnesium sulfate to remove water. The precipitate was filtered out and the resulting solution was concentrated by distillation under reduced pressure and purified by column chromatography to obtain 44.7 mg (0.136 mmol, 87%) of the desired compound.

Major isomer: $^1$H NMR (300 MHz, CDCl$_3$): d 4.00 (s, 2H), 3.68 (s, 3H), 3.28 (t, 2H, J=7.8 Hz), 2.32 (t, 2H, J=7.4 Hz), 1.64-1.43 (m, 4H), 1.25 (br, 19H), 0.86-0.82 (m, 6H). Minor isomer: $^1$H NMR (300 MHz, CDCl$_3$): d 3.98 (s, 2H), 3.72 (s, 3H), 3.32 (t, 2H, J=7.5 Hz), 2.15 (t, 2H, J=7.3 Hz), 1.64-1.43 (m, 4H), 1.25 (br, 19H), 0.86-0.82 (m, 6H).

Step 3: Synthesis of 2-(N-octyloctanamido)acetic acid

Methyl 2-(N-octyloctanamido)acetate (44.7 mg, 0.136 mmol) was dissolved in 0.5 mL of methanol and then 100 μL of 20% aqueous sodium hydroxide solution was added. The reaction mixture was then stirred for 2 hours at room temperature. Upon completion of the reaction, the reaction solution was diluted with 3 mL of ethyl acetate and then neutralized by adding 200 μL of 10% aqueous hydrogen chloride solution. After removing water with anhydrous magnesium sulfate and filtering out the precipitate, the resulting solution was concentrated by distillation under reduced pressure and purified by column chromatography to obtain 36.5 mg (0.116 mmol, 86%) of the desired compound.

Major isomer: $^1$H NMR (300 MHz, CDCl$_3$): d 4.01 (s, 2H), 3.30 (t, 2H, J=7.5 Hz), 2.24 (t, 2H, J=7.4 Hz), 1.64-1.54 (m, 4H), 1.26 (br, 18H), 0.87-0.83 (m, 6H). Minor isomer: $^1$H NMR (300 MHz, CDCl$_3$): d 3.97 (s, 2H), 3.32 (t, 2H, J=7.5 Hz), 2.19 (t, 2H, J=7.5 Hz), 1.64-1.54 (m, 4H), 1.26 (br, 18H), 0.87-0.83 (m, 6H).

Example 1-2

Synthesis of Multiplexed Isobaric Labeling Agent

First, the procedures for synthesis of reporter-d$_5$ and reporter-d$_0$ among 4 kinds of the reporter units and the NMR results of the compounds produced from respective steps are shown in the following steps 1 to 7.

Step 1: Synthesis of 4-((trimethylsilyl)ethynyl)benzoic acid methyl ester

Under argon condition, 4-bromobenzoic acid methyl ester (500 mg, 2.33 mmol), bis(triphenylphosphine)palladium dichloride (Pd(PPh$_3$)$_2$Cl$_2$; 86.1 mg, 0.116 mmol), triphenylphosphine (PPh₃; 18.3 mg, 0.0698 mmol), trimethylsilyl acetylene (TMS acetylene; 493 μL, 3.49 mmol), and triethylamine (Et₃N; 486 μL, 3.49 mmol) were dissolved in 10 mL of dry THF and the reaction mixture was stirred for 20 minutes at room temperature. To this cuprous iodide (CuI; 8.86 mg, 0.0465 mmol) was again added and the mixture was stirred for 15 hours at room temperature. Upon completion of the reaction, the solvent was removed by distillation under reduced pressure and then 20 mL of n-pentane was added to the residue. The mixture was filtered through celite pad to remove the precipitate. The resulting solution was concentrated by distillation under reduced pressure, and purified by column chromatography to obtain 503 mg (2.16 mmol, 93%) of the desired compound.

$^1$H NMR (300 MHz, CDCl₃): d 7.93 (dd, 2H, J=6.8 Hz, J=1.7 Hz), 7.48 (dd, 2H, J=6.7 Hz, J=1.8 Hz), 3.88 (s, 3H), 0.22 (s, 9H).

Step 2

1) Synthesis of (4-((trimethylsilyl)ethynyl)phenyl)methanol-d₂

Under argon condition, 4-((trimethylsilyl)ethynyl)benzoic acid methyl ester (1.00 g, 5.16 mmol) was dissolved in 20 mL of dry THF and then cooled to 0° C., and LiAlD₄ (217 mg, 5.16 mmol) was slowly added thereto. Upon completion of the reaction after stirring for 30 minutes at 0° C., the reaction was terminated by adding 220 μL of water, 440 μL of 10% aqueous sodium hydroxide solution, and 660 μL of water in order. When the white viscous precipitate was produced, the mixture was filtered through a silica pad to remove the precipitate. The resulting solution was concentrated by distillation under reduced pressure, and purified by column chromatography to obtain 788 mg (3.82 mmol, 89%) of the desired compound.

$^1$H NMR (300 MHz, CDCl₃): d 7.44 (d, 2H, J=8.2 Hz), 7.27 (d, 2H, J=8.1 Hz), 1.67 (br, 1H), 0.23 (s, 9H).

2) Synthesis of (4-((trimethylsilyl)ethynyl)phenyl)methanol

Under argon condition, 4-((trimethylsilyl)ethynyl)benzoic acid methyl ester (316 mg, 1.36 mmol) was dissolved in 5 mL of dry THF, and then cooled to 0° C., and LiAlH₄ (2.04 mL, 1.0 M solution in THF, 2.04 mmol) was slowly added thereto. Upon completion of the reaction after stirring for 30 minutes at 0° C., the reaction was terminated by adding 77 μL of water, 154 μL of 10% aqueous sodium hydroxide solution and then 231 μL of water. When the white viscous precipitate was produced, the mixture was filtered through a silica pad to remove the precipitate. The resulting solution was concentrated by distillation under reduced pressure, and purified by column chromatography to obtain 258 mg (1.26 mmol, 93%) of the desired compound.

$^1$H NMR (300 MHz, CDCl₃): d 7.44 (d, 2H, J=8.2 Hz), 7.27 (d, 2H, J=8.1 Hz), 4.66 (s, 2H), 1.67 (br, 1H), 0.23 (s, 9H).

Step 3

1) Synthesis of tert-butyldimethyl((4-((trimethylsilyl)ethynyl)-benzyl)oxy)silane-d₂

Under argon condition, (4-((trimethylsilyl)ethynyl)phenyl)-methanol-d₂ (600 mg, 2.94 mmol) was dissolved in 15 mL of dry THF, and then cooled to 0° C., and imidazole (240 mg, 3.52 mmol) and tert-butyldimethylsilane chloride (TBSCl; 531 mg, 3.52 mmol) dissolved in 5 mL of dry THF were added thereto. Then, the temperature was raised to room temperature and the reaction solution was stirred for 15 hours at room temperature. Upon completion of the reaction, the reaction was terminated by adding 20 mL of aqueous saturated ammonium chloride solution, and the reaction mixture was extracted with ethyl acetate (20 mL×3). The organic layer thus obtained was treated with anhydrous magnesium sulfate to remove water. The precipitate was filtered out and the resulting solution was concentrated by distillation under reduced pressure, and purified by column chromatography to obtain 895 mg (2.79 mmol, 95%) of the desired compound.

$^1$H NMR (300 MHz, CDCl₃): d 7.41 (d, 2H, J=8.2 Hz), 7.23 (d, 2H, J=8.1 Hz), 0.90 (s, 9H), 0.22 (s, 9H), 0.00 (s, 6H).

2) Synthesis of tert-butyldimethyl((4-((trimethylsilyl)ethynyl)benzyl)-oxy)silane-d₀

Under argon condition, (4-((trimethylsilyl)ethynyl)phenyl)-methanol (258 mg, 1.26 mmol) was dissolved in 5 mL of dry THF, and then cooled to 0° C., and imidazole (103 mg, 1.52 mmol) and TBSCl (228 mg, 1.52 mmol) dissolved in 3 mL of dry THF were added thereto. Then, the temperature was raised to room temperature and the reaction solution was stirred for 15 hours at room temperature. Upon completion of the reaction, the reaction was terminated by adding 10 mL of aqueous saturated ammonium chloride solution and the reaction mixture was extracted with ethyl acetate (10 mL×4). The organic layer thus obtained was treated with anhydrous magnesium sulfate to remove water. The precipitate was filtered out and the resulting solution was concentrated by distillation under reduced pressure and purified by column chromatography to obtain 383 mg (1.20 mmol, 95%) of the desired compound.

$^1$H NMR (300 MHz, CDCl₃): d 7.41 (d, 2H, J=8.2 Hz), 7.23 (d, 2H, J=8.1 Hz), 4.70 (s, 2H), 0.90 (s, 9H), 0.22 (s, 9H), 0.00 (s, 6H).

Step 4

1) Synthesis of tert-butyl((4-ethynylbenzyl)oxy)dimethylsilane-d₂

Under argon condition, tert-butyldimethyl((4-((trimethylsilyl)-ethynyl)benzyl)oxy)silane-d₂ (1.16 g, 3.62 mmol) and potassium carbonate (1.00 g, 7.24 mmol) were dissolved in 12 mL of methanol and stirred for 2 hours at room temperature. Upon completion of the reaction, the reaction was terminated by adding 15 mL of aqueous saturated ammonium chloride solution and the reaction mixture was extracted with ethyl acetate (10 mL×3). The organic layer thus obtained was treated with anhydrous magnesium sulfate to remove water. The precipitate was filtered out and the resulting solution was concentrated by distillation under reduced pressure and purified by column chromatography to obtain 858 mg (3.45 mmol, 95%) of the desired compound.

$^1$H NMR (300 MHz, CDCl₃): d 7.44 (d, 2H, J=8.2 Hz), 7.25 (d, 2H, J=8.5 Hz), 3.02 (s, 1H), 0.92 (s, 9H), 0.01 (s, 6H).

2) Synthesis of tert-butyl((4-ethynylbenzyl)oxy)dimethylsilane-d₀

Under argon condition, tert-butyldimethyl((4-((trimethylsilyl)-ethynyl)benzyl)oxy)silane (383 mg, 2.40 mmol) and potassium carbonate (332 mg, 2.40 mmol) were dissolved in 4 mL of methanol and then stirred for 2 hours at room temperature. Upon completion of the reaction, the reaction was terminated by adding 10 mL of aqueous saturated ammonium chloride solution and the reaction mixture was extracted with ethyl acetate (5 mL×4). The organic layer thus obtained was treated with anhydrous magnesium sulfate to remove water. The precipitate was filtered out, and the resulting solution was concentrated by distillation under reduced pressure, and purified by column chromatography to obtain 280 mg (1.14 mmol, 95%) of the desired compound.

$^1$H NMR (300 MHz, CDCl$_3$): d 7.44 (d, 2H, J=8.2 Hz), 7.25 (d, 2H, J=8.5 Hz), 4.72 (s, 2H), 3.02 (s, 1H), 0.92 (s, 9H), 0.01 (s, 6H).

Step 5

1) Synthesis of tert-butyldimethyl((4-(prop-1-yn-1-yl)benzyl)oxy)-silane-d$_5$

Under argon condition, tert-butyl((4-ethynylbenzyl)oxy) dimethyl-silane-d$_2$ (263 mg, 1.06 mmol) was dissolved in 5 mL of dry THF, and then cooled to −78° C., and n-butyl lithium (851 µL, 2.49 M solution in n-hexane, 2.12 mmol) was slowly added thereto. After stirring for 20 minutes at −78° C., iodomethane-d$_3$ (331 µL, 5.30 mmol) was added again thereto. Then, the temperature was raised to room temperature and the reaction solution was stirred for 30 minutes at room temperature. Upon completion of the reaction, the reaction was terminated by adding 5 mL of aqueous saturated ammonium chloride solution, and the reaction mixture was extracted with ethyl acetate (5 mL×3). The organic layer thus obtained was treated with anhydrous magnesium sulfate to remove water. The precipitate was filtered out and the resulting solution was concentrated by distillation under reduced pressure, and purified by column chromatography to obtain 280 mg (1.05 mmol, 99%) of the desired compound.

$^1$H NMR (300 MHz, CDCl$_3$): d 7.35 (d, 2H, J=8.2 Hz), 7.22 (d, 2H, J=8.2 Hz), 0.93 (s, 9H), 0.07 (s, 6H).

2) Synthesis of tert-butyldimethyl((4-(prop-1-yn-1-yl)benzyl)oxy)-silane-d$_0$

Under argon condition, tert-butyl((4-ethynylbenzyl)oxy) dimethyl-silane (247 mg, 1.00 mmol) was dissolved in 5 mL of dry THF, and then cooled to −78° C., and n-butyl lithium (805 µL, 2.49 M solution in n-hexane, 2.00 mmol) was slowly added thereto. After stirring for 20 minutes at −78° C., iodomethane-d$_0$ (313 µL, 5.00 mmol) was added again thereto. Then, the temperature was raised to room temperature and the reaction solution was stirred for 30 minutes at room temperature. Upon completion of the reaction, the reaction was terminated by adding 10 mL of aqueous saturated ammonium chloride solution and the reaction mixture was extracted with ethyl acetate (5 mL×4). The organic layer thus obtained was treated with anhydrous magnesium sulfate to remove water. The precipitate was filtered out, and the resulting solution was concentrated by distillation under reduced pressure, and purified by column chromatography to obtain 253 mg (0.971 mmol, 97%) of the desired compound.

$^1$H NMR (300 MHz, CDCl$_3$): d 7.35 (d, 2H, J=8.2 Hz), 7.22 (d, 2H, J=8.2 Hz), 4.70 (s, 2H), 2.03 (s, 3H), 0.93 (s, 9H), 0.07 (s, 6H).

Step 6

1) Synthesis of (4-(prop-1-yn-1-yl)phenyl)methanol-d$_5$

Under argon condition, tert-butyldimethyl((4-(prop-1-yn-1-yl)-benzyl)oxy)silane-d$_5$ (280 mg, 1.05 mmol) was dissolved in 5 mL of dry THF, and then n-butylammonium fluoride (TBAF; 1.58 mL, 1.0 M solution in tetrahydrofuran, 1.58 mmol) was slowly added and the reaction mixture was stirred for 30 minutes at room temperature. Upon completion of the reaction, the reaction was terminated by adding 5 mL of aqueous saturated ammonium chloride solution and the reaction mixture was extracted with ethyl acetate (5 mL×4). The organic layer thus obtained was treated with anhydrous magnesium sulfate to remove water. The precipitate was filtered out and the resulting solution was concentrated by distillation under reduced pressure and purified by column chromatography to obtain 198 mg (0.838 mmol, 88%) of the desired compound.

$^1$H NMR (300 MHz, CDCl$_3$): d 7.33 (d, 2H, J=8.2 Hz), 7.20 (d, 2H, J=8.1 Hz).

2) Synthesis of (4-(prop-1-yn-1-yl)phenyl)methanol-d$_0$

Under argon condition, tert-butyldimethyl((4-(prop-1-yn-1-yl)-benzyl)oxy)silane-d$_0$ (326 mg, 1.25 mmol) was dissolved in 5 mL of dry THF, and then n-butylammonium fluoride (TBAF; 1.88 mL, 1.0 M solution of tetrahydrofuran, 1.88 mmol) was slowly added and the reaction mixture was stirred for 30 minutes at 0° C. Upon completion of the reaction, the reaction was terminated by adding 5 mL of aqueous saturated ammonium chloride solution, and the reaction mixture was extracted with ethyl acetate (5 mL×4). The organic layer thus obtained was treated with anhydrous magnesium sulfate to remove water. The precipitate was filtered out and the resulting solution was concentrated by distillation under reduced pressure and purified by column chromatography to obtain 182 mg (1.24 mmol, 99%) of the desired compound.

$^1$H NMR (300 MHz, CDCl$_3$): d 7.33 (d, 2H, J=8.2 Hz), 7.20 (d, 2H, J=8.1 Hz), 4.56 (s, 2H), 2.44 (br, 1H), 2.01 (s, 3H).

Step 7

1) Synthesis of 1-(iodomethyl)-4-(prop-1-yn-1-yl)benzene-d$_5$ (4-(prop-1-yn-1-yl)phenyl)methanol-d$_5$ (140 mg, 0.926 mmol) was dissolved in 5 mL of well-dried DCM under argon condition and then cooled to 0° C. and methasulfonyl chloride (MsCl; 86.3 µL, 1.11 mmol) and triethylamine (Et$_3$N; 194 µL, 1.39 mmol) were added thereto. Upon completion of the reaction which occurred after stirring for 30 minutes at 0° C., the reaction was terminated by adding 5 mL of water and the reaction mixture was extracted with DCM (5 mL×3). The organic layer thus obtained was treated with anhydrous magnesium sulfate to remove water. The precipitate was filtered out and the resulting solution was concentrated by distillation under reduced pressure and dissolved again in 10 mL of acetone. Sodium iodide (NaI; 207 mg, 1.39 mmol) was then added. Upon completion of the reaction which occurred after stirring for one hour at room temperature, the reaction solution was dried by distilling the solvent under reduced pressure. 10 mL of water was added to the residue and the mixture was extracted with ethyl acetate (10 mL×3). The organic layer thus obtained was treated with anhydrous magnesium sulfate to remove water. The precipitate was filtered out and the resulting solution was concentrated by distillation under reduced pressure and purified by column chromatography to obtain 220 mg (0.843 mmol, 91%) of the desired compound (reporter-d$_5$)

$^1$H NMR (300 MHz, CDCl$_3$): d 7.30-7.27 (m, 2H). .

2) Synthesis of 1-(iodomethyl)-4-(prop-1-yn-1-yl) benzene-d$_0$ (4-(prop-1-yn-1-yl)phenyl)methanol-d$_5$ (182 mg, 1.24 mmol) was dissolved in 4 mL of well-dried DCM under argon condition and then cooled to 0° C. and methansulfonyl chloride (MsCl; 116 μL, 1.49 mmol) and triethylamine (Et$_3$N; 260 μL, 1.87 mmol) were added thereto. Upon completion of the reaction which occurred after stirring for 30 minutes at 0° C., the reaction was terminated by adding 5 mL of water and the reaction mixture was extracted with DCM (5 mL×3). The organic layer thus obtained was treated with anhydrous magnesium sulfate to remove water, and the precipitate was filtered out. The resulting solution was concentrated by distillation under reduced pressure and dissolved again in 12 mL of acetone. Sodium iodide (NaI: 280 mg, 1.87 mmol) was then added. Upon completion of the reaction which occurred after stirring for one hour at room temperature, the reaction solution was dried by distillating the solvent under reduced pressure. 10 mL of water was added to the residue and the mixture was extracted with ethyl acetate (10 mL×3). The organic layer thus obtained was treated with anhydrous magnesium sulfate to remove water. The precipitate was filtered out and the resulting solution was concentrated by distillation under reduced pressure and purified by column chromatography to obtain 279 mg (1.09 mmol, 88%) of the desired compound (reporter-d$_0$).

$^1$H NMR (300 MHz, CDCl$_3$): d 7.30-7.27 (m, 2H), 4.42 (s, 2H), 2.02 (s, 3H).

The procedures for synthesis of balance-d$_5$ and balance-d$_0$ from the reporter unit as synthesized above and NMR results of the compounds produced from respective steps are shown in the following steps 8 to 10.

Step 8

1) Synthesis of diethyl 2-(4-(prop-1-yn-1-yl)benzyl) malonate-d$_5$

Under argon condition, 1-(iodomethyl)-4-(prop-1-yn-1-yl)benzene-d$_5$ (0.392 mmol) and sodium hydride (NA: 19.8 mg, 60% mineral oil mixture, 0.473 mmol) were dissolved in 2 mL of dry DMF and then cooled to 0° C. and diethyl malonate (89.8 μL, 0.592 mmol) was added thereto. The temperature was then raised to room temperature and the reaction mixture was stirred for 3 hours at room temperature. Upon completion of the reaction, the reaction was terminated by adding 5 mL of aqueous saturated ammonium chloride solution, and the reaction mixture was extracted with diethyl ether (3 mL×4). The organic layer thus obtained was treated with anhydrous magnesium sulfate to remove water. The precipitate was filtered out and the resulting solution was concentrated by distillation under reduced pressure and purified by column chromatography to obtain 88.5 mg (0.302 mmol, 77%) of the desired compound.

$^1$H NMR (300 MHz, CDCl$_3$): d 7.28-7.23 (m, 2H), 7.11-7.07 (m, 2H), 4.17-4.06 (m, 4H), 3.57 (s, 1H), 1.21-1.14 (m, 3H).

2) Synthesis of diethyl 2-(4-(propr-1-yn-1-yl)benzyl) malonate-d$_0$

Under argon condition, 1-(iodomethyl)-4-(prop-1-yn-1-yl)benzene-d$_0$ (98.0 mg, 0.383 mmol) and sodium hydride (NA: 18.4 mg, 60% mineral oil mixture, 0.459 mmol) were dissolved in 3 mL of dry DMF and then cooled to 0° C. and diethyl malonate (87.2 μL, 0.574 mmol) was added thereto. Then, the temperature was raised to room temperature and the reaction mixture was stirred for 3 hours at room temperature. Upon completion of the reaction, the reaction was terminated by adding 5 mL of aqueous saturated ammonium chloride solution and the reaction mixture was extracted with diethyl ether (3 mL×4). The organic layer thus obtained was treated with anhydrous magnesium sulfate to remove water. The precipitate was filtered out and the resulting solution was concentrated by distillation under reduced pressure and purified by column chromatography to obtain 94.8 mg (0.329 mmol, 86%) of the desired compound.

Step 9

1) Synthesis of 3-(4-(prop-1-yn-1-yl)phenyl)propione-d$_5$ ethyl ester

Under argon condition, diethyl 2-(4-(prop-1-yn-1-yl)benzyl)-malonate-d$_5$ (88.5 mg, 0.302 mmol) was dissolved in 2 mL of dry DMF, and then sodium chloride (35.3 mg, 0.604 mmol) and 100 μL of water were added thereto and stirred for 2 days under reflux condition. Upon completion of the reaction, the reaction was terminated by adding 3 mL of water and the reaction mixture was extracted with diethyl ether (3 mL×4). The organic layer thus obtained was treated with anhydrous magnesium sulfate to remove water. The precipitate was filtered out and the resulting solution was concentrated by distillation under reduced pressure and purified by column chromatography to obtain 50.0 mg (0.226 mmol, 75%) of the desired compound.

$^1$H NMR (300 MHz, CDCl$_3$): d 7.28 (d, 2H, J=8.1 Hz), 7.08 (d, 2H, J=8.1 Hz), 4.08 (q, 2H, J=7.2 Hz), 2.56 (s, 2H), 1.19 (t, 3H, J=7.2 Hz).

2) Synthesis of ethyl 3-(4-(prop-1-yn-1-yl)phenyl) propione-d$_0$ ethyl ester Under argon condition, diethyl 2-(4-(prop-1-yn-1-yl)benzyl)-malonate-d$_0$ (94.8 mg, 0.329 mmol) was dissolved in 2 mL of dry DMF and then sodium chloride (38.5 mg, 0.658 mmol) and 200 μL of water were added thereto and stirred for 2 days under reflux condition. Upon completion of the reaction, the reaction was terminated by adding 3 mL of water and the reaction mixture was extracted with diethyl ether (3 mL×4). The organic layer thus obtained was treated with anhydrous magnesium sulfate to remove water. The precipitate was filtered out and the resulting solution was concentrated by distillation under reduced pressure and purified by column chromatography to obtain 50.0 mg (0.231 mmol, 70%) of the desired compound.

$^1$H NMR (300 MHz, CDCl$_3$): d 7.28 (d, 2H, J=8.1 Hz), 7.08 (d, 2H, J=8.1 Hz), 4.08 (q, 2H, J=7.2 Hz), 2.89 (t, 2H, J=7.6 Hz), 2.56 (t, 2H, J=8.0 Hz), 2.00 (s, 3H), 1.19 (t, 3H, J=7.2 Hz).

Step 10

1) Synthesis of 3-(4-(prop-1-yn-1-yl)phenyl)propionic acid-d$_5$ (balance-d$_5$)

3-(4-(prop-1-yn-1-yl)phenyl)propione-d$_5$ ethyl ester (43.0 mg, 0.194 mmol) was dissolved in 0.5 mL of methanol. 100 μL of 20% aqueous sodium hydroxide solution was added then thereto and stirred for 2 hours at room temperature. Upon completion of the reaction, the reaction solution was diluted with 3 mL of ethyl acetate and then neutralized by adding 200 μL of 10% aqueous hydrogen chloride solution. After removing water with anhydrous magnesium sulfate and filtering out the precipitate, the resulting solution was concentrated by distillation under reduced pressure and purified by column chromatography to obtain 32.2 mg (0.167 mmol, 86%) of the desired compound (balance-$d_5$).

$^1$H NMR (300 MHz, CDCl$_3$): d 7.30 (d, 2H, J=8.1 Hz), 7.10 (d, 2H, J=8.1 Hz), 2.64 (s, 2H).

2) Synthesis of 3-(4-(prop-1-yn-1-yl)phenyl)propionic acid-$d_0$ (Balance-$d_0$)

3-(4-(prop-1-yn-1-yl)phenyl)propione-$d_0$ ethyl ester (50.0 mg, 0.231 mmol) was dissolved in 0.5 mL of methanol and then 100 µL of 20% aqueous sodium hydroxide solution was added thereto and stirred for 2 hours at room temperature. Upon completion of the reaction, the reaction solution was diluted with 3 mL of ethyl acetate and then neutralized by adding 200 µL of 10% aqueous hydrogen chloride solution. After removing water with anhydrous magnesium sulfate and filtering out the precipitate, the resulting solution was concentrated by distillation under reduced pressure and purified by column chromatography to obtain 37.3 mg (0.198 mmol, 86%) of the desired compound (balance-$d_0$).

$^1$H NMR (300 MHz, CDCl$_3$): d 7.30 (d, 2H, J=8.1 Hz), 7.10 (d, 2H, J=8.1 Hz), 2.91 (t, 2H, J=7.6 Hz), 2.64 (t, 2H, J=8.0 Hz), 2.02 (s, 3H).

Using the reporter unit and the balance unit as prepared above, the procedures for synthesis of the isobar and multiplexed isobaric labeling agent and the NMR results of the compounds synthesized from respective steps are shown in the following steps 11 to 13. Since the methods for synthesis of multiplexed isobars are identical to each other, only for the case of isobaric labeling agent tag $\alpha_{129}$ were the procedures specifically illustrated. For the cases of other isobaric labeling agents, only the differences in synthetic procedures were described.

Step 11: Synthesis of methyl 2-((4-(prop-1-yn-1-yl)benzyl)amino)acetate-$d_0$

Under argon condition, glycine methyl ester (169 mg, 1.34 mmol) was dissolved in 2 mL of dry DMF and then DIPEA (292 µL, 1.68 mmol) and 1-(iodomethyl)-4-(prop-1-yn-1-yl)benzene-$d_0$ (reporter-$d_0$: 232 mg, 0.892 mmol) were added and stirred for one day at room temperature. Upon completion of the reaction, the reaction was terminated by adding 5 mL of water and the reaction mixture was extracted with diethyl ether (5 mL×4). The organic layer thus obtained was treated with anhydrous magnesium sulfate to remove water. The precipitate was filtered out and the resulting solution was concentrated by distillation under reduced pressure and purified by column chromatography to obtain 58.6 mg (0.270 mmol, 80%) of the desired compound.

$^1$H NMR (300 MHz, CDCl$_3$): d 7.30 (d, 2H, J=8.2 Hz), 7.19 (d, 2H, J=8.2 Hz), 3.72 (s, 2H), 3.67 (s, 3H), 3.35 (s, 2H), 2.20 (br, 1H), 1.99 (s, 3H).

Step 12: Synthesis of methyl 2-(N-(4-(prop-1-yn-1-yl)benzyl)-3-(4-(prop-1-yn-1-yl)phenyl)propanamido)acetate-$d_5$ Methyl 2-((4-(prop-1-yn-1-yl)benzyl)amino)acetate-$d_0$ (18.3 mg, 0.0845 mmol) and 3-(4-(prop-1-yn-1-yl)phenyl)propanoic acid-$d_5$ (balance-$d_5$; 13.6 mg, 0.0704 mmol) were dissolved in 1 mL of well-dried DCM under argon condition and then EDC (40.5 mg, 0.211 mmol), HOBt (28.5 mg, 0.211 mmol) and DIPEA (60.3 µL, 0.352 mmol) were added thereto and stirred for 20 hours at room temperature. Upon completion of the reaction, the reaction was terminated by adding 3 mL of water and the reaction mixture was extracted with DCM (3 mL×4). The organic layer thus obtained was treated with anhydrous magnesium sulfate to remove water. The precipitate was filtered out and the resulting solution was concentrated by distillation under reduced pressure and purified by column chromatography to obtain 25.0 mg (0.0759 mmol, 91%) of the desired compound.

Major isomer: $^1$H NMR (300 MHz, CDCl$_3$): d 7.33-7.24 (m, 4H), 7.11-6.96 (m, 4H), 4.51 (s, 2H), 4.00 (s, 2H), 3.64 (s, 3H), 2.65 (s, 2H), 2.02 (s, 3H). Minor isomer: $^1$H NMR (300 MHz, CDCl$_3$): d 7.33-7.24 (m, 4H), 7.11-6.96 (m, 4H), 4.58 (s, 2H), 3.81 (s, 2H), 3.60 (s, 3H), 2.52 (s, 2H), 2.02 (s, 3H).

Step 13: Synthesis of 2-(N-(4-(prop-1-yn-1-yl)benzyl-3-(4-(prop-1-yn-1-yl)phenyl)propanamido)acetic acid-$d_5$ Methyl 2-(N-(4-(prop-1-yn-1-yl)benzyl)-3-(4-(prop-1-yn-1-yl)-phenyl)propanamido)acetate-$d_5$ (25.0 mg, 0.0637 mmol) was dissolved in 0.5 mL of methanol. 100 µL of 20% aqueous sodium hydroxide solution was then added thereto and stirred for 2 hours at room temperature. Upon completion of the reaction, the reaction solution was diluted with 3 mL of ethyl acetate and then neutralized by adding 200 µL of 10% aqueous hydrogen chloride solution. After removing water with anhydrous magnesium sulfate and filtering out the precipitate, the resulting solution was concentrated by distillation under reduced pressure, and purified by column chromatography to obtain 21.0 mg (0.0554 mmol, 87%) of the isobaric labeling agent tag $\alpha_{129}$.

Major isomer: $^1$H NMR (300 MHz, CDCl$_3$): d 77.32-7.23 (m, 4H), 7.09-7.94 (m, 4H), 4.47 (s, 2H), 3.97 (s, 2H), 2.62 (s, 2H), 2.02 (s, 3H). Minor isomer: $^1$H NMR (300 MHz, CDCl$_3$): d 7.32-7.23 (m, 4H), 7.09-7.94 (m, 4H), 4.56 (s, 2H), 3.79 (s, 2H), 2.53 (s, 2H), 2.00 (s, 3H).

The isobaric labeling agents tag $\alpha_{131}$, tag $\alpha_{132}$ and tag $\alpha_{134}$ were prepared according to the method similar to said steps 11 to 13 as shown in the following.

Isobaric Labeling Agent α131

The isobaric labeling agents tag $\alpha_{131}$ was synthesized according to the same procedures as the isobaric labeling agent tag $\alpha_{129}$ except that during the synthetic procedures step 11 used reporter-$d_2$ and step 12 used balance-$d_3$.

Major isomer: $^1$H NMR (300 MHz, CDCl$_3$): d 7.32-7.23 (m, 4H), 7.09-7.94 (m, 4H), 3.97 (s, 2H), 2.90 (t, 2H, J=7.9 Hz), 2.64 (t, 2H, J=8.0 Hz), 2.02 (s, 3H). Minor isomer: $^1$H NMR (300 MHz, CDCl$_3$): d 7.32-7.23 (m, 4H), 7.09-7.94 (m, 4H), 3.79 (s, 2H), 2.93 (t, 2H, J=7.9 Hz), 2.55 (t, 2H, d'=8.0 Hz), 2.00 (s, 3H).

Isobaric Labeling Agent α132

The isobaric labeling agents tag $\alpha_{132}$ was synthesized according to the same procedures as the isobaric labeling agent tag $\alpha_{129}$ except that during the synthetic procedures step 11 used reporter-$d_3$ and step 12 used balance-$d_2$.

Major isomer: $^1$H NMR (300 MHz, CDCl$_3$): d 7.32-7.23 (m, 4H), 7.09-7.94 (m, 4H), 4.47 (s, 2H), 3.97 (s, 2H), 2.62 (s, 2H), 2.02 (s, 3H). Minor isomer: $^1$H NMR (300 MHz, CDCl$_3$): d 7.32-7.23 (m, 4H), 7.09-7.94 (m, 4H), 4.56 (s, 2H), 3.79 (s, 2H), 2.53 (s, 2H), 2.00 (s, 3H).

Isobaric Labeling Agent α134

The isobaric labeling agents tag $\alpha_{134}$ was synthesized according to the same procedures as the isobaric labeling agent tag $\alpha_{129}$ except that during the synthetic procedures step 11 used reporter-$d_5$ and step 12 used balance-$d_0$.

Major isomer: $^1$H NMR (300 MHz, CDCl$_3$): d 7.32-7.23 (m, 4H), 7.09-7.94 (m, 4H), 3.97 (s, 2H), 2.90 (t, 2H, J=7.9 Hz), 2.64 (t, 2H, J=8.0 Hz), 2.02 (s, 3H). Minor isomer: $^1$H NMR (300 MHz, CDCl$_3$): d 7.32-7.23 (m, 4H), 7.09-7.94 (m, 4H), 3.79 (s, 2H), 2.93 (t, 2H, J=7.9 Hz), 2.55 (t, 2H, J=8.0 Hz), 2.00 (s, 3H).

The following experiments for quantitative analysis were conducted using the compounds as prepared above.

Example 1-3

Experiment for Quantitative Analysis

Step 1: Coupling of Labeling Agent with Analyte

Figure 7:
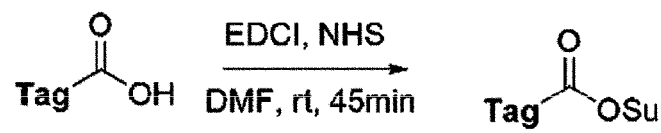
FIG. 7 shows one example of the activation method of the compound according to the present invention, wherein the compound is activated with succinimidyl ester and then coupled with peptide.
Figure 7:
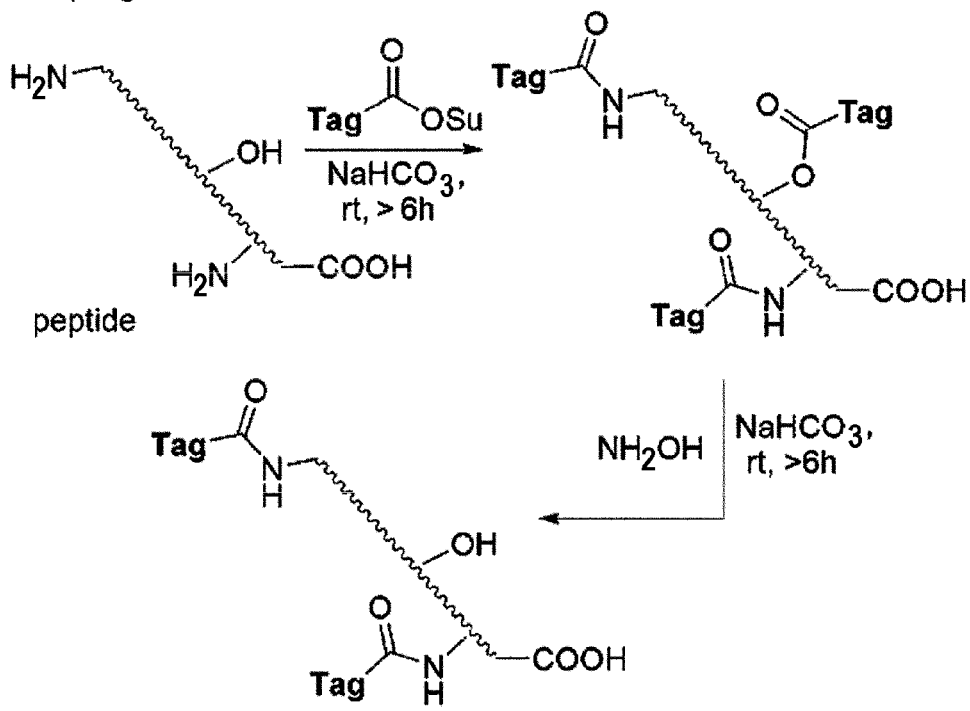
Figure 8A:
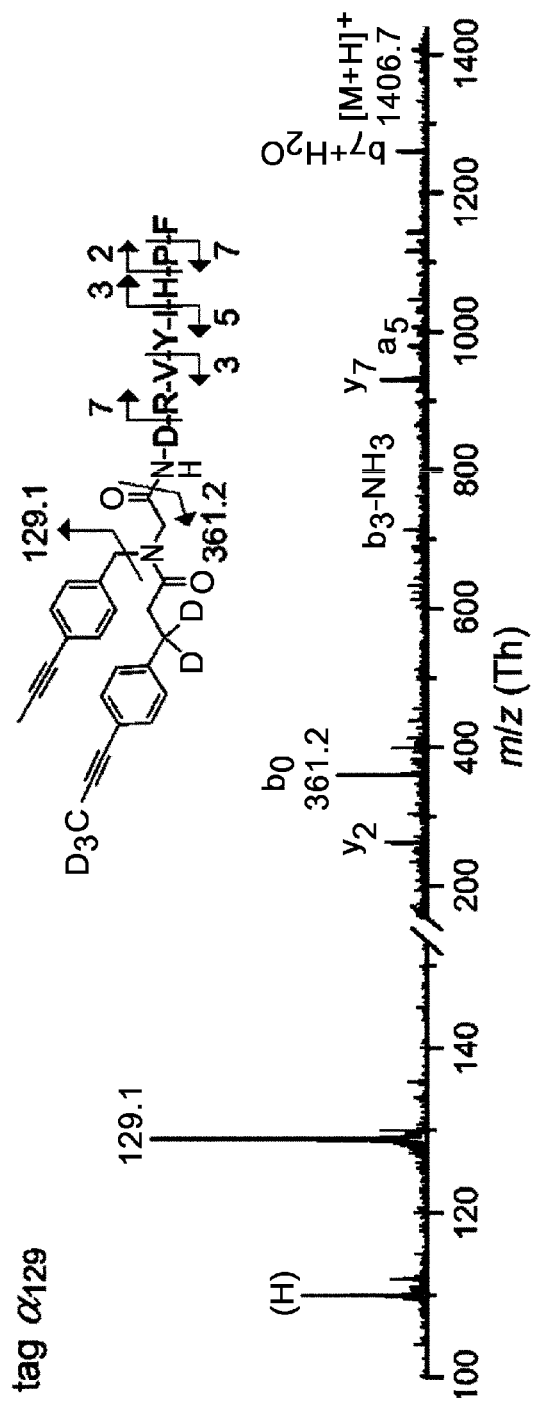
FIGS. 8(a) to 8(d) show the result obtained from use of the multiplexed isobar (tag $\alpha_{129}$-$\alpha_{134}$) and FIGS. 8(e) to 8(g) show the result obtained from use of the non-isobar (tag β-δ).
Figure 8B:
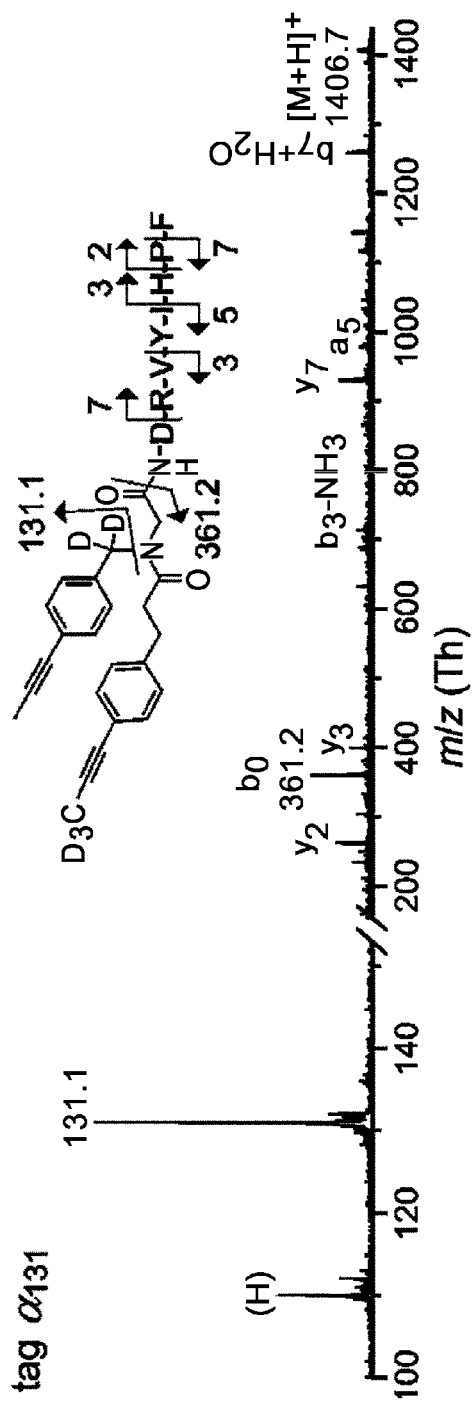
Figure 8C:
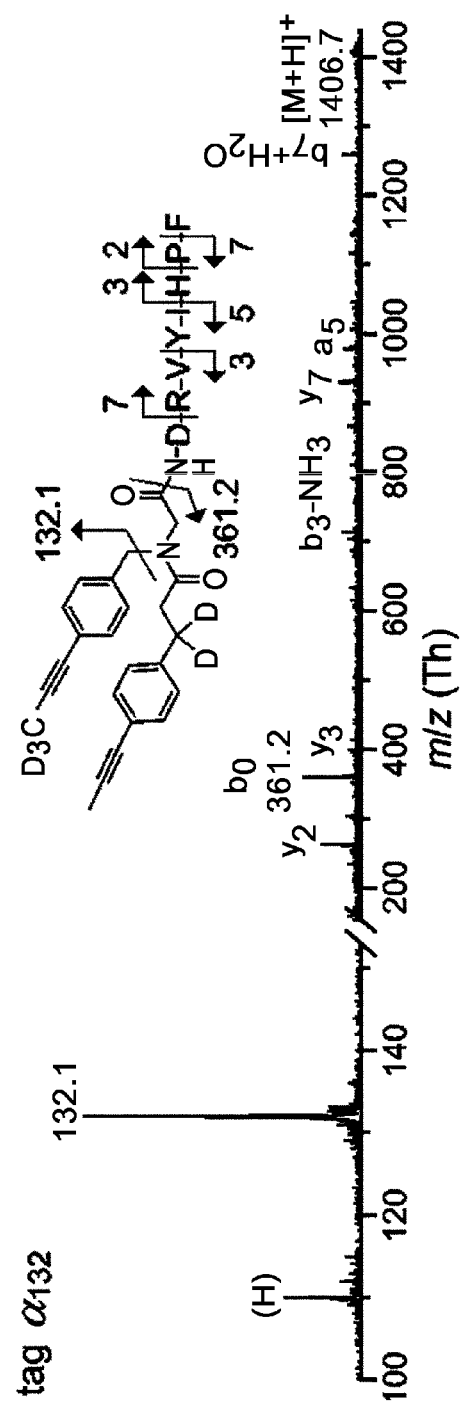
Figure 8D:
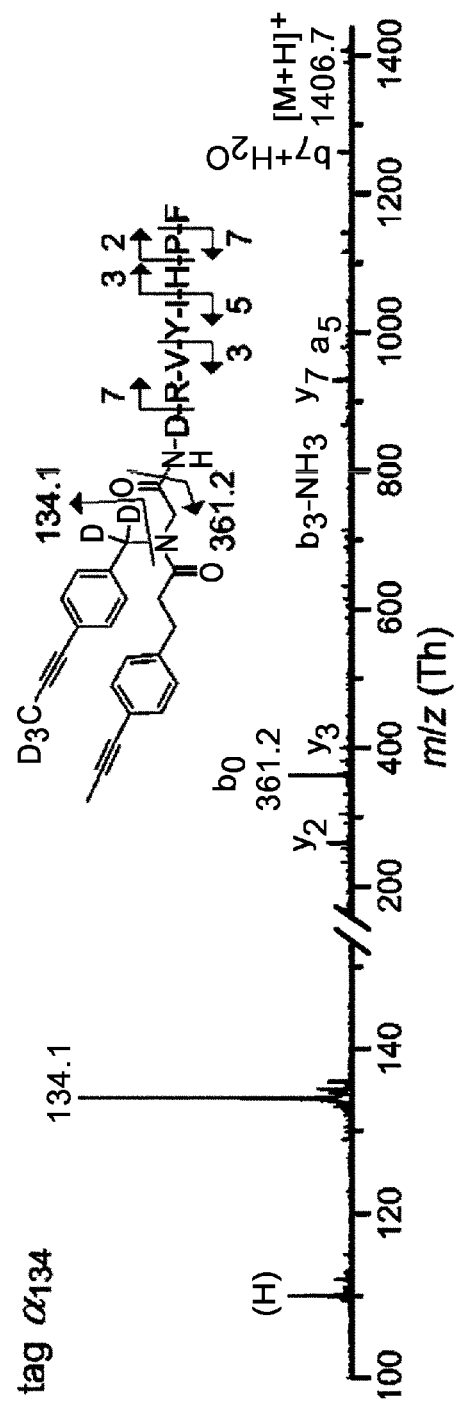
Figure 8E:
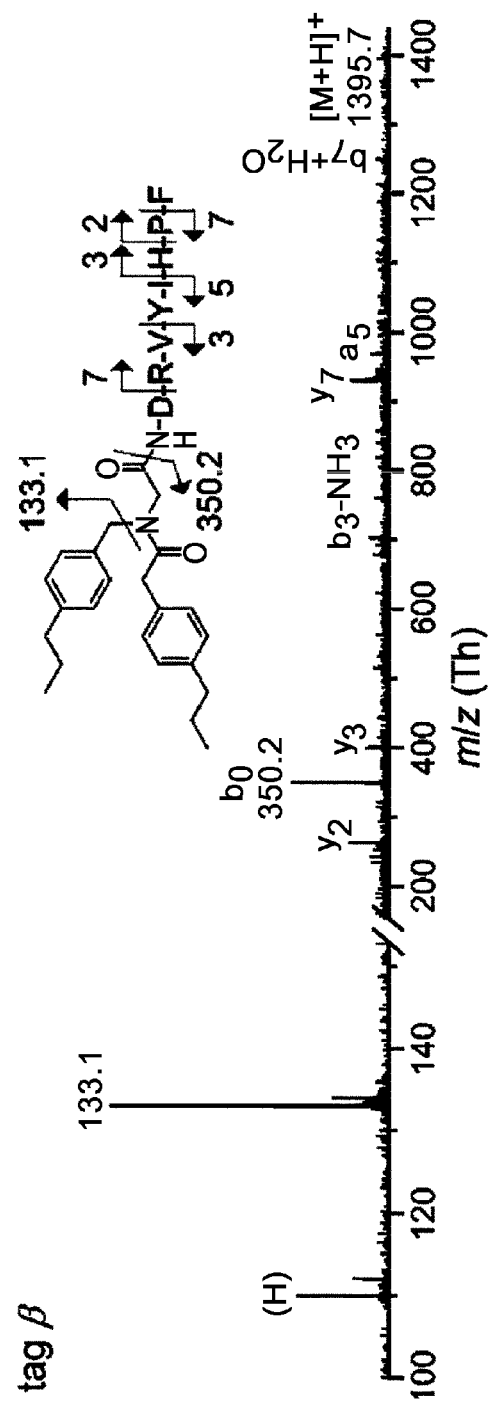
Figure 8F:
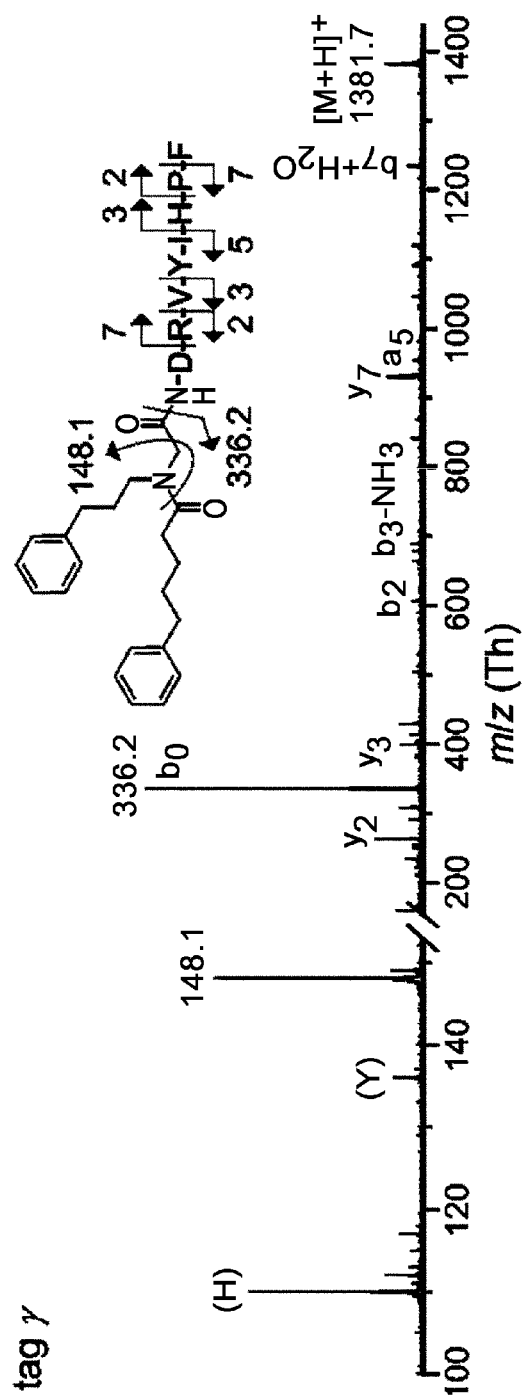
Figure 8G:
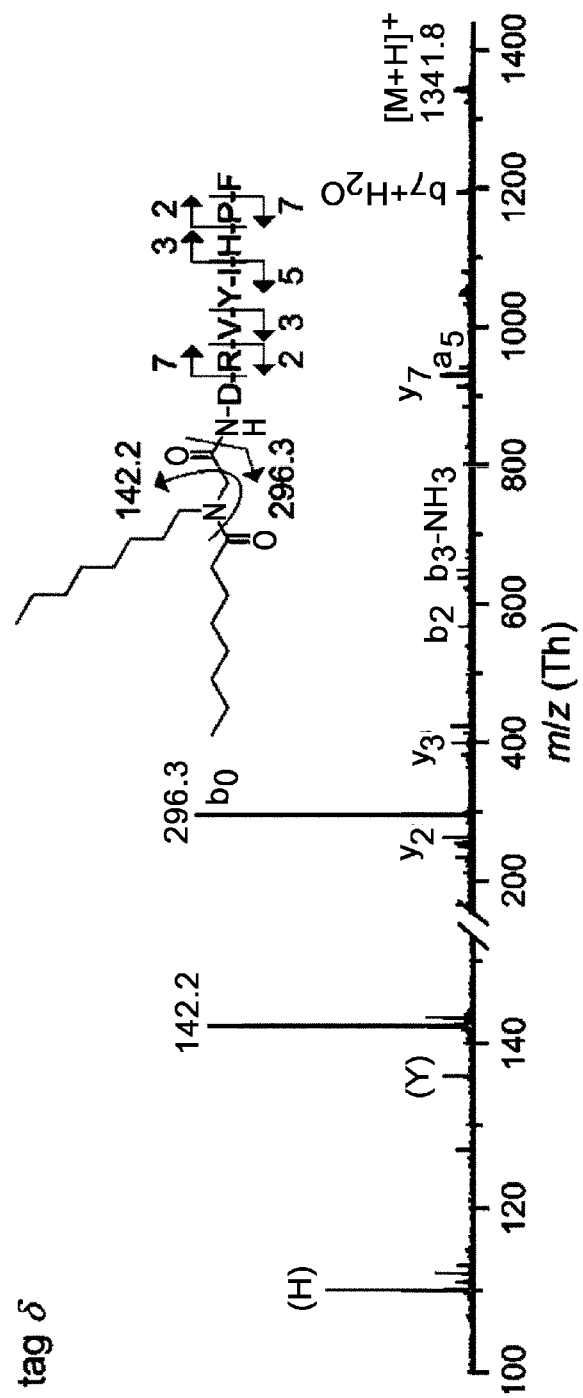

The coupling reaction of the compound of Example 1-2 with peptide is shown in FIG. 7. The compound of Example 1-2, EDC and N-hydroxysuccinimide (NHS) were dissolved in DMF, mixed so that their concentrations are 60, 35 and 40 mM, respectively, and reacted for 45 minutes at room temperature to activate carboxylic acid terminal group of the labeling agent as succinimidyl ester.

Peptide (tryptic BSA) obtained by decomposition of bovine serum albumin with trypsin enzyme or angiotensin II (DRVYIHPF) was dissolved in aqueous sodium hydrogen carbonate solution (NaHCO$_3$, 100 mM) and then the activated labeling agent was added thereto. The reaction was conducted for 6 hours or more. Since the labeling reaction which occurs on hydroxyl group with low labeling yield produces the analytes with either intact or modified hydroxyl group, for accurate quantification the side reaction labeled on hydroxyl group of peptide was removed using hydroxylamine (80 mM) dissolved in aqueous sodium hydrogen carbonate solution (100 mM). The whole reaction was terminated by adding trifluoroacetic acid (TFA).

Step 2: MALDI and LC-MALDI Mass Spectrometry

Labeled angiotensin II was diluted with 50 TA solution (0.1% TFA/50% acetonitrile/50% H$_2$O) and then mixed with HCCA matrix solution (α-cyano-4-hydroxycinnamic acid, 5 mg/mL 50 TA) at the ratio of 1:1. The mixture was mounted on a MALDI plate, dried, and then analyzed by means of tandem time-of-flight/time-of-flight (TOF/TOF) mass spectrometer. Through tandem mass spectrometry it was identified that the quantitation signals and labeled signals could be observed as designed and the intensities thereof.

Labeled tryptic BSA was used to identify the range of concentration or quantity of the analyte sample that can be measured with the isobaric labeling agent and further to identify whether multiplexed samples can be simultaneously quantitatively analyzed by interconnecting with liquid chromatography (LC). To identify the range of concentration of the sample that can be measured with the isobaric labeling agent the procedures for mixing the samples labeled with tag $\alpha_{129}$ and tag $\alpha_{131}$ among multiplexed isobars at the ratio of 3:1 and then diluting with 50 TA were repeated. The samples having their respective concentrations were mixed with HCCA matrix solution at the ratio of 1:1 and then loaded on MALDI plate. For this, peptides were loaded in the quantity of about 4200, 1300, 420, 130, 42, and 13 femtomole per spot. To test the multiplexed quantitative analysis interconnected with LC, tryptic BSAs labeled with four kinds of the isobars were mixed at the ratio of 2:1:4:8 and separated with nanoLC. Peptides eluted from LC were loaded on MALDI plate together with HCCA matrix solution, and analyzed with MALDI-TOF/TOF.

Experimental Results
1) Verification of Labeling Agent Using the Model Peptides

The masses of the model peptides (angiotensin II, DRVYI-HPF) coupled with respective labeling agents were analyzed. As the result, ions were observed at the mass values (tag $\alpha_{129}$-$\alpha_{134}$ was 1406.7, tag β was 1395.7, tag γ was 1381.7, and tag δ was 1341.8 Th) coupled with one labeling agent. For more accurate verification, ions observed in mass spectrum were selected to conduct tandem mass spectrometry. The result thereof is shown in FIG. 8.

FIG. 8($a$) to FIG. 8($d$) show the results obtained from peptides labeled with multiplexed isobars (tag $\alpha_{129}$-$\alpha_{134}$) and FIG. 8($e$) to FIG. 8($g$) show the results obtained from peptides labeled with non-isobars tag β, tag γ, and tag δ. Ions produced from respective labeling agents, i.e. labeled signals and quantitation signals, were observed at the designed mass values. The labeled signals were observed at 361 for tag $\alpha_{129}$-$\alpha_{134}$, 350 for tag β, 336 for tag γ, and 296 Th for tag δ. The quantitation signals were observed at 129 for tag $\alpha_{129, 131}$ for tag $\alpha_{131}$, 132 for tag $\alpha_{132}$, 134 for tag $\alpha_{134}$, 133 for tag β, 148 for tag γ, and 142 Th for tag δ.

Figure 9:
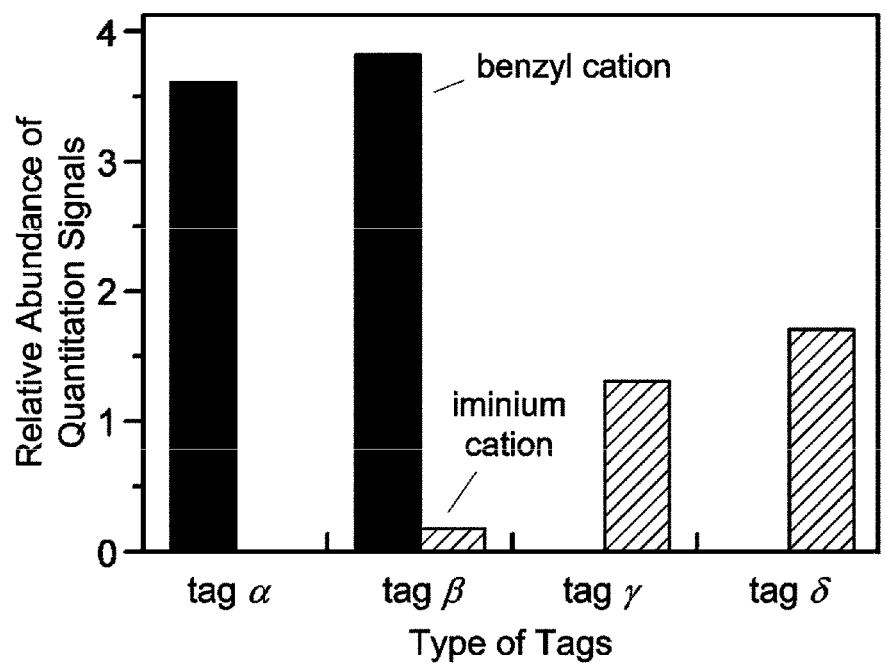
FIG. 9 shows the relative intensity of quantitation signals (benzyl cation and imminium cation) produced from the compound according to one example of the present invention. The intensity of quantitation signals is expressed as the relative value to the intensity of histidine immonium ion (110 Th) produced from the model peptide.

The intensities of quantitation signals produced from respective labeling agents are shown in FIG. 9 in comparison with histidine immonium ion (110 Th) which is most strongly observed among fragment ions of the model peptide. Different types of the quantitation signals were observed depending on the structures of the labeling agents. Specifically, for tag α and tag β, of which the reporter unit is benzyl derivatives the quantitation signal of benzyl cation structure was observed, and for tag γ and tag δ having no benzyl derivatives, the quantitation signal of imminium cation structure was observed. Although the types of quantitation signals were different depending on the labeling agents, the quantitation signals of respective labeling agents were much more strongly observed as compared to fragment ions of the model peptide. For fragment ions of the model peptide, fragment ions comprising C-terminal group of peptide, i.e., y$_2$, y$_3$, and y$_7$, were observed at the same position regardless of the labeling agents, and fragment ions comprising N-terminal group of peptide, i.e., b$_2$, b$_3$–NH$_3$, a$_5$, and b$_7$+H$_2$O, etc. were observed at the position having the mass increased as much as {molecular weight of respective labeling agent–H$_2$O}. In view of the fact that in the results of mass spectrometry and tandem mass spectrometry the molecular weights and quantitation and labeled signals of respective labeling agents as synthesized were observed as expected, it could be identified that respective labeling agents were synthesized as designed. Further, from fragment ions of peptides it was also identified that the labeling agent was labeled only on N-terminal group.

Figure 10:
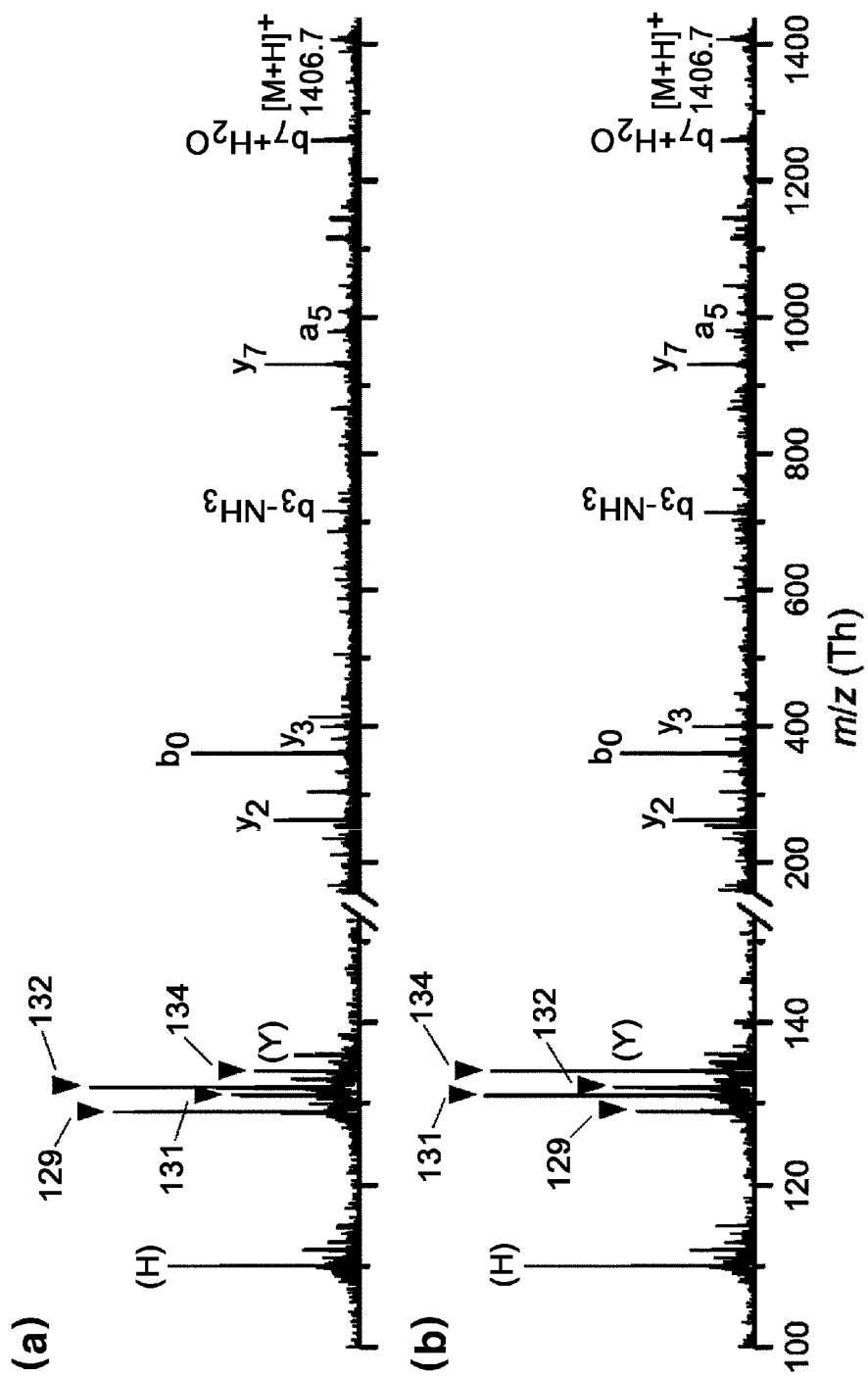
FIG. 10 shows the result of tandem mass spectrometry from mixing the model peptides labeled with the multiplexed isobar according to one example of the present invention, at a certain ratio.

The model peptides labeled with the multiplexed isobars were mixed at a certain ratio and then subjected to tandem mass spectrometry. The result thereof was shown in FIG. 10. The case where the mixing ratio (molar ratio) is tag $\alpha_{129}$:$\alpha_{131}$:$\alpha_{132}$:$\alpha_{134}$=2:1:2:1 was depicted in FIG. 10($a$) and the case where said ratio is 1:2:1:2 was depicted in FIG. 10($b$), wherein the quantitation signals of respective multiplexed isobaric labeling agents were marked as an inverted triangle. As compared to FIG. 8($a$) to FIG. 8($d$) showing the result obtained from separate analysis of respective multiplexed isobars, in the multiplexed quantitative analysis the intensity of respective quantitation signals was relatively weak and the fragment ions of peptides were more strongly observed. As above, in the case where the multiplexed isobars have identical total molecular weights but differ only in the mass values of quantitation signals used, though the quantitation signals were different the mass values of other ions were identical and thus overlapped to strengthen the intensity thereof. For this reason, similar to the labeling agents developed by the present invention, if the quantitation signals are more strongly observed, it is advantageous to the multiplexed quantitative analysis.

2) Functional Verification of the Multiplexed Isobars Using Tryptic BSA

Figure 11:
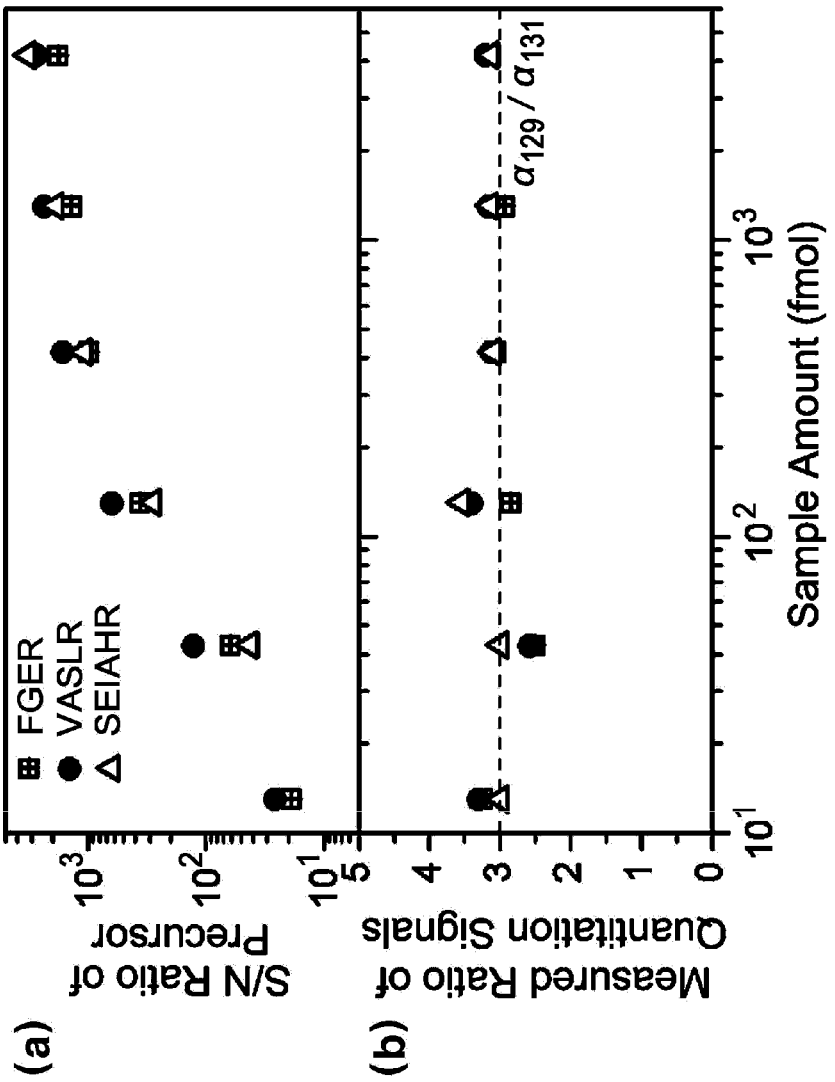
FIG. 11 shows the result obtained from measuring the quantity or concentration range of peptides which can be measured using the multiplexed isobar (tag $\alpha_{129}$-$\alpha_{134}$). It shows the result of tandem mass spectrometry of FGER, VASLR and SEIAHR in tryptic BSA (bovine serum albumin) labeled with the multiplexed isobar, wherein peptides labeled with tag $\alpha_{129}$ and tag $\alpha_{131}$ are mixed at a ratio of 3:1, the quantity of total proteins is varied from 4.2 picomole to 13 femtomole and then tandem mass spectrometry is conducted. The intensity of parent ions observed at each of concentrations is shown in FIG. 11(a) and the ratio of quantitation signals measured by tandem mass spectrometry is shown in FIG. 11(b).

The range of quantity or concentration which can be measured using the multiplexed isobars was depicted in FIG. 11. The experiment was conducted using FGER, VASLR, and SEIAHR which are peptides relatively strongly observed among tryptic BSA labeled with isobars, so that the absolute quantity of BSA can be well reflected. Peptides labeled with tag $\alpha_{129}$ and tag $\alpha_m$ were mixed at the ratio of 3:1 and then subjected to tandem mass spectrometry with varying the quantity of total proteins from 4.2 picomole to 13 femtomole. It was identified that since the quantity ionized by laser in MALDI mass spectrometer is limited, MALDI mass spectrometer measures the intensity of parent ions as being small in comparison to the quantity of loaded sample in case where the sample is used in a great quantity as compared to the case where the sample is used in a small quantity, but the quantitative analysis through tandem mass spectrometry is irrelevant thereto. Further, since the isobaric labeling agents of the present invention provide strong quantitative signals, the samples can be quantitatively analyzed even in a quantity as little as 13 femtomole.

Figure 12:
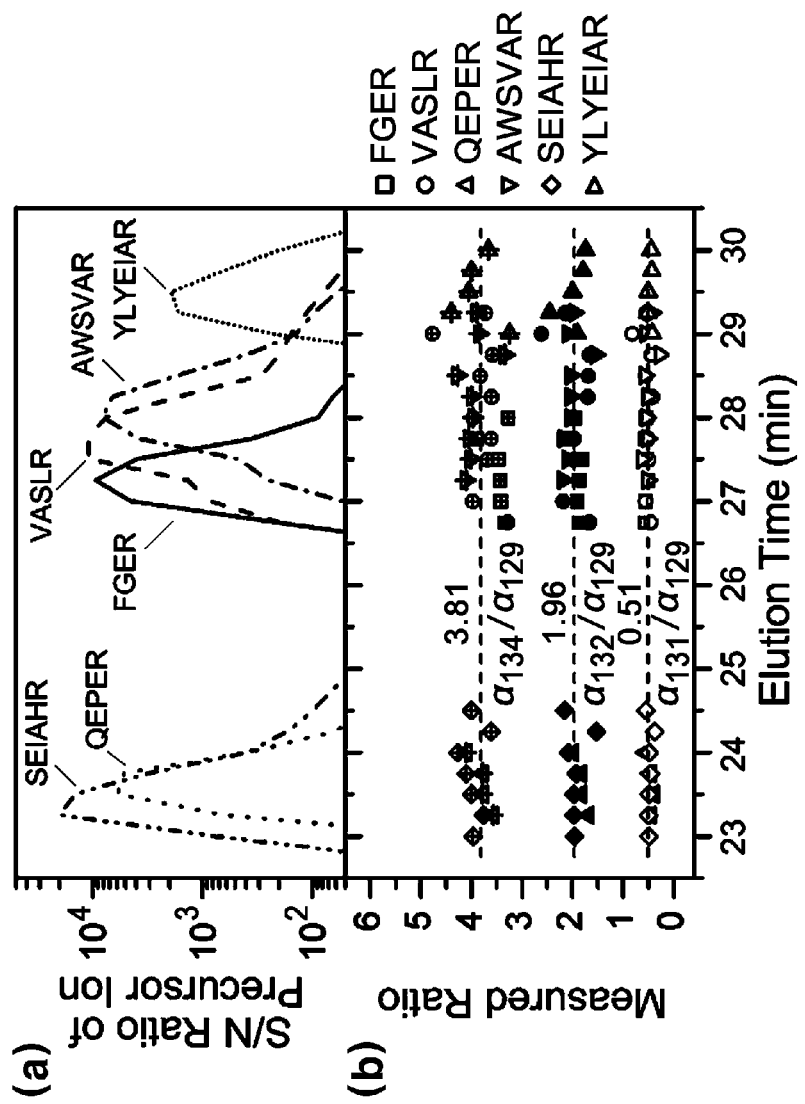
FIG. 12 shows the result of quantitative analysis of tryptic BSA labeled with the multiplexed isobar using liquid chromatography (LC) interconnected with MALDI mass spectrometer.
Figure 13:
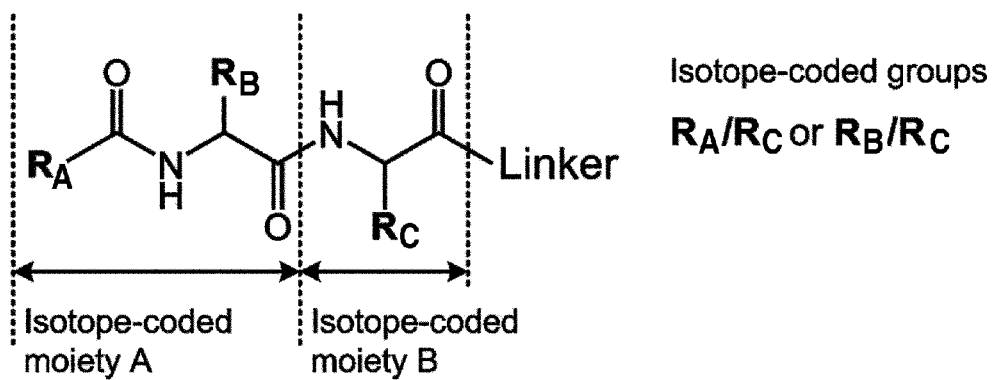
FIG. 13 schematically shows the chemical structure of the labeling agent of the present invention.
Figure 14A:
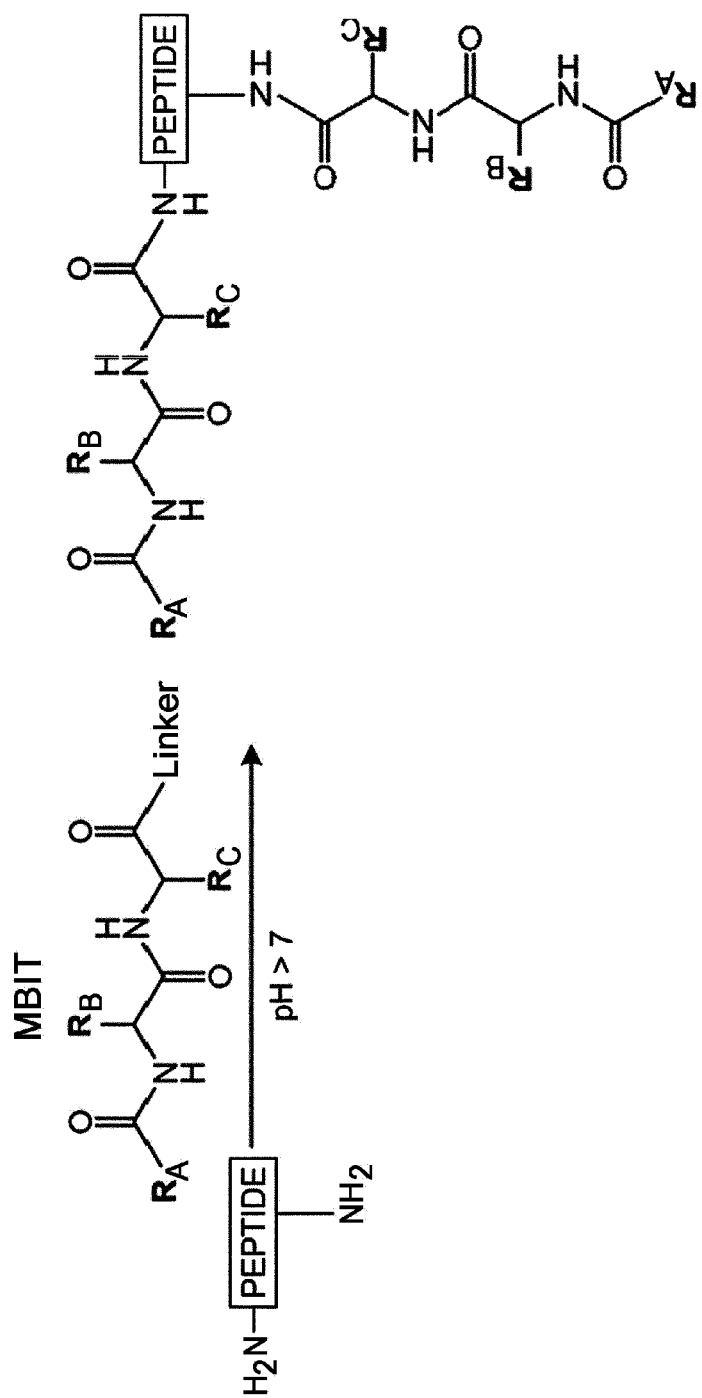
FIG. 14 schematically shows the coupling reaction of the labeling agent of the present invention with peptides and proteins.
Figure 14B:
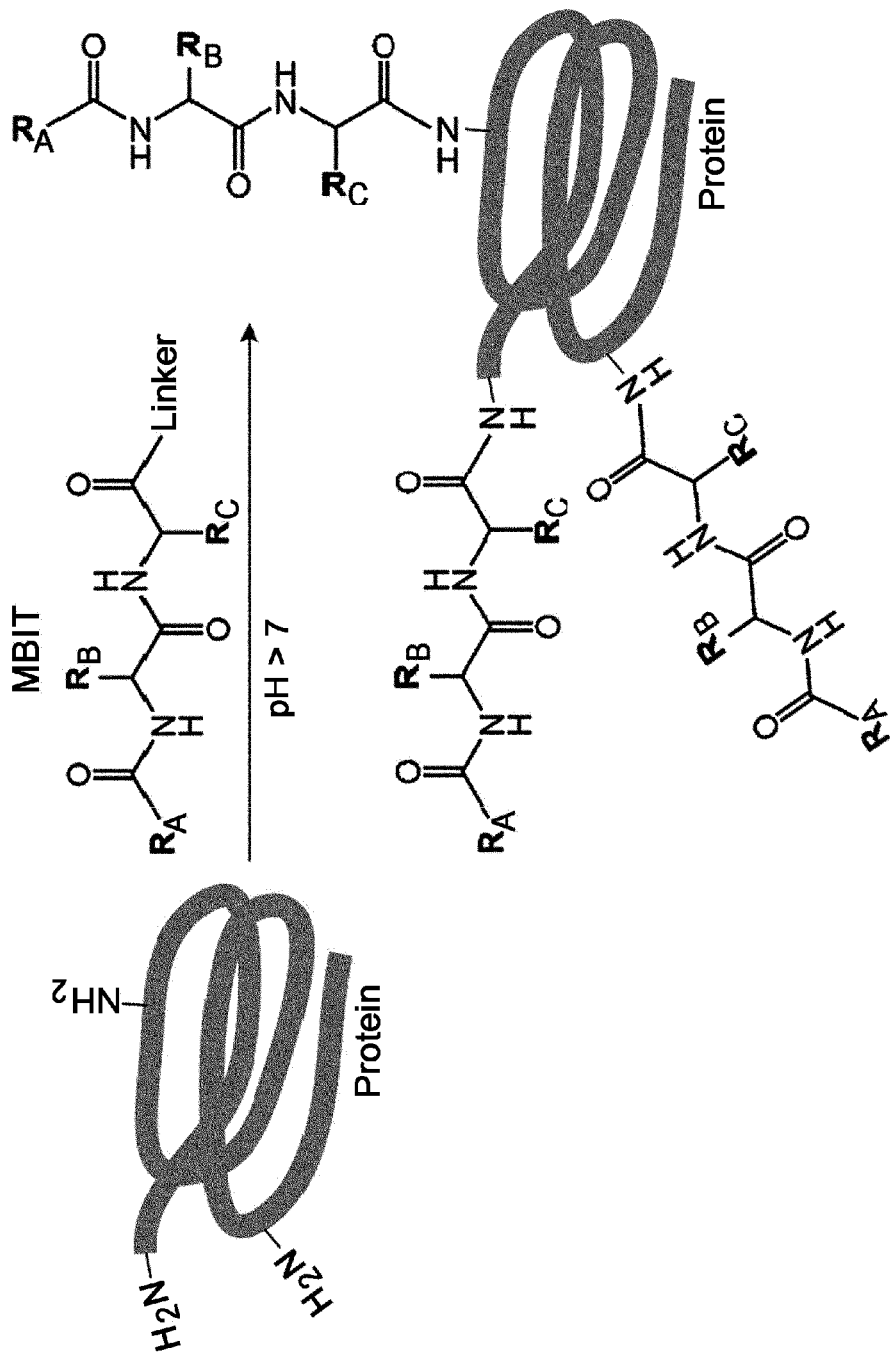
Figure 15:
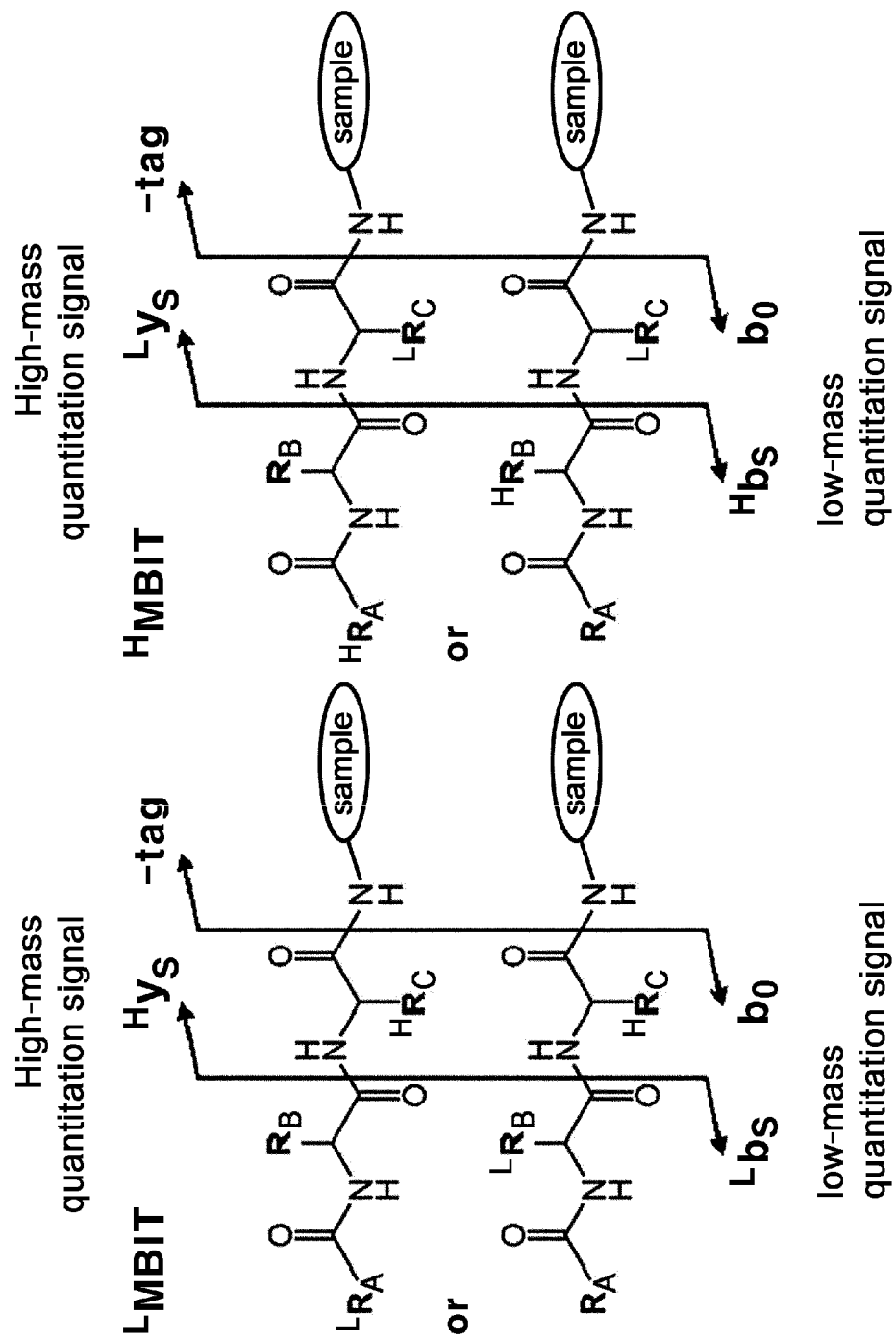
FIG. 15 schematically shows the kinds of the fragment ions which can be produced when the labeling agent coupled with amine of the analyte is decomposed in the course of tandem mass spectrometry.
Figure 16:
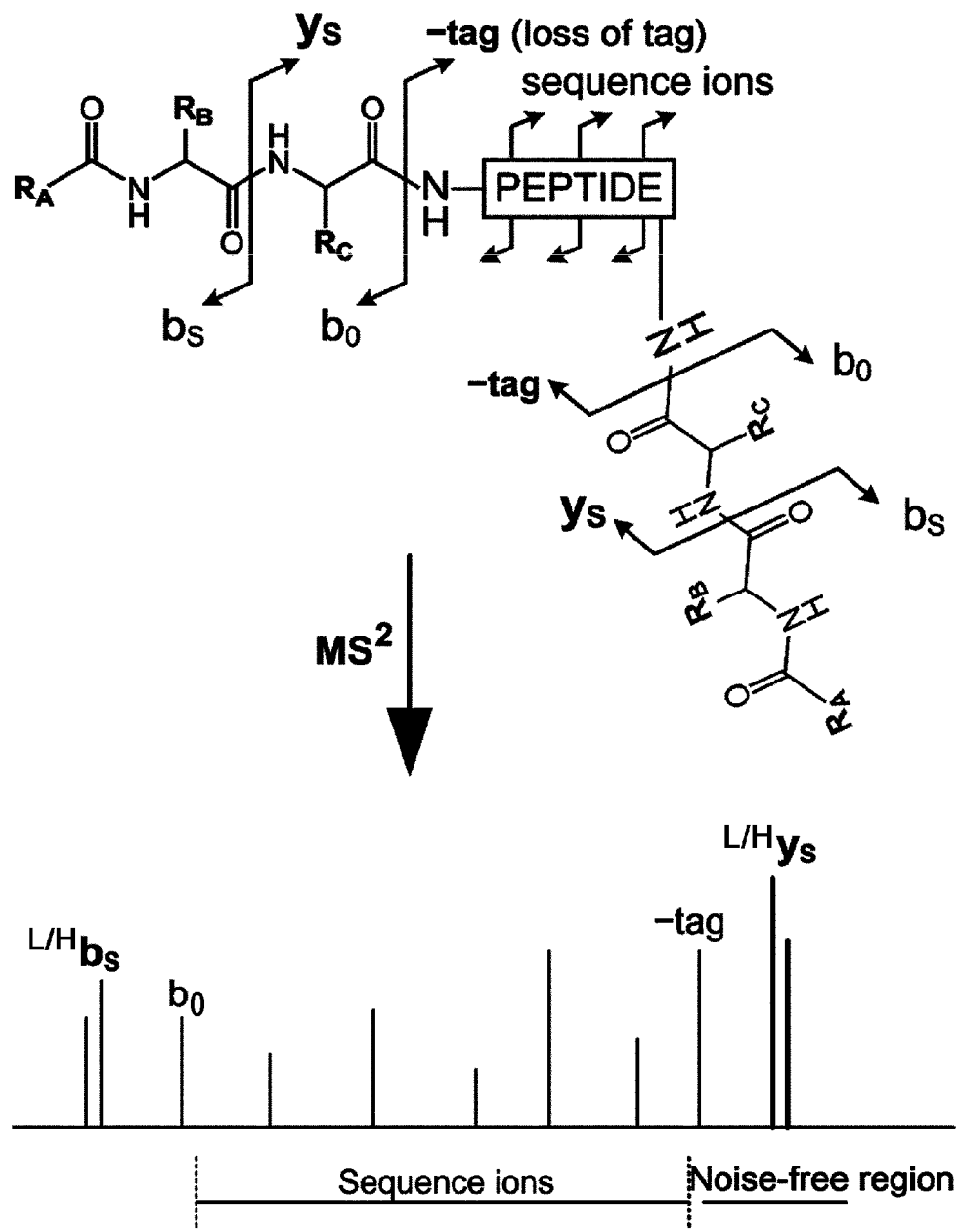
FIG. 16 shows the spectrum which can be theoretically produced from tandem mass spectrometry of peptides coupled with two or more labeling agents.

In addition, the result of quantitative analysis conducted by LC interconnected with MALDI mass spectrometry was shown in FIG. 12. FIG. 12(a) showed the intensity of parent ions eluted by LC and FIG. 12(b) showed the comparison of the quantity of quantitation signals measured in respective spots with the quantitation signal of tag $\alpha_{129}$. A total of 6 kinds of peptides (FGER, VASLR, QEPER, AWSVAR, SEIAHR, and YLYEIAR) were quantified through tandem mass spectrometry. Regardless of the kinds of peptides, respective isobaric labeling agents were used at a certain ratio (tag $\alpha_{129}:\alpha_{131}:\alpha_{132}:\alpha_{134}=1:0.51:1.96:3.81$). In addition, in case of the same peptides the quantitation signals were measured at the same ratio in the course of elution in LC. It means that peptides multilabeled with the isobars of the present invention were simultaneously moved on nanoLC, and therefore, the quantification could be accurately accomplished only with the effluent at a specific point. Further, as can be observed using the model peptides, it was identified that the ratio of quantitation signals as observed was not affected by a total quantity of the sample.

Example 2

Example 2-1

Preparation of Labeling Agents

With reference to Korean Patent Publication Nos. 10-2010-0009466 and 10-2010-0009479, and International Patent Publication No. WO 10/008,159, the labeling agents of formula 2 according to the present invention were prepared.

First, the labeling agents wherein the isotope encoding groups $R_A$ and $R_C$ are methyl ($CH_3$ or $CD_3$) and the mass controlling group $R_B$ is the side chain of valine (Val), glutamine (Gln), histidine (His), phenylalanine (Phe), and arginine (Arg) were prepared. For convenience, those having the side chain of valine (Val), glutamine (Gln), histidine (His), phenylalanine (Phe), and arginine (Arg) as the mass controlling group were designated as Val-tag, Gln-tag, His-tag, Phe-tag, and Arg-tag, respectively. In addition, the labeling agent wherein the isotope encoding groups $R_A$ and $R_C$ are ethyl ($C_2H_5$ or $C_2D_5$) and the mass controlling group $R_B$ is methyl was prepared. For convenience this was designated as Ethyl-tag.

Example 2-2

Preparation of Coupled Product 3 kinds of the model peptides LISFYAGR, LISFYAGK and YGGFLK were coupled with Val-, Gln-, His-, Phe-, Arg-tag and Ethyl-tag as the labeling agents prepared in Example 2-1 above. In addition, two samples of protein mixture composed of bovine serum albumin, myoglobin, and ubiquitin mixed in quantities different from each other were prepared. The mixed sample A was prepared in the concentrations of 4 mg/mL, 2 mg/mL, and 0.2 mg/mL of bovine serum albumin, myoglobin, and ubiquitin, respectively, and the mixed sample B was prepared in the concentrations of 2 mg/mL, 0.5 mg/mL, and 0.4 mg/mL of bovine serum albumin, myoglobin, and ubiquitin, respectively. Each of the mixed samples A and B was enzymatically decomposed with trypsin and the mixed samples A and B were then coupled with $^L$MBIT and $^H$MBIT, respectively. For this, Gln-tag was used as the MBIT label. For the methods for coupling the peptide samples with MBIT, Korean Patent Publication Nos. 10-2010-0009466 and 10-2010-0009479, and International Patent Publication No. WO 10/008,159 were referred to.

The model peptides coupled with the labeling agents were treated with ZipTip-$C_{18}$ (Millipore) to remove the salt and then finally prepared in the state dissolved in the solution wherein acetonitrile and water were mixed at the volume ratio of 1:1 in the concentration of 5M, respectively, and 0.5% formic acid was added. The mixed samples A and B coupled with the labeling agents were mixed at the volume ratio of 1:1, subjected to vacuum to completely remove the solvent, and then prepared in the state dissolved in the aqueous solution supplemented with 0.5% formic acid.

Example 2-3

Quantitative Analysis

The quantitative analysis was conducted using the coupled product of the above Example 2-2 as follows.

As the mass spectrometers for the quantitative analysis of the coupled product of the model peptides and MBIT as disclosed in the above Example 2-2, Esquire HCT product from Bruker or LTQ Velos from Thermo was used as electrospray ionization quadrupole ion trap equipments. 100 μL of the sample solution was loaded in a syringe pump, and then transported to electrospray tip at the flow rate of 1 μL/min. The electrospray was accomplished under the voltage of 4 kV. To measure one spectrum for one cycle, the sample ions were collected within the ion trap for the maximum 200 ms and subjected to mass spectrometry. The repeated measurement of the maximum 250 cycles for one minute was conducted.

As the mass spectrometer for the quantitative analysis of the coupled product of the mixed sample A and B and MBIT as disclosed in the above Example 2-2, LTQ XL from Thermo was used as electrospray ionization quadrupole ion trap equipment interconnected with liquid chromatography. The sample solution was electrospray ionized by passing through liquid chromatography at the flow rate of 0.3 μL/min. For this, the electrospray was accomplished under the voltage of 2 kV. The spectrums of mass spectrometry and tandem mass spectrometry were obtained for respective peptides eluted from liquid chromatography per 0.2 second.

1) Result of Mass Spectrometry for LISFYAGR and LISFYAGK Coupled with Respective Val-, Gln-, His-, Phe-, and Arg-Tag The quantitative analysis for LISFYAGR and LISFYAGK coupled with respective Val-, Gln-, His-, Phe-, and Arg-tag was conducted, and the result thereof was shown in FIG. 17.

Figure 17A:
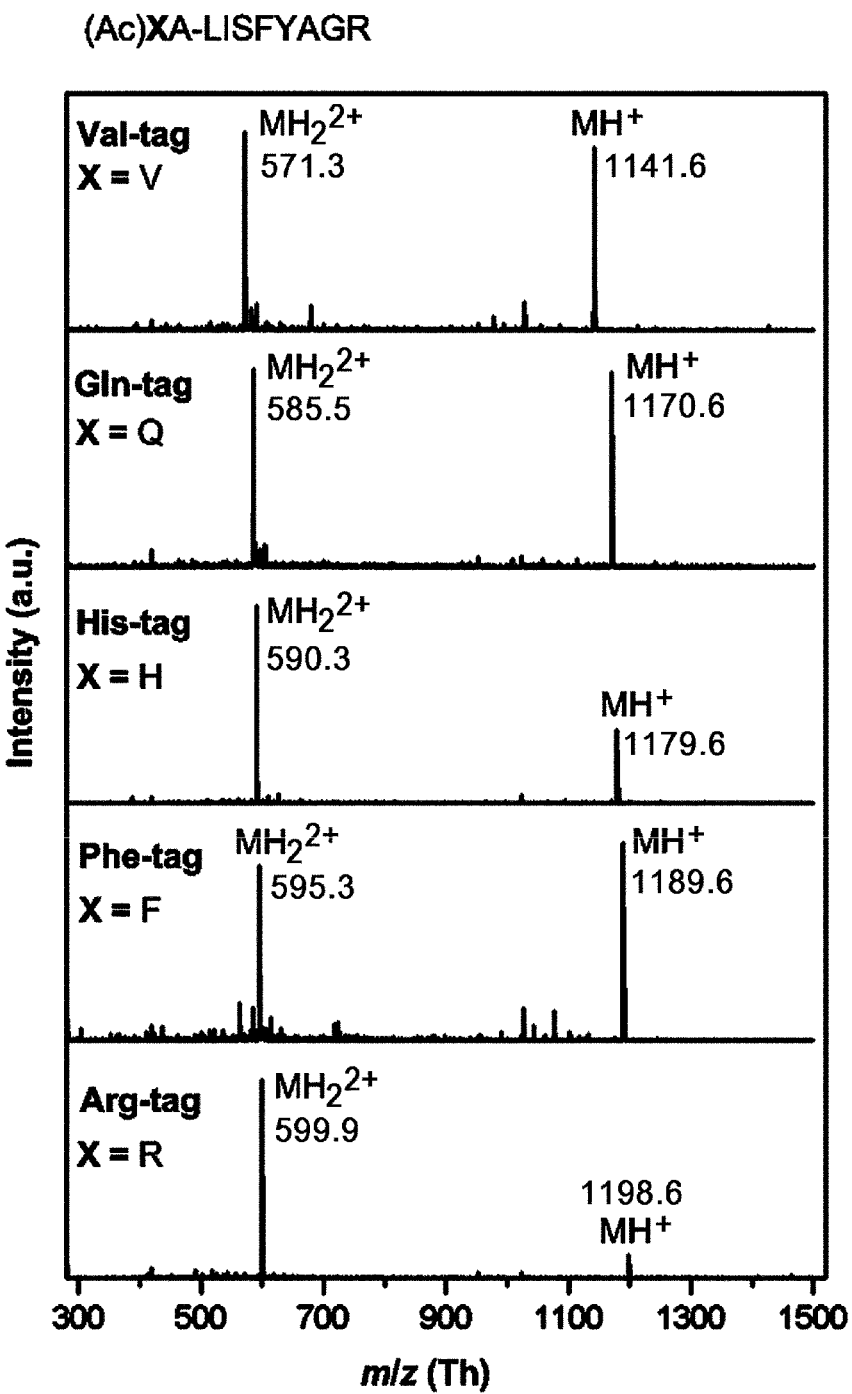
FIG. 17 shows the electrospray ionization (ESI) mass spectra of each of 2 kinds of the model peptides coupled with the labeling agent according to one example of the present invention.
Figure 17B:
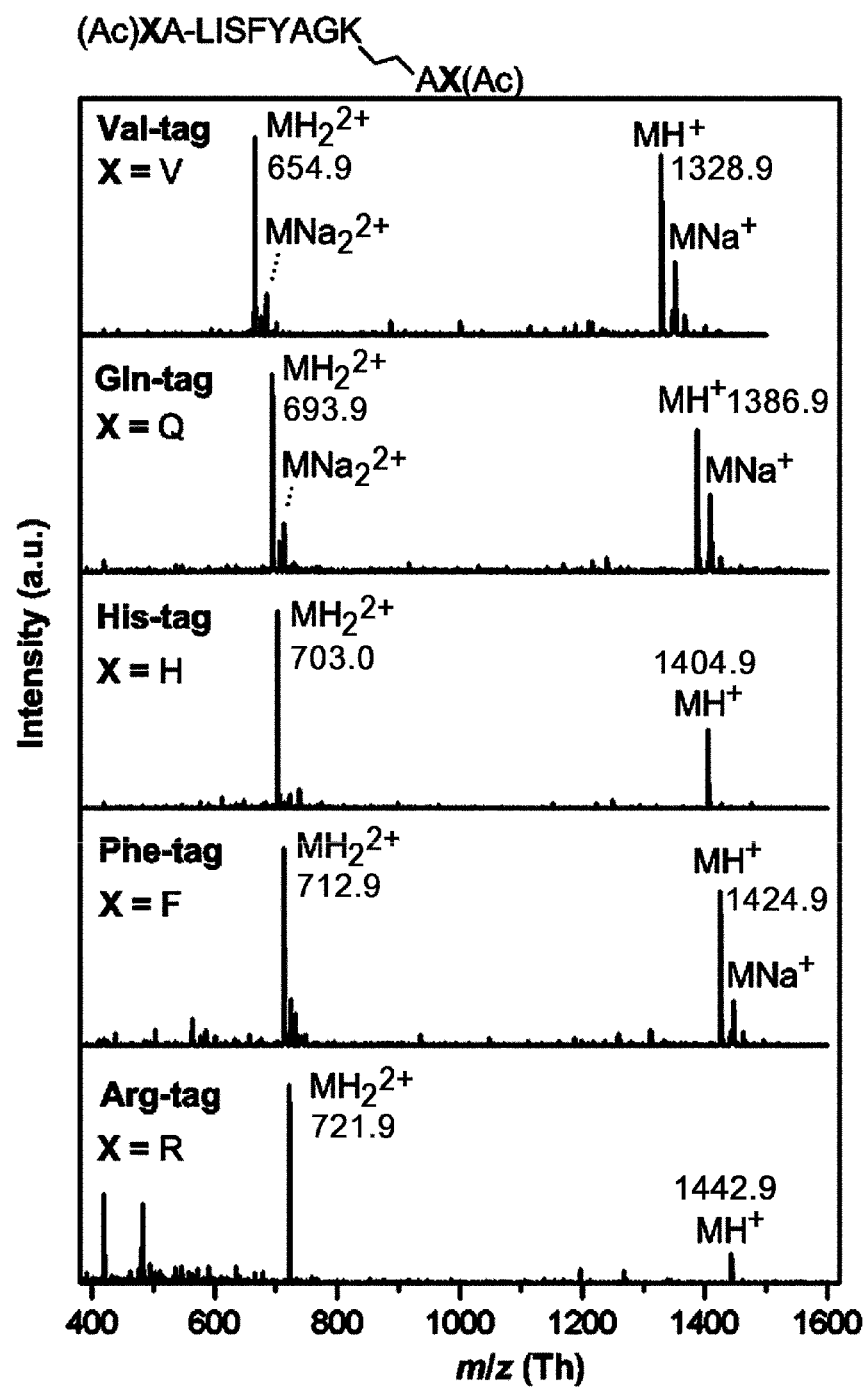
Figure 18A:
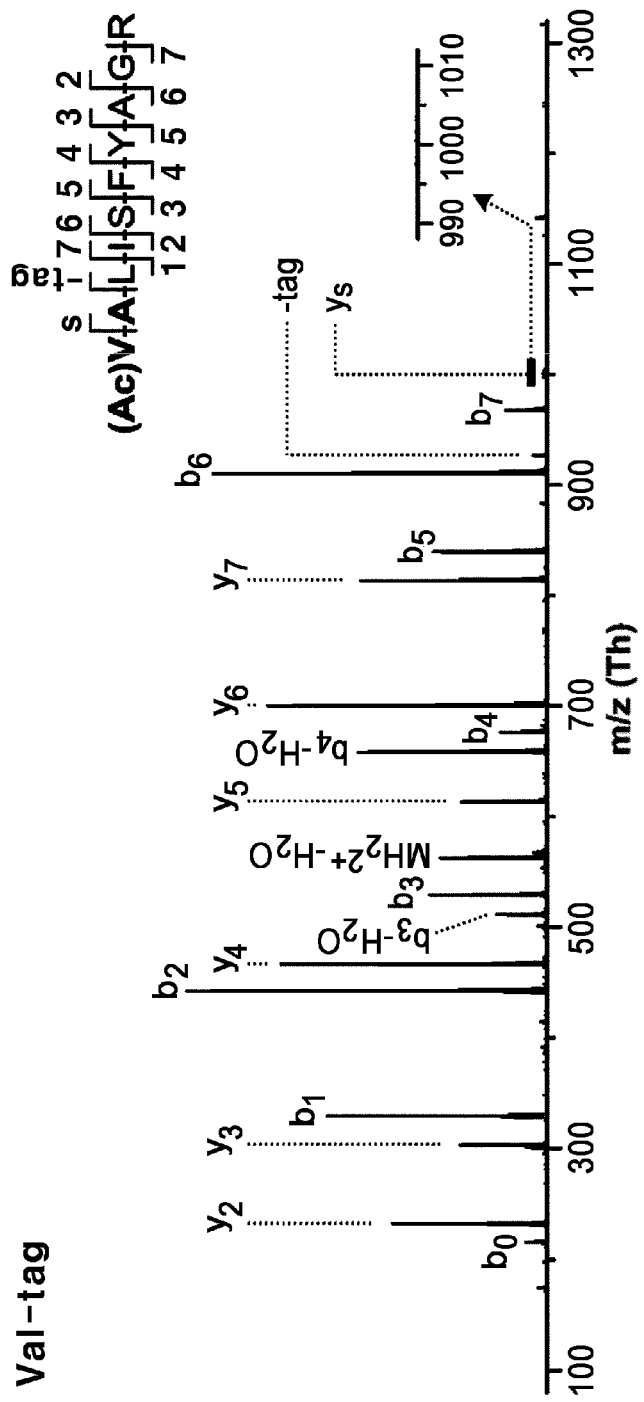
FIG. 18 shows the tandem mass spectra obtained by selecting ions ($MH_2^{2+}$) having +2 charge among parent ions formed from coupling peptide LISFYAGR having one amine on N-terminal with the labeling agent according to one example of the present invention in quadrupole ion trap, and then conducting resonant excitation collision-induced dissociation.
Figure 18B:
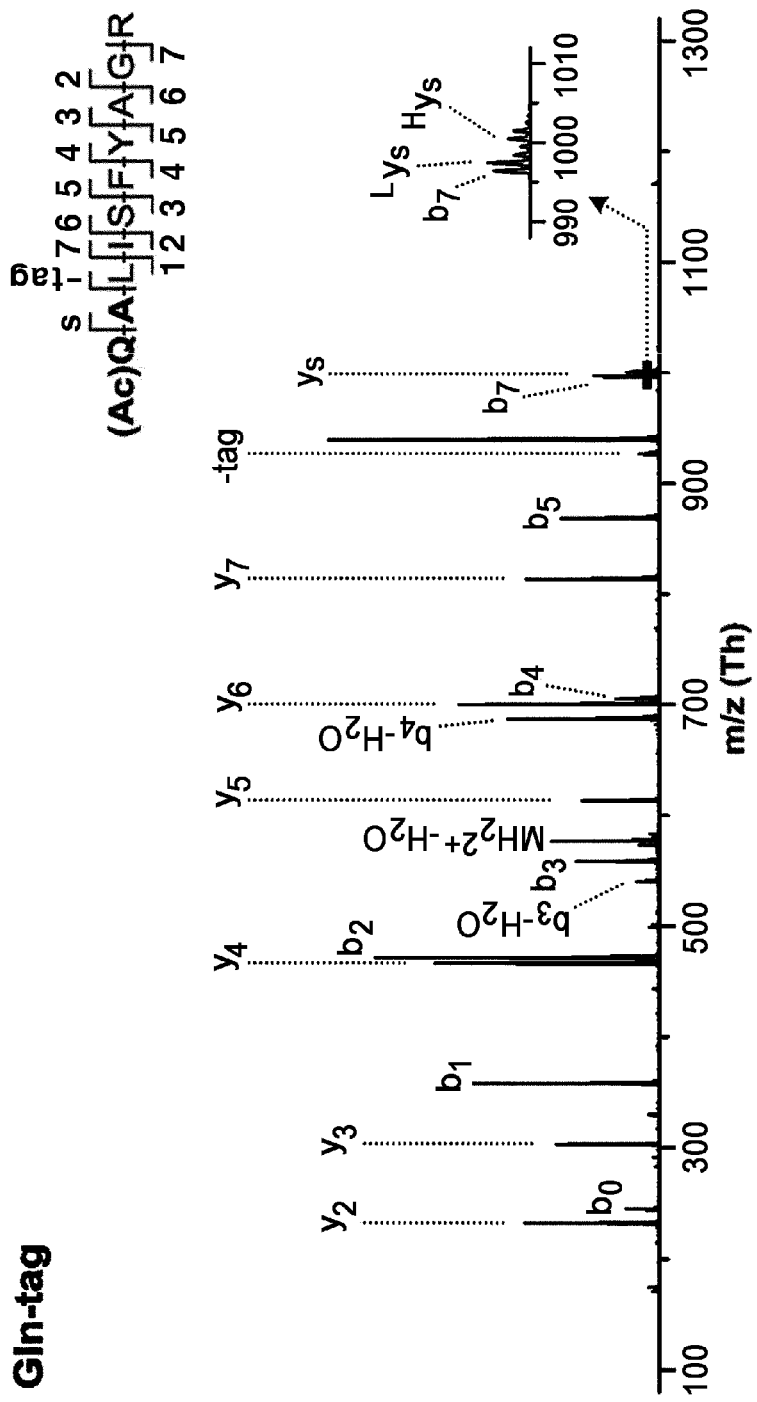
Figure 18C:
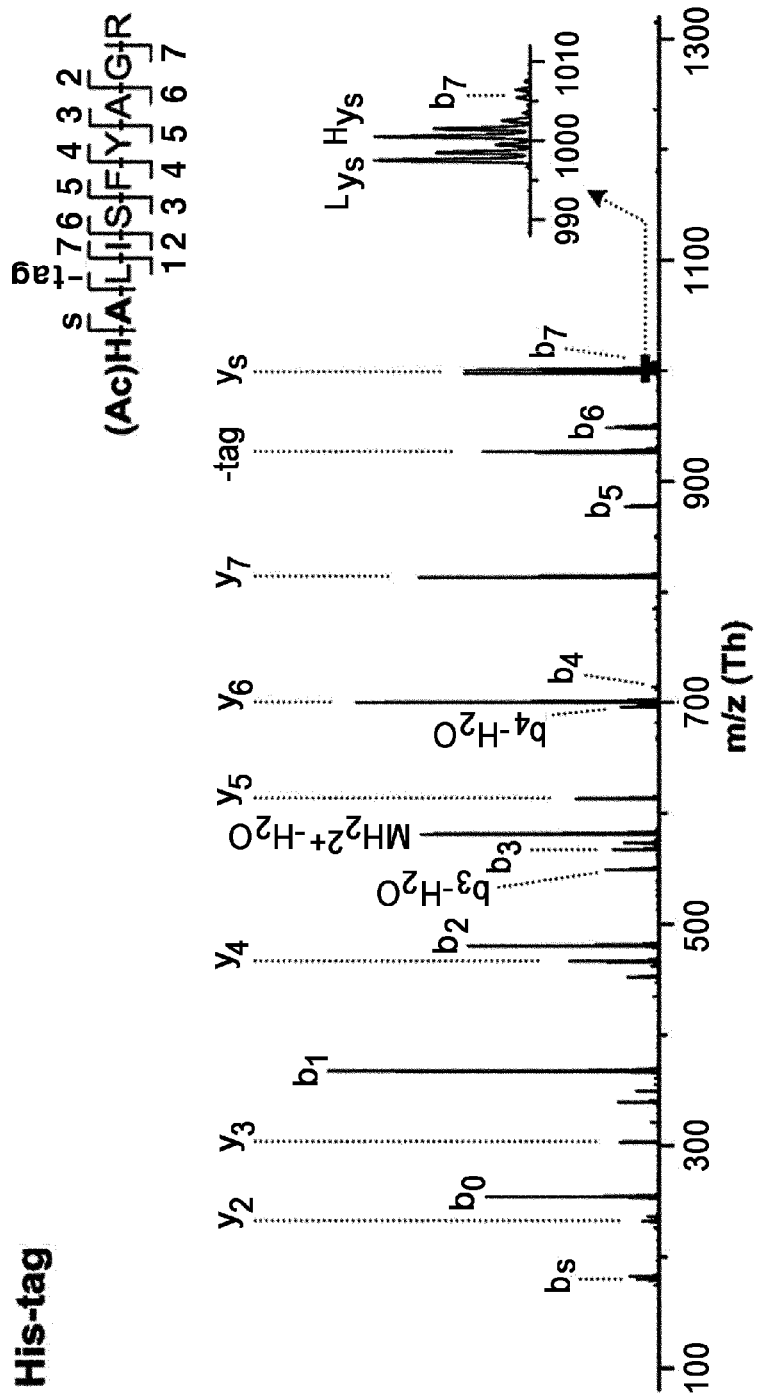
Figure 18D:
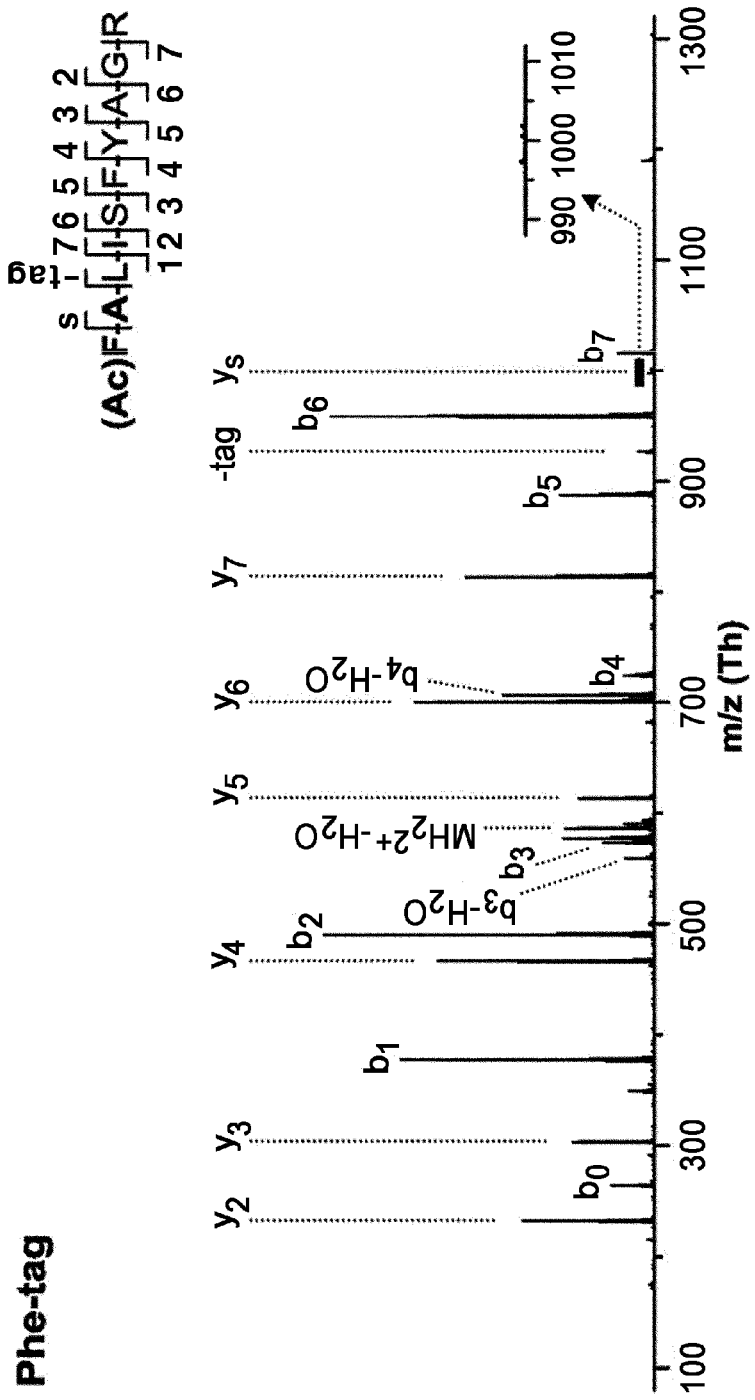
Figure 18E:
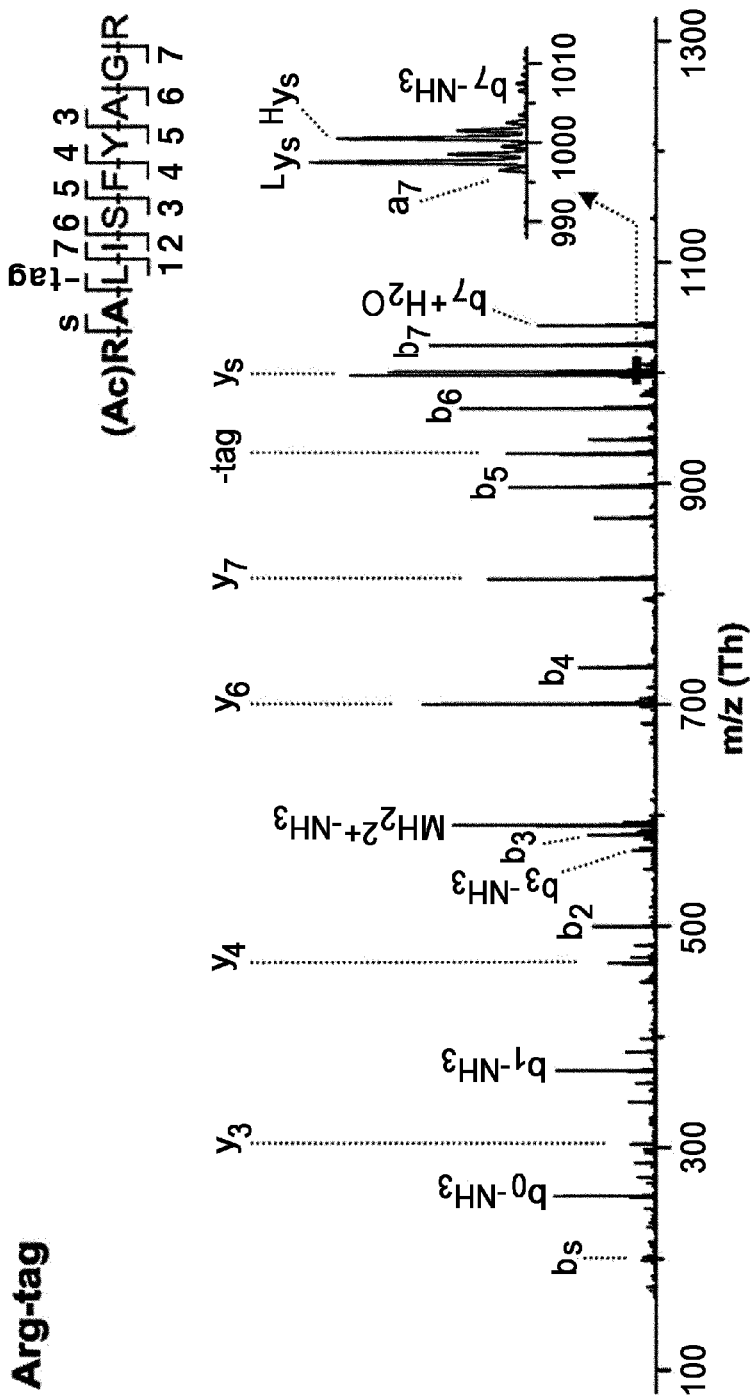
Figure 19A:
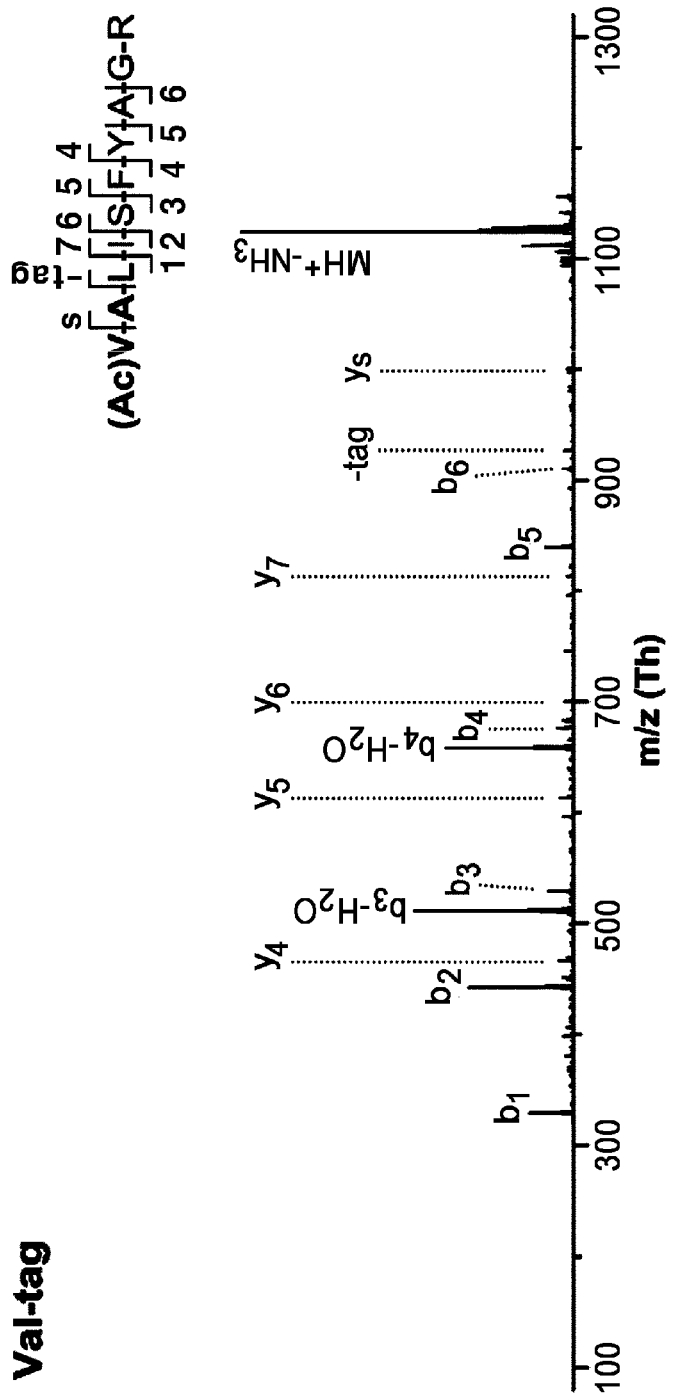
FIG. 19 shows the tandem mass spectra obtained by selecting ions ($MH^+$) having +1 charge among parent ions formed from coupling peptide LISFYAGR having one amine on N-terminal with the labeling agent according to one example of the present invention in quadrupole ion trap, and then conducting resonant excitation collision-induced dissociation.
Figure 19B:
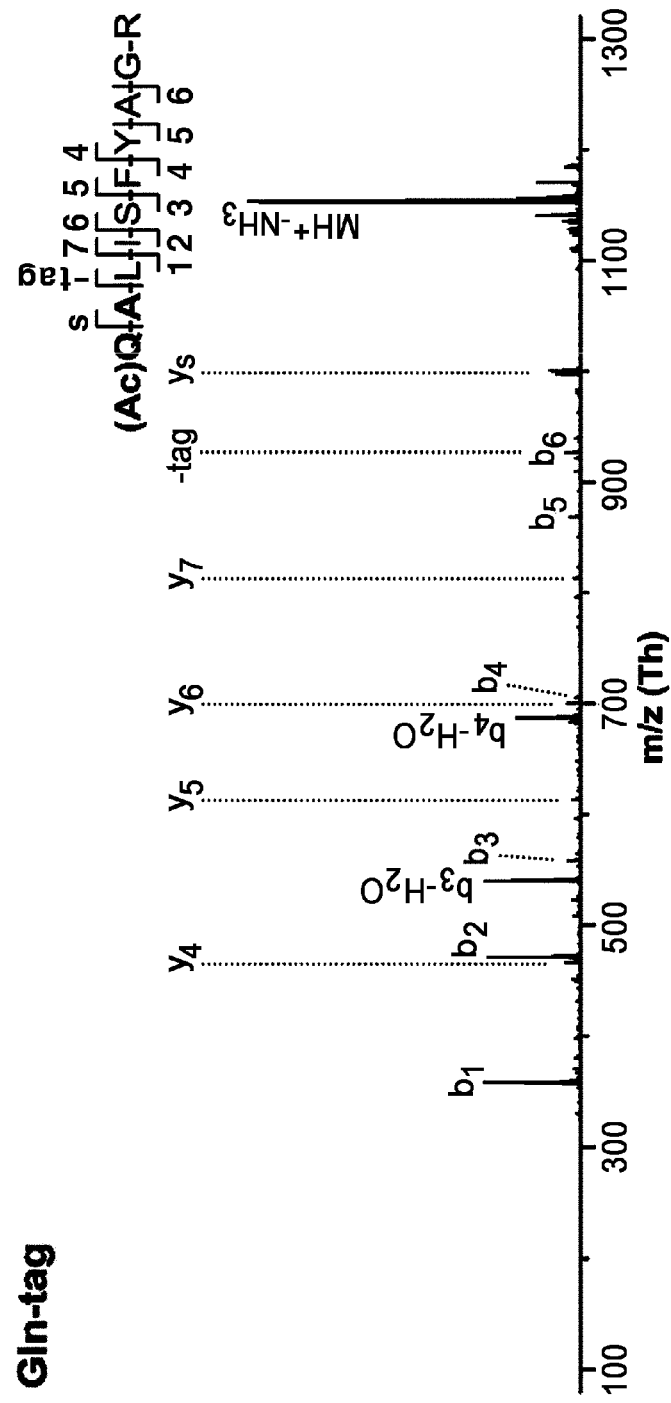
Figure 19C:
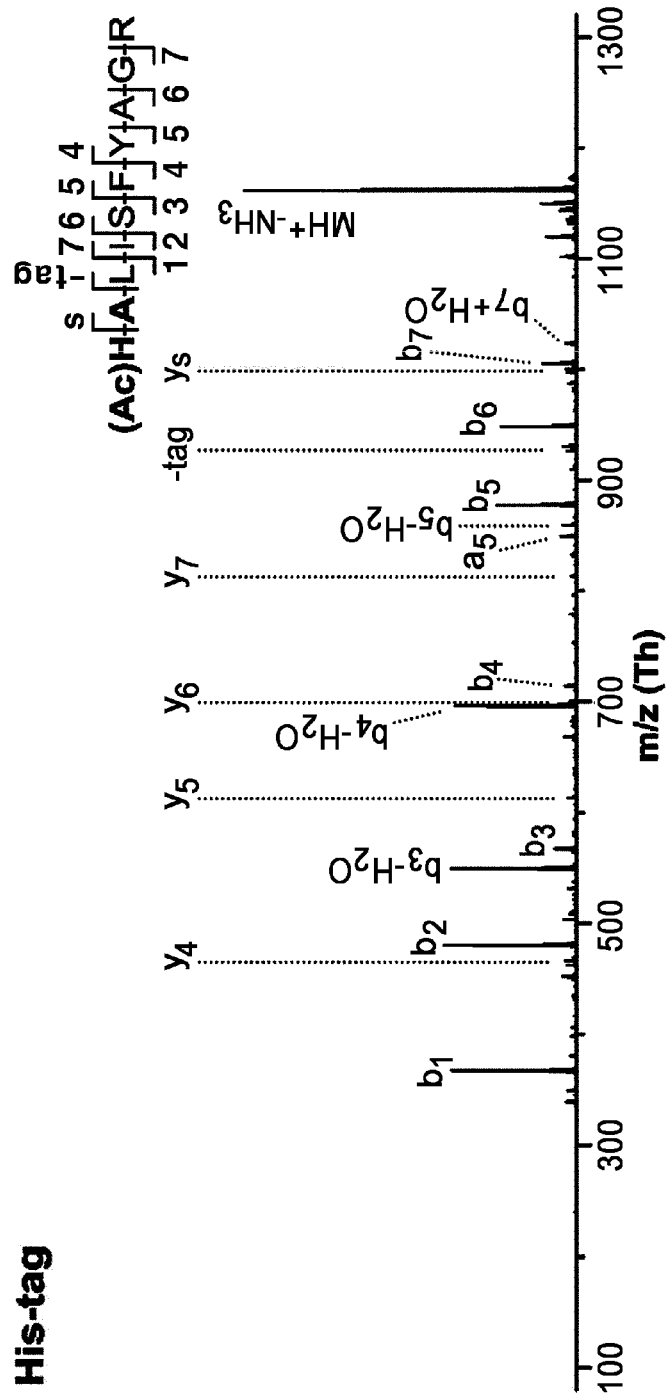
Figure 19D:
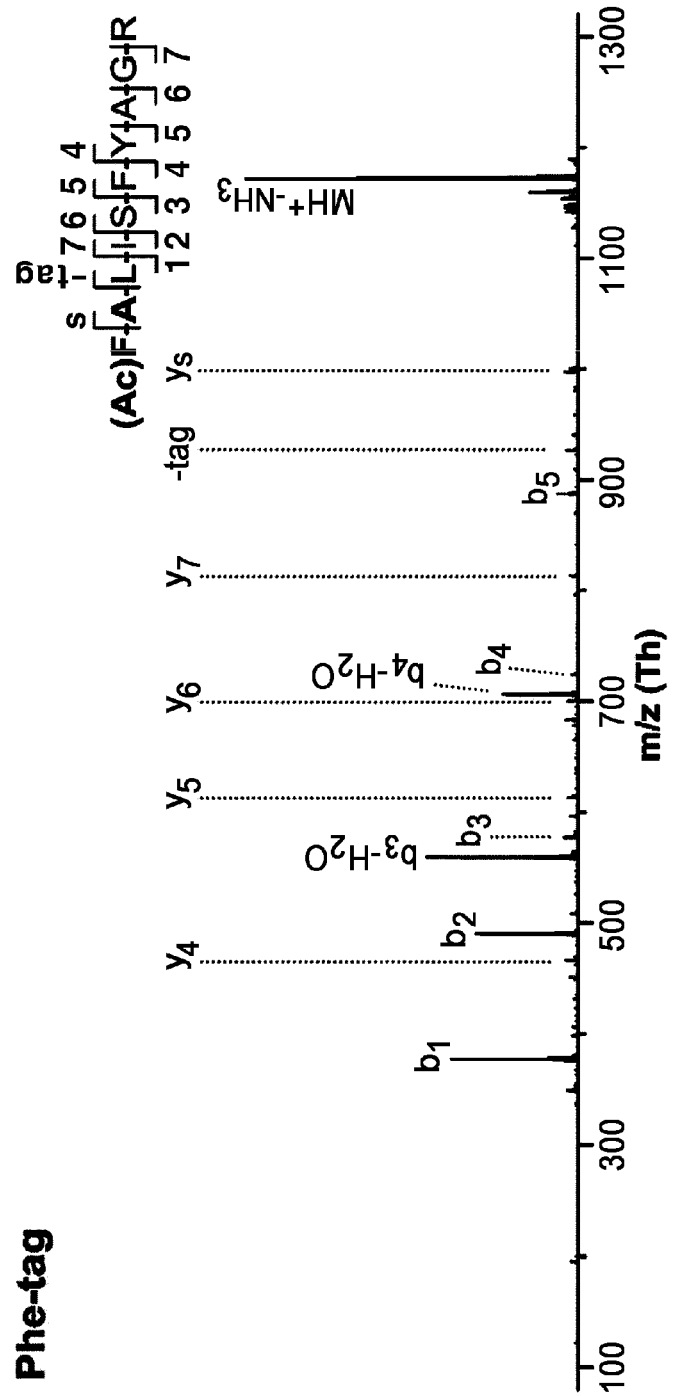
Figure 19E:
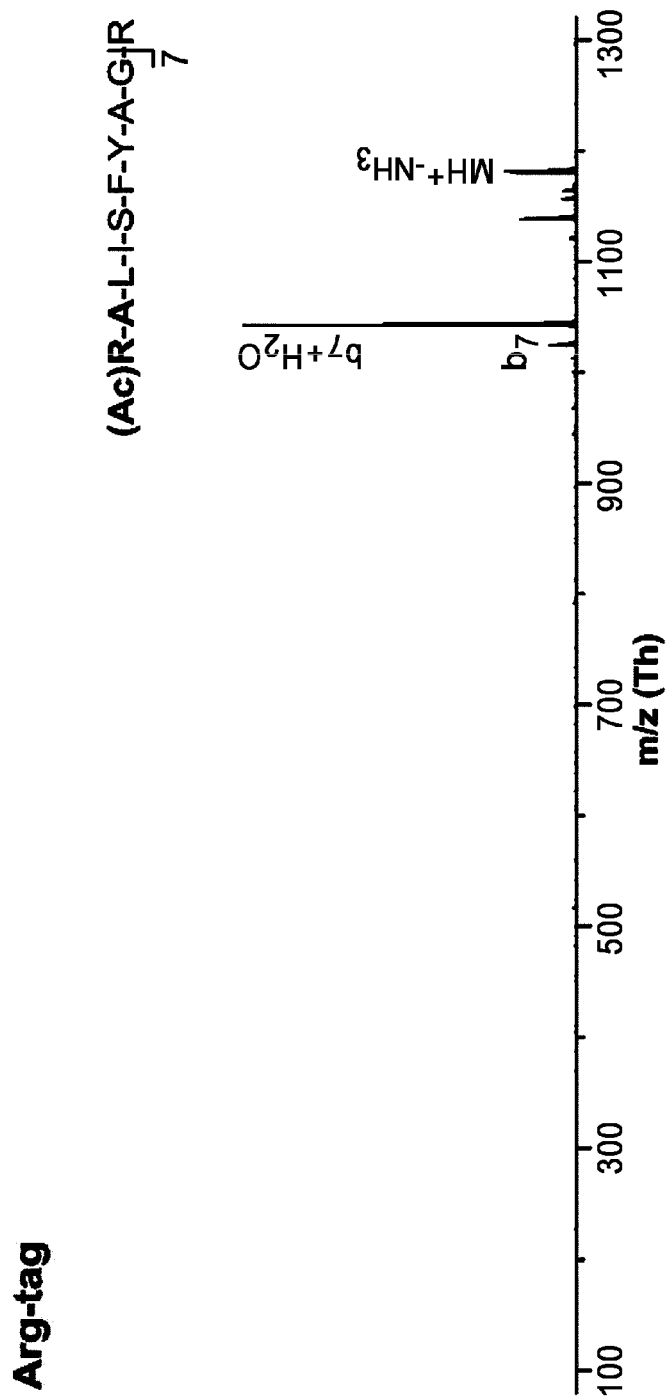
Figure 20A:
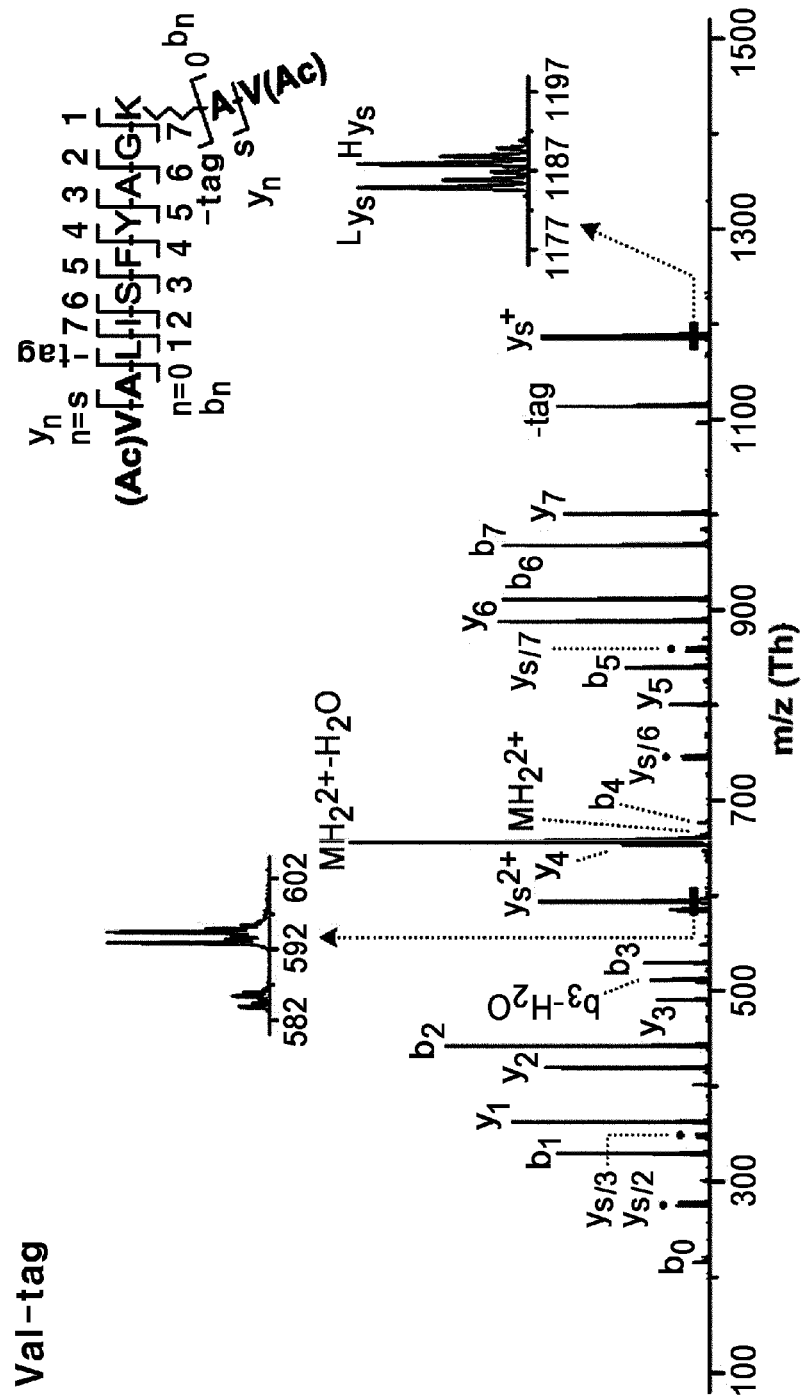
FIG. 20 shows the tandem mass spectra obtained by selecting ions ($MH_2^{2+}$) having +2 charge among parent ions formed from coupling peptide LISFYAGK having one amine on each of N-terminal and lysine side chain for a total of two amines, with the labeling agent according to one example of the present invention in quadrupole ion trap, and then conducting resonant excitation collision-induced dissociation.
Figure 20B:
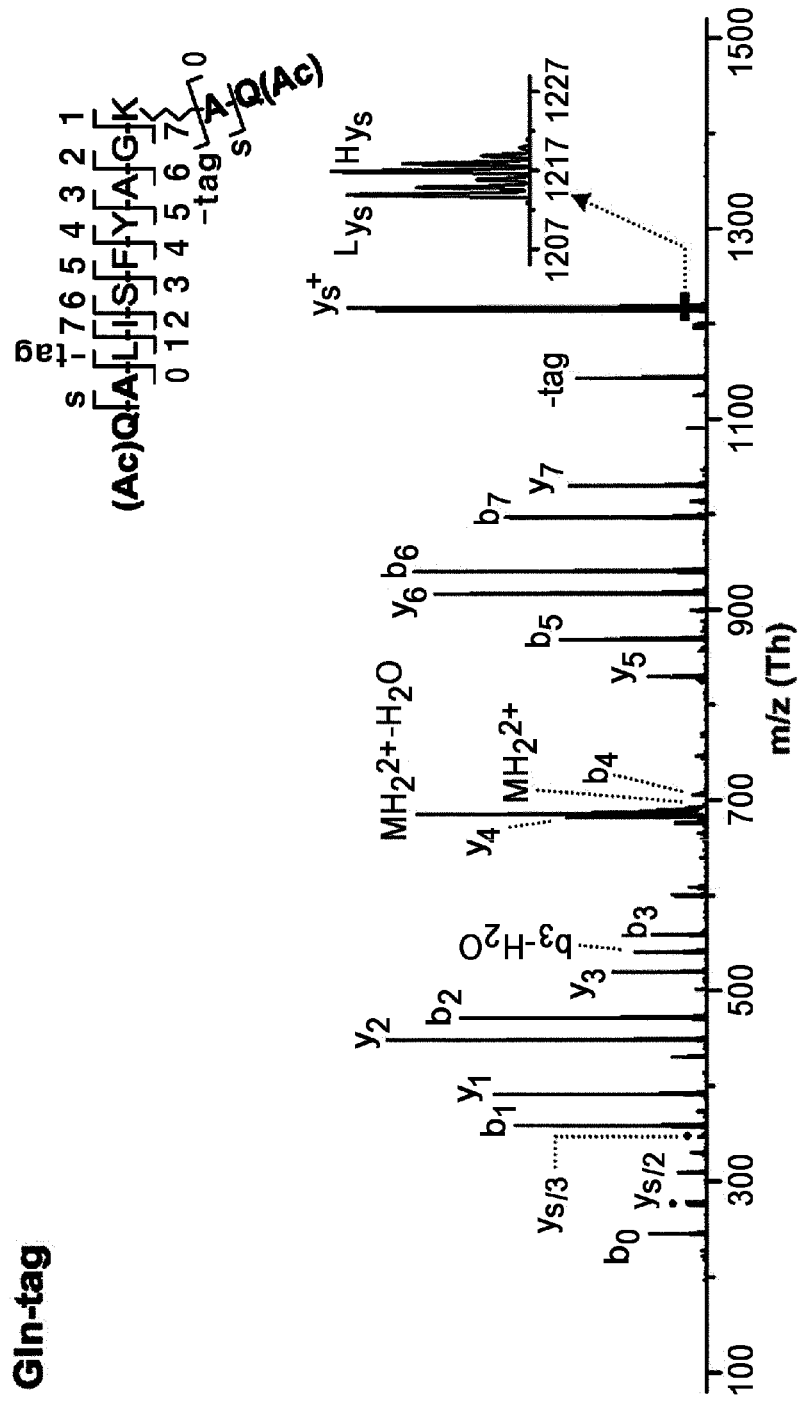
Figure 20C:
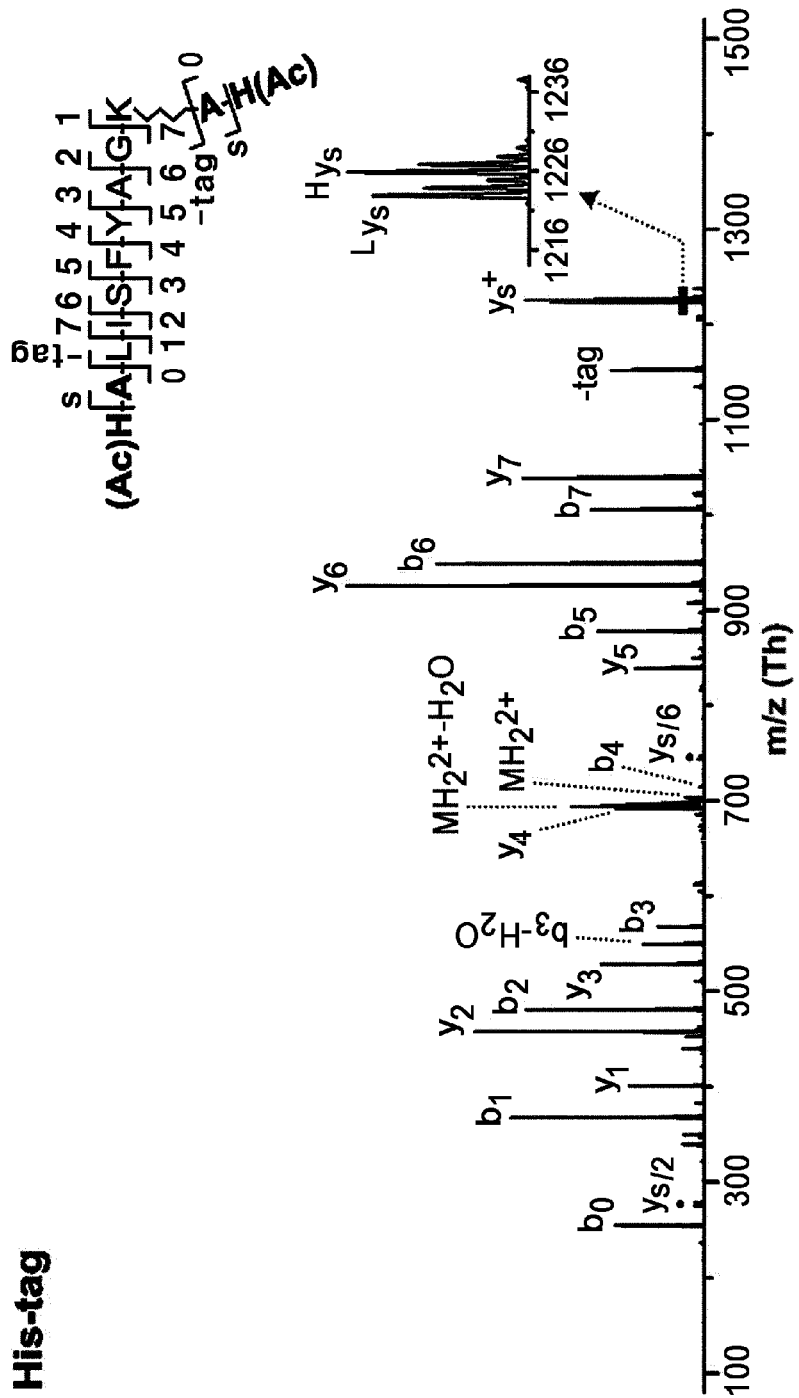
Figure 20D:
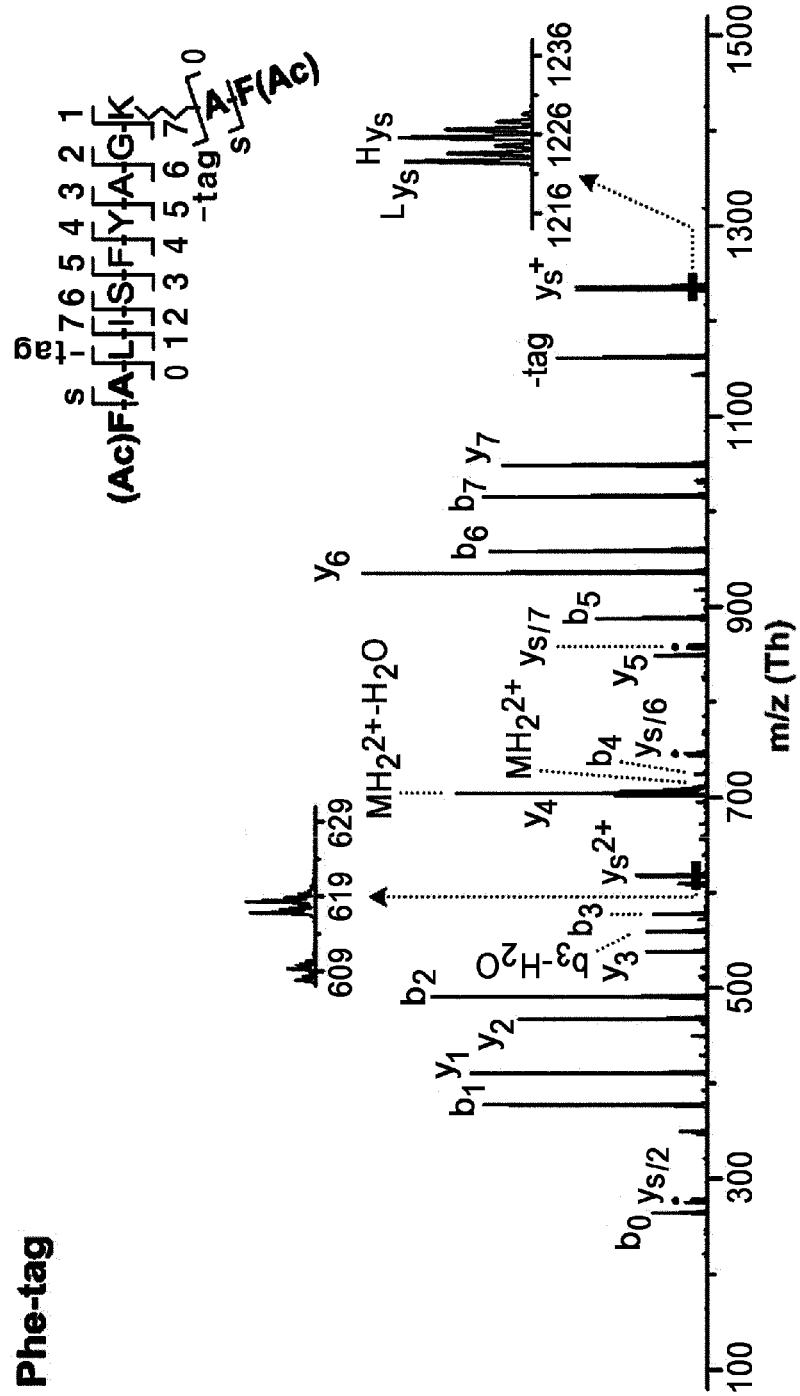
Figure 20E:
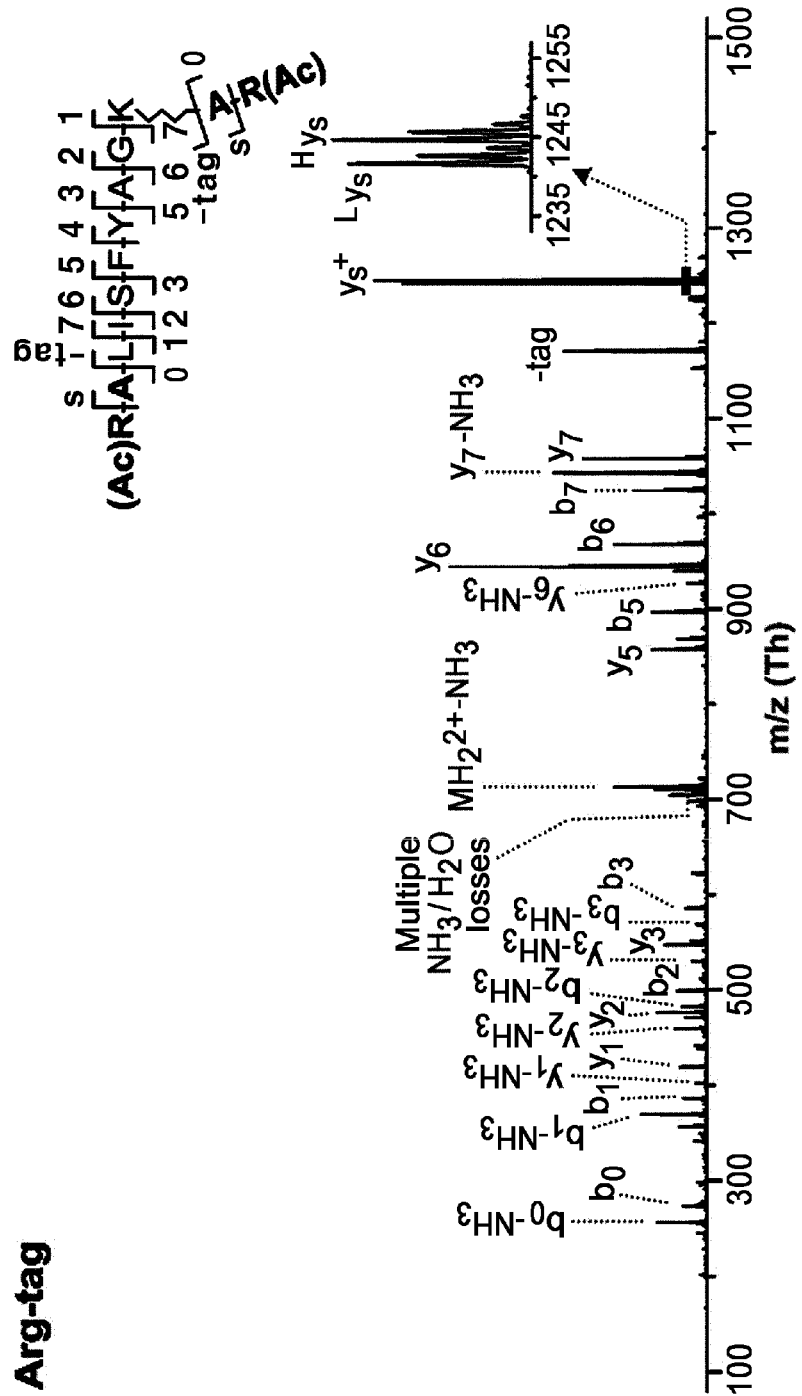
Figure 21A:
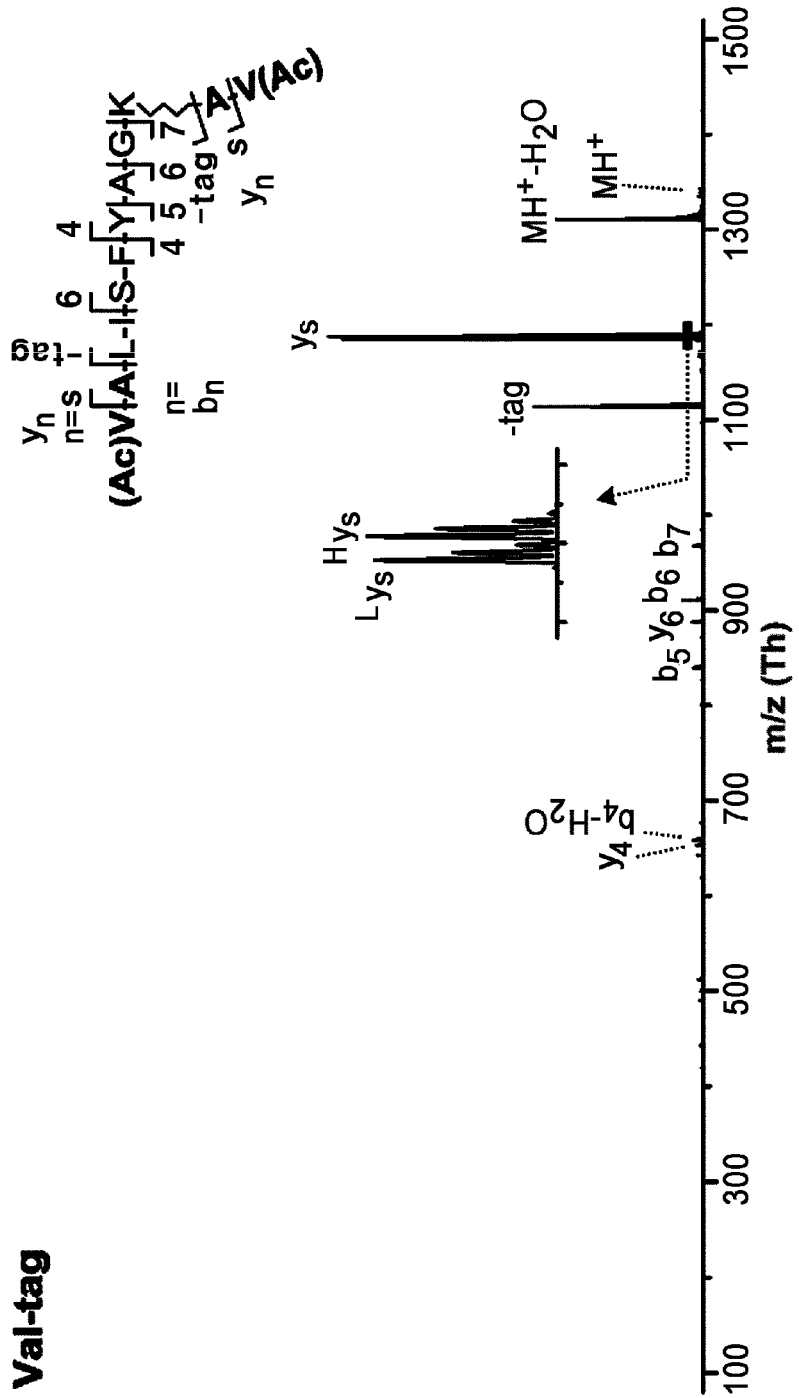
FIG. 21 shows the tandem mass spectra obtained by selecting ions ($MH^+$) having +1 charge among parent ions formed from coupling peptide LISFYAGK having one amine on each of N-terminal and lysine side chain for a total of two amines, with the labeling agent according to one example of the present invention in quadrupole ion trap and then conducting resonant excitation collision-induced dissociation.
Figure 21B:
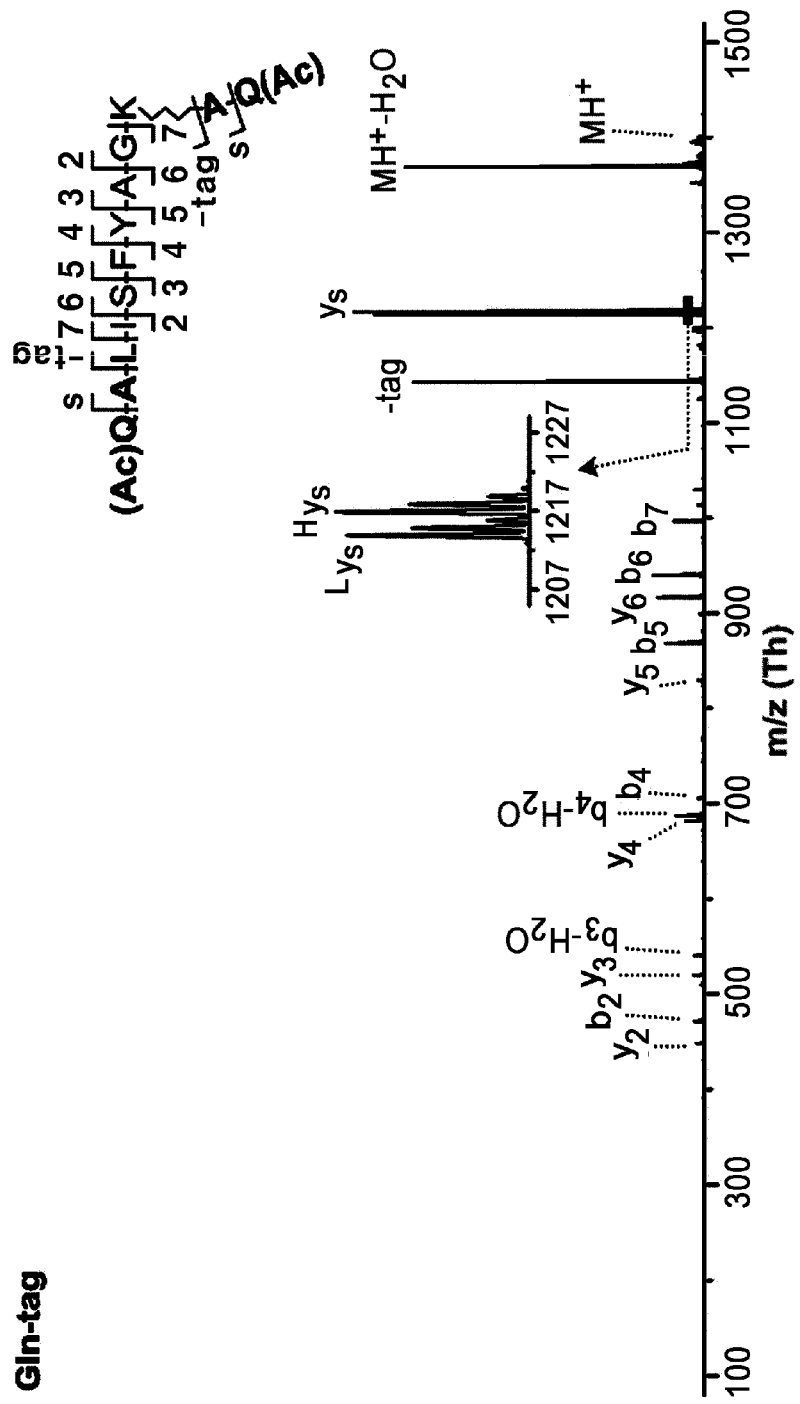
Figure 21C:
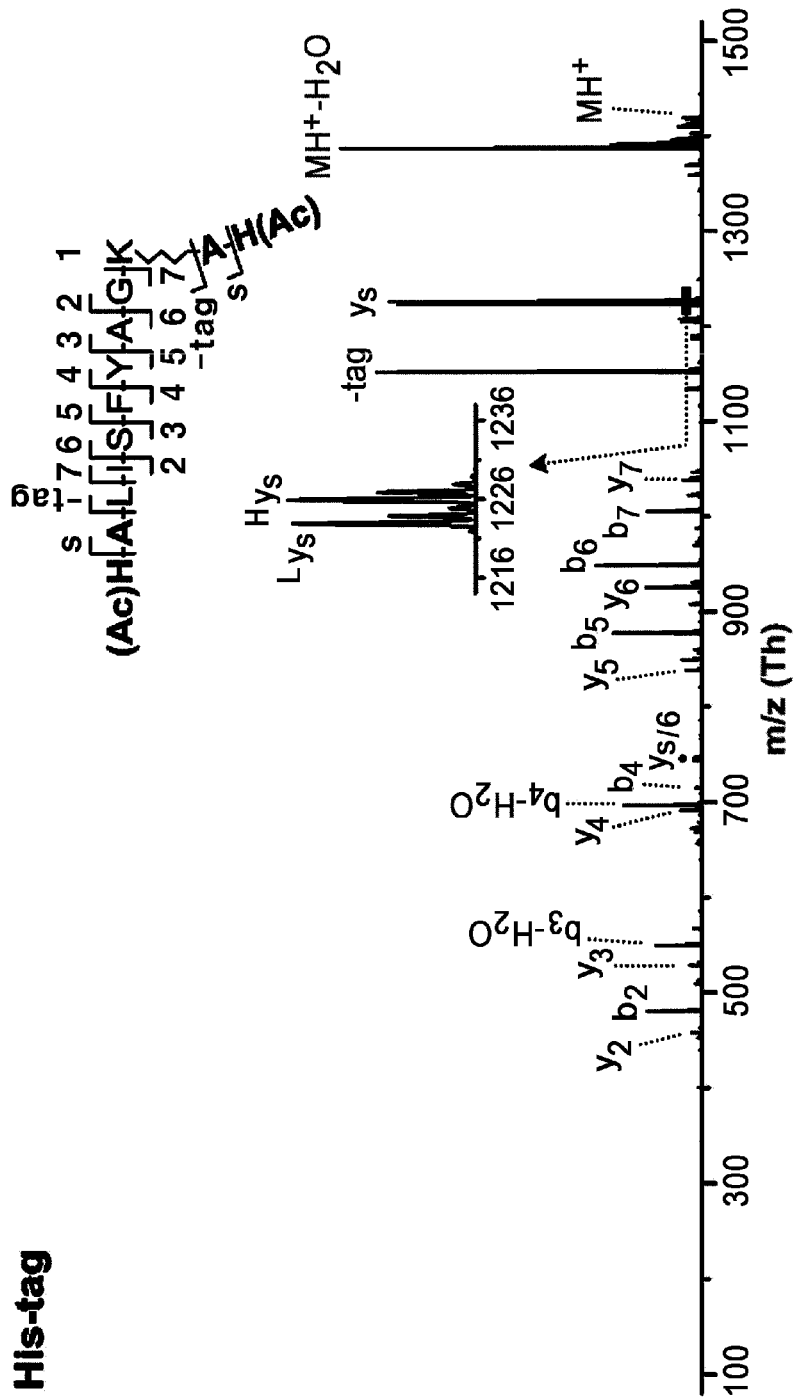
Figure 21D:
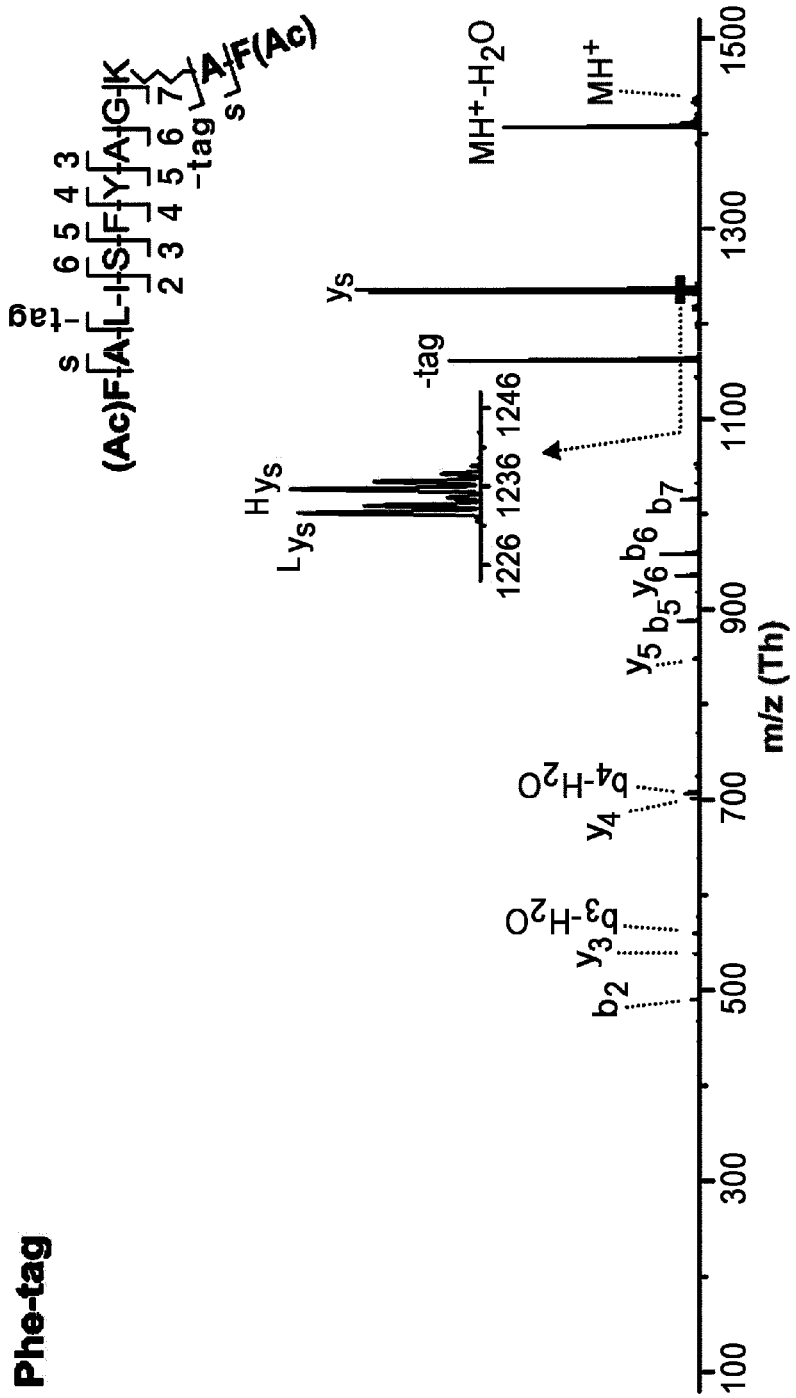
Figure 21E:
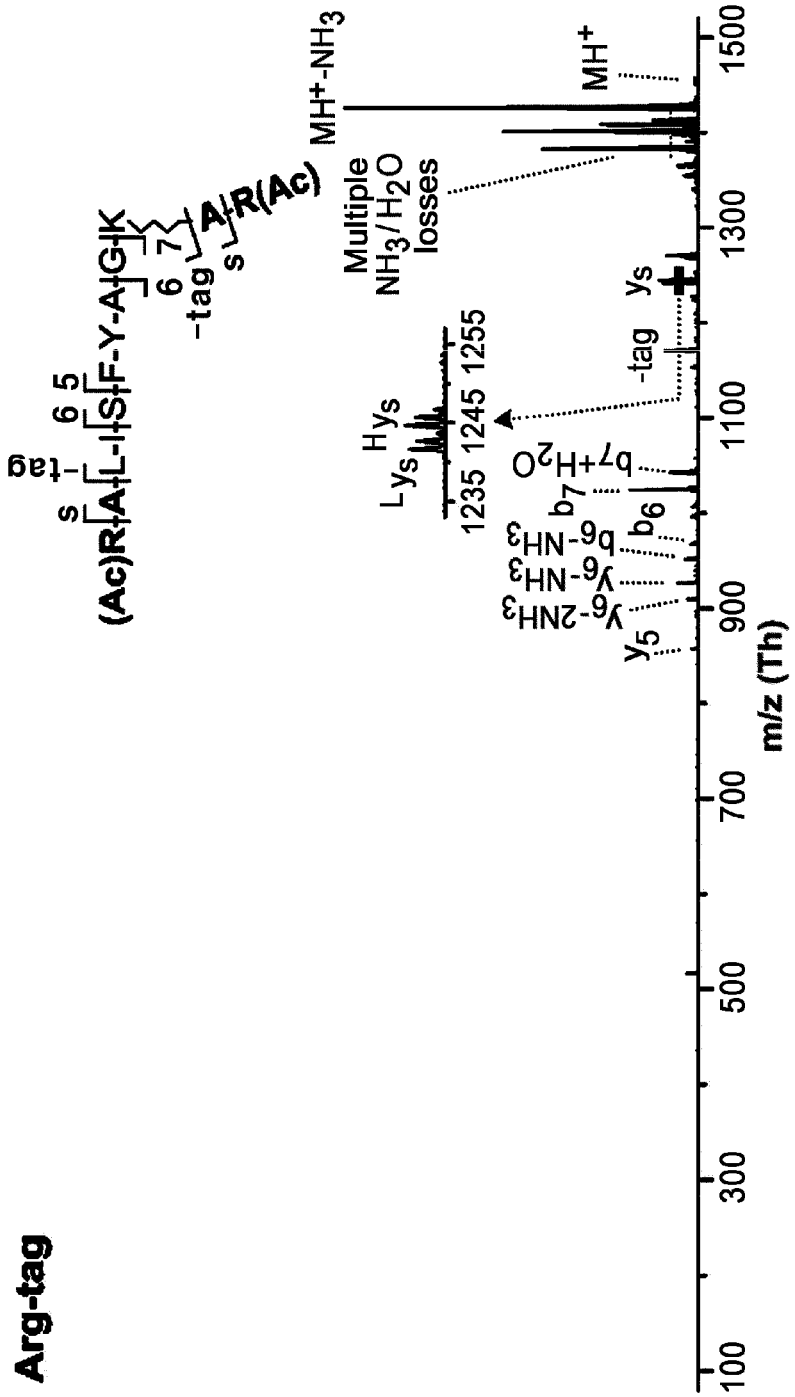

FIG. 17 showed the mass spectra obtained by coupling the model peptides LISFYAGR (FIG. 17(a)) and LISFYAGK (FIG. 17(b)) with Val-, Gln-, His-, Phe-, and Arg-tag followed by electrospray ionization and then quadrupole ion trap mass spectrometry. Peptide ions having +1 and +2 charge, were detected.

The original mass of LISFYAGR peptide was 925.5 Da and +1 and +2 charged ions ($NH^+$, $MH_2^{2+}$) having one or two protons as attached were detected at 926.5 Th, and 463.8 Th, respectively. When such peptides were coupled with the labeling agents, peptides were detected in the position corresponding to the mass increased by the mass of one respective label. When Val-, Gln-, His-, Phe-, and Arg-tag were coupled, respective +1 charged ions were detected at m/z 1141.6, 1170.6, 1179.6, 1189.6, and 1198.6 Th, and respective +2 charged ions were detected at m/z 571.3, 585.8, 590.3, 595.3, and 599.9 Th.

The original mass of LISFYAGK peptide was 897.5 Da, and +1 and +2 charged ions ($NH^+$, $MH_2^{2+}$) having one or two protons as attached were detected at 898.5 Th and 449.8 Th, respectively. When such peptides were coupled with the labeling agents, peptides were detected in the position corresponding to the mass increased by the mass of two respective labels. When Val-, Gln-, His-, Phe-, and Arg-tag were coupled, respective +1 charged ions were detected at 1328.9, 1386.9, 1404.9, 1424.9, and 1442.9 Th, and respective +2 charged ions were detected at m/z 654.9, 693.9, 703.0, 712.9, and 721.9 Th.

From the above results, it could be identified that LISFYAGR having one amine group was coupled with one labeling agent and LISFYAGK having two amine groups were coupled with two labeling agents.

2) Result of Tandem Mass Spectrometry for LISFYAGR and LISFYAGK Coupled with Respective Val-, Gln-, His-, Phe-, and Arg-Tag The tandem mass spectrometry for LISFYAGR and LISFYAGK coupled with respective Val-, Gln-, His-, Phe-, and Arg-tag was conducted, wherein peptide labeled with $^L$MBIT and peptide labeled with $^H$MBIT were mixed at the ratio of 1:1 to conduct the experiment. The results thereof were shown in FIGS. 18 to 21.

FIG. 18 shows the tandem mass spectra obtained by selecting +2 charged parent ion formed from coupling peptide LISFYAGR having one amine on N-terminal with the labeling agent in quadrupole ion trap and then conducting resonant excitation collision-induced dissociation. Since the labeling agents were coupled only with N-terminal of peptides, all of y-type fragment ions were detected at a certain mass-to-charge ratio (m/z) regardless of the kinds of labeling agents. On the other hand, b-type fragment ions were detected with increasing the mass-to-charge ratio (m/z) depending on the kinds of labeling agents.

Respective $^L y_S$ and $^H y_S$ ions that can be utilized as the quantitation signals were detected at m/z 997 Th and 1000 Th with having +1 charge. In case of His- and Arg-tag having strong basicity, $y_S$ ions were strongly detected. It could be seen that in case of Val-, Gln-, and Phe-tag, $y_S$ quantitation signal ions were detected with weak intensity of the signals.

FIG. 19 showed the tandem mass spectra obtained by selecting +1 charged parent ion formed from coupling peptide LISFYAGR having one amine on N-terminal with the labeling agent in quadrupole ion trap, and then conducting resonant excitation collision-induced dissociation. In this case, it could be seen that although the quantitation signal ions could be detected, they were measured with very low intensity, and thus, unsuitable for use in the quantitative analysis.

FIG. 20 showed the tandem mass spectra obtained by selecting +2 charged parent ion formed from coupling peptide LISFYAGK having one amine on each of N-terminal and lysine side chain for a total of two amines, with the labeling agent in quadrupole ion trap, and then conducting resonant excitation collision-induced dissociation. As can be seen from FIG. 20, it could also be identified that since the labeling agents were coupled with amine of N-terminal and amine of C-terminal lysine, respectively, all of b-type and y-type fragment ions were detected with increasing by a certain mass-to-charge ratio depending on the kinds of labeling agents. Particularly, it could be known that +1 charged $y_S$ ions were measured at a mass-to-charge ratio higher than –tag, and detected in the range absolutely not affected by other sequence ions. In addition, the signal intensity was strong as much as other sequence ions, and the intensity ratio of $[^L y_S]$:$[^H y_S]$ ions coincident with the mixing ratio of 1:1 was observed.

For Val- and Phe-tag, +2 charged $y_S$ ions were also detected and displayed the ion intensity ratio complying with the mixing ratio of 1:1. On the other hand, for Gln-tag with strong basicity and His- and Arg-tag with strong basicity, +2 charged $y_S$ ions were substantially not detected. Instead, 1+ charged $y_S$ ions were strongly detected. Since +2 charged $y_S$ ions can be disturbed by other +1 charged sequence ions, it is often considered advantageous to use +1 charged $y_S$ ions as a signal for the quantitative analysis.

FIG. 21 showed the tandem mass spectra obtained by selecting +1 charge parent ion formed from coupling peptide LISFYAGK having one amine on each of N-terminal and lysine side chain for a total of two amines, with the labeling agent in quadrupole ion trap, and then conducting resonant excitation collision-induced dissociation. Similarly to the case where +2 charged parent ions were experimented, it could be identified that all of b-type and y-type fragment ions were detected with increasing by a certain mass-to-charge ratio depending on the kinds of labeling agents. However, in the result of experiment using +1 charged parent ions, it could be distinctively identified that +1 charged $y_S$ quantitation signals were very strongly displayed. In addition, it could be seen that the signal intensity ratio of $[^L y_S]$:$[^H y_S]$ ions was also detected almost in agreement with the mixing ratio of 1:1.

3) Measurement of the Intensity of $y_S$ Quantitation Signals

Figure 22:
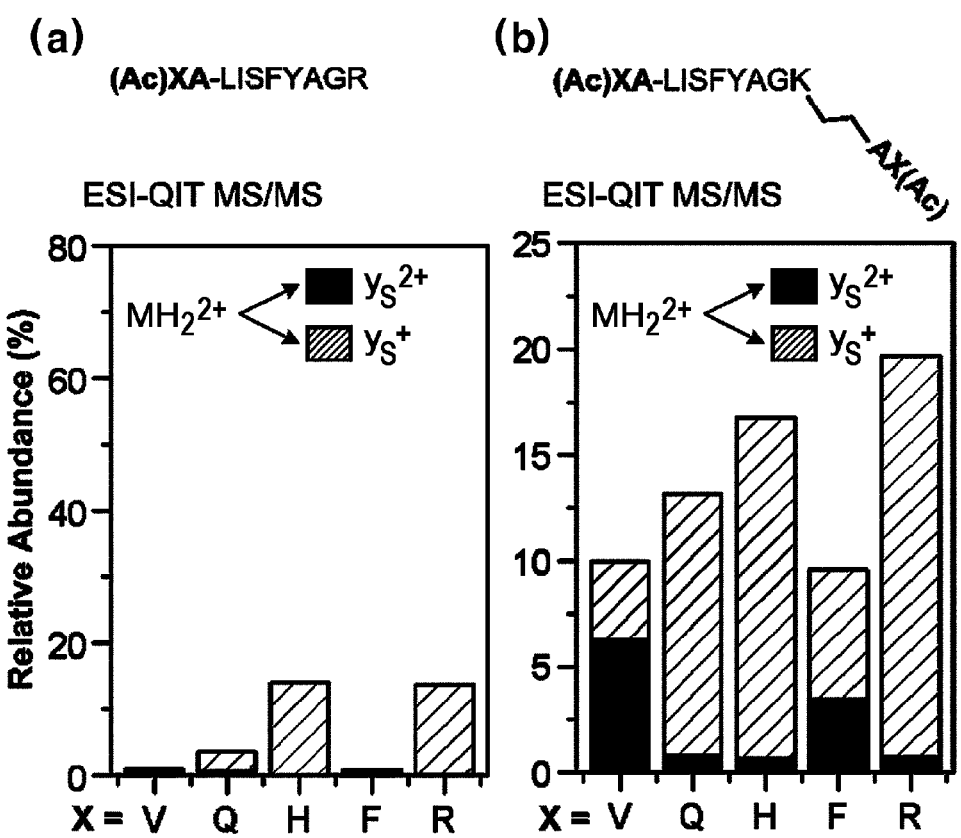
FIG. 22 shows the ratio of the intensity of $y_S$ quantitation signals displayed when parent ion ($MH_2^{2+}$) having +2 charge of the model peptides LISFYAGR (FIG. 22(a)) and LISFYAGK (FIG. 22(b)) labeled with the labeling agent according to one example of the present invention is subjected to tandem mass spectrometry in quadrupole ion trap, to the sum of signal intensities of total fragment ions.
Figure 23:
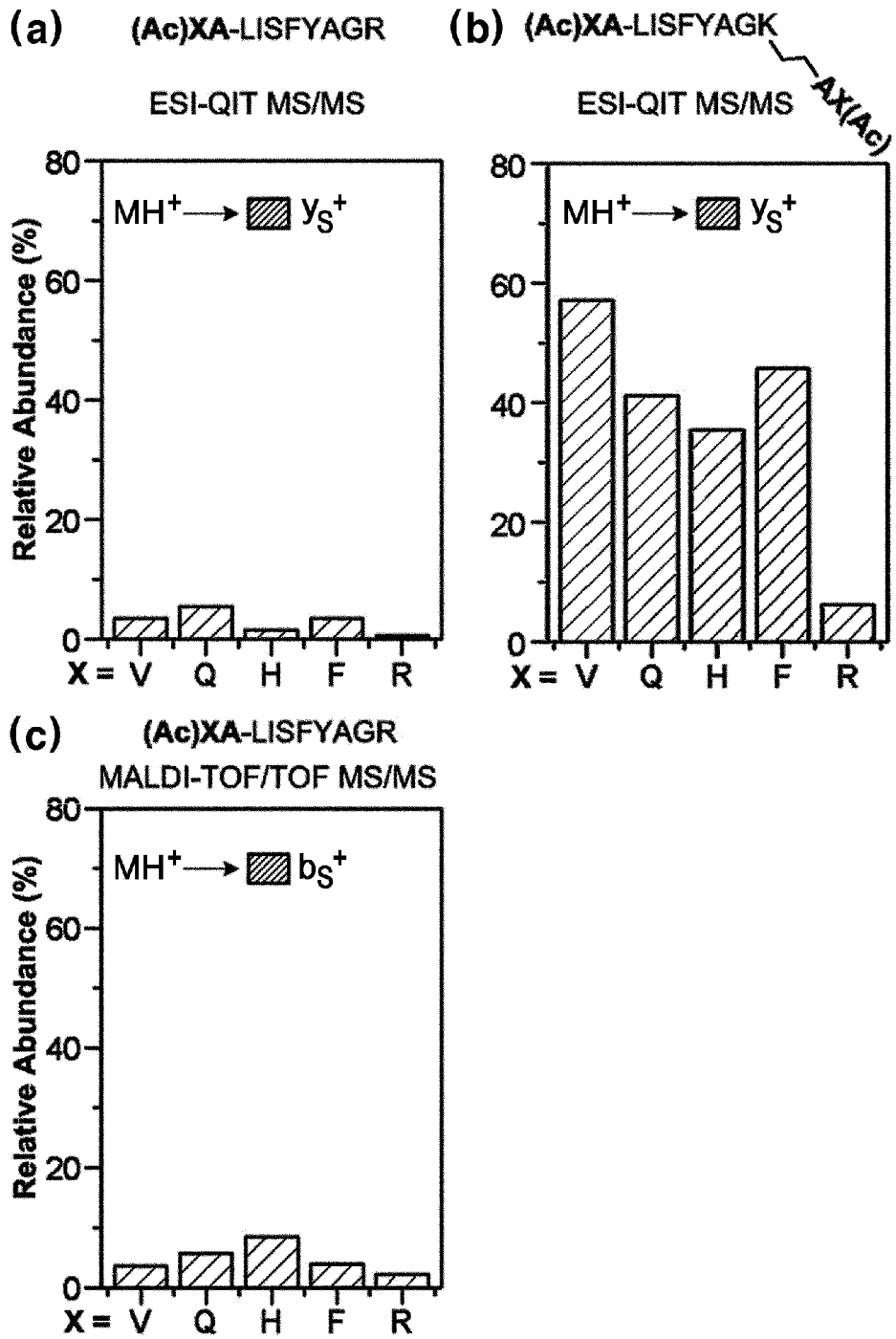
FIG. 23 shows the ratio of the intensity of $y_S$ quantitation signals displayed when parent ion ($MH^+$) having +1 charge of the model peptides LISFYAGR (FIG. 23(a)) and LISFYAGK (FIG. 23(b)) labeled with the labeling agent according to one example of the present invention is subjected to tandem mass spectrometry in quadrupole ion trap, to the sum of signal intensities of total fragment ions.

FIG. 22 and FIG. 23 are the drawings showing the ratio of the intensity of $y_S$ quantitation signals displayed when the model peptides labeled with the labeling agent were subjected to tandem mass spectrometry, to the sum of signal intensities of total fragment ions. FIG. 22 depicted the result obtained by selecting and decomposing +2 charged parent ions after labeling with the labeling agent and then electrospray ionizing. It could be identified that as compared to LISFYAGR coupled with one labeling agent, LISFYAGK coupled with two labeling agents on N-terminal and C-terminal displayed an intensity that was at least two times stronger than that of the quantitation signals $y_S$.

FIGS. 23(a) and 23(b) showed the results obtained by respectively selecting and decomposing +1 charged LISFYAGR and LISFYAGK ions after labeling with the labeling agent and then electrospray ionizing. In comparison with the case in which the existing $b_S$ ions were utilized, FIG. 23(c) depicts the ratio of $b_S$ quantitation signal ions when +1 charged LISFYAGR parent ion labeled with the labeling agent was detected by MALDI-TOF/TOF apparatus. LISFYAGK coupled with two labeling agents was not detected by the MALDI ionization method. Accordingly, it could be identified that the relative quantitation signal intensity of $y_S$ ions produced by decomposing LISFYAGK coupled with two labeling agents on N-terminal amine and C-terminal lysine amine, respectively, was at least 5 times stronger than that obtained by using the existing $b_S$ ions.

On the basis of the results above, it could be seen that when a total of two or more labeling agents were coupled by coupling the labeling agents with lysine side chain in addition to N-terminal, very strong $y_S$ quantitation signals could be obtained. Further, it could also be seen that when two labeling agents were coupled with N-terminal amine and C-terminal lysine, +1 charged $y_S$ ions could be detected with very strong signal intensity at the mass-to-charge ratio absolutely not disturbed by other sequence ions, so that the quantitative analysis can be very accurately and reproducibly accomplished without disturbance by noise signals. The use of $y_S$ having a high mass value can permit the quantitative analysis with maximally 5 times or more strong intensity of signals as compared to the use of the existing quantitation signal ions having a small mass value.

Figure 24:
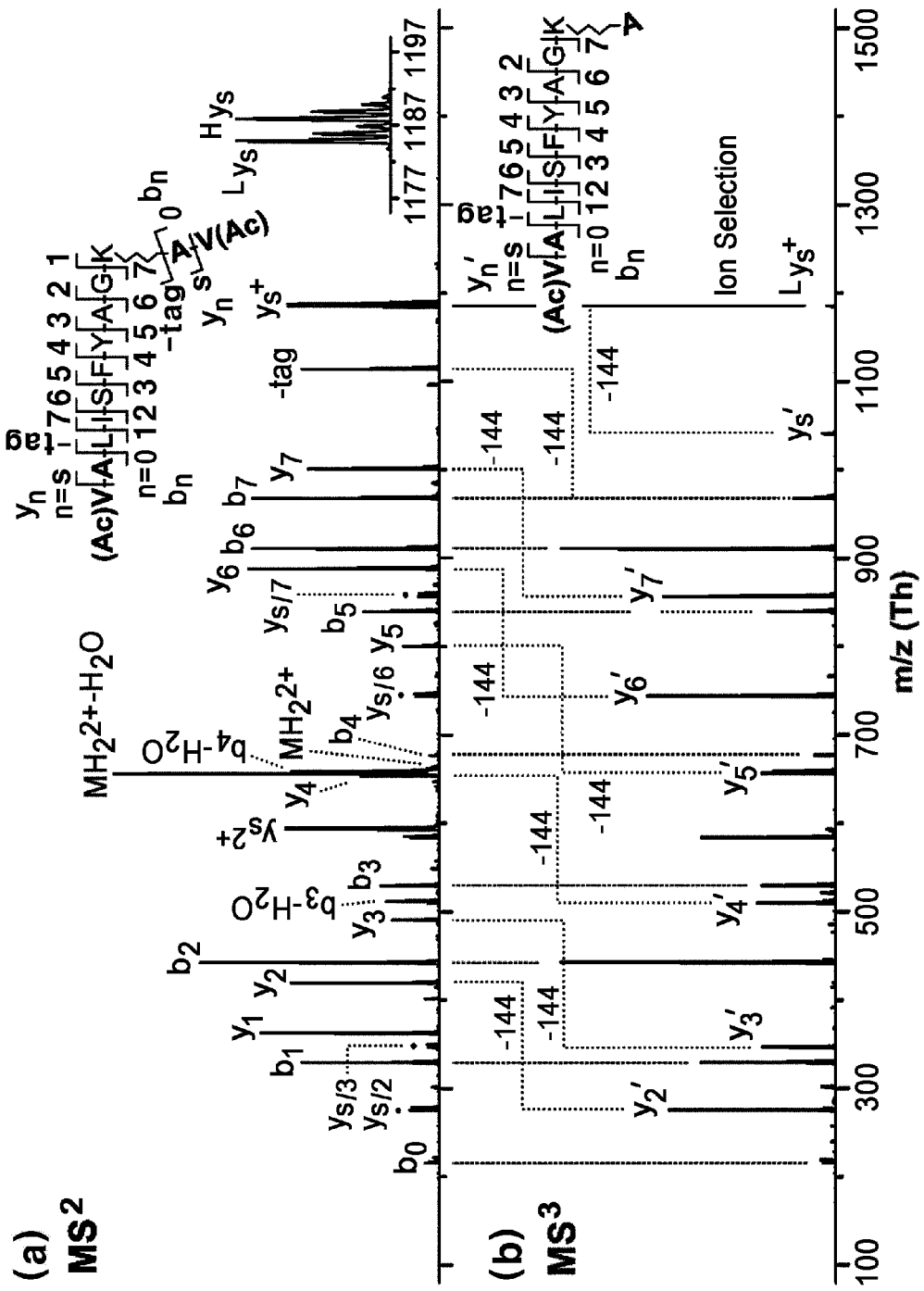
FIG. 24(a) shows the $MS^2$ tandem mass spectrum obtained by selecting ions ($MH_2^{2+}$) having +2 charge among parent ions formed from coupling peptide LISFYAGK having one amine on each of N-terminal and lysine side chain for a total of two amines, with Val-tag in quadrupole ion trap, and then conducting resonant excitation collision-induced dissociation.
FIG. 24(b) shows the $MS^3$ tandem mass spectrum obtained by selecting again $^L y_S$ ions produced in $MS^2$ tandem mass spectrometry in ion trap, and then conducting again collision-induced dissociation.

4) Analysis of $MS^3$ Tandem Mass Spectrum Obtained by Again Selecting $y_S$ Ions in Ion Trap and then Subjecting them to Collision-Induced Dissociation FIG. 24 showed the $MS^3$ tandem mass spectrum obtained by selecting again +1 charged $y_S$ ions, which are produced from selection of ions having +2 charge among parent ions formed from coupling peptide LISFYAGK having one amine on each of N-terminal and lysine side chain for a total of two amines with the labeling agents in quadrupole ion trap, and then resonant excitation collision-induced dissociation, in ion trap followed by collision-induced dissociation again.

The result obtained from the experiment conducted by selecting $^L y_S$ ions of LISFYAGK coupled with Val-tag was depicted. If the labeling agent on N-terminal was decomposed to produce $y_S$ ions, in $MS^3$ spectrum all of $b_n$ ions should be displayed with decreasing 144 Th. On the other hand, if $y_S$ ions were produced from the labeling agent coupled with lysine side chain, in $MS^3$ spectrum all of $y_n$ ions should be displayed with decreasing 144 Th. In $MS^3$ spectrum, $b_n$ and $y_n$ fragment ions displayed in the position decreased by 144 Th were designated as $b_n'$ and $y_n'$, respectively. As can be seen from FIG. 24(b), it could be identified that all of the positions displaying b-type fragment ions comprising N-terminal were identically maintained, but all of the positions displaying y-type fragment ions comprising C-terminal were detected as $y_n'$ and decreasing by 144 Th. $b_n$'s were substantially not detected. As a result, it could be identified that $y_S$ quantitation signals strongly displayed in tandem mass spectrometry were originated from the labeling agent coupled with amine group of lysine side chain rather than the labeling agent attached to N-terminal of peptide.

In consideration of the results shown in said FIG. 18 to FIG. 24, it could be determined that the quantitative analysis using $y_S$ shows the best efficiency when peptides that comprise lysine so that they can be coupled with two or more labeling agents are used as the analyte. Particularly, peptides having lysine on C-terminal have the great advantage that +1 charged $y_S$ ions can be detected without any disturbance by other fragment ions.

5) Standard Quantitative Analysis Curve

Figure 25:
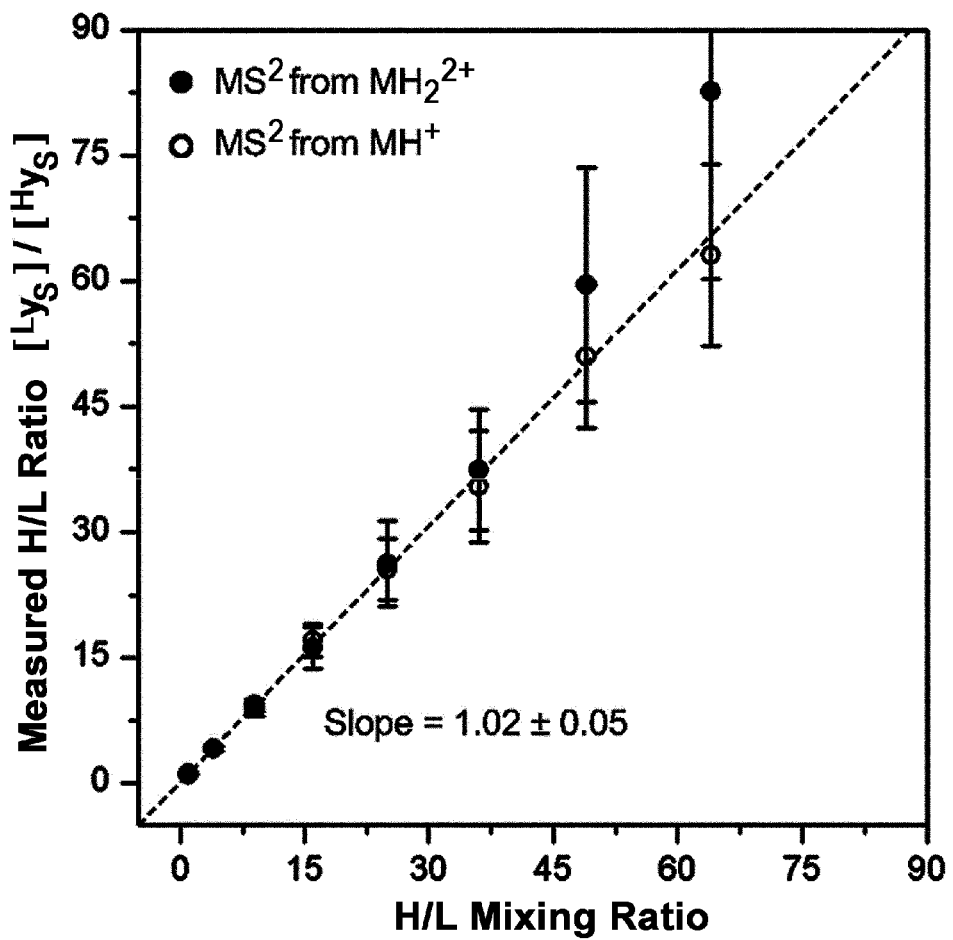
FIG. 25 shows the standard quantitative analysis curve obtained by subjecting the model peptide LISFYAGK mixed with Gln-tag discriminately labeled with $^H$MBIT and $^L$MBIT, at various ratios, to tandem mass spectrometry, and then conducting the quantitative analysis using the signal intensity ratio of resulting $^L y_S$ and $^H y_S$ ions.

FIG. 25 is a drawing showing the standard quantitative analysis curve obtained by subjecting the model peptides discriminately labeled with $^H$MBIT and $^L$MBIT and then mixed at various ratios, to tandem mass spectrometry, and then conducting the quantitative analysis using the intensity of resulting $^L y_S$ and $^H y_S$ ions. The labeling agent used in this experiment was Gln-tag. LISFYAGK was utilized as the model peptide. The experiment was conducted for each of +1 or +2 charged peptide ions to obtain the result. The concentration of peptide solutions labeled with the labeling agent was maintained at about 5 μM, regardless of the mixing ratio of peptides. As shown in FIG. 25, it could be known that the quantitative analysis using $y_S$ ions showing strong signal intensity provides the measured values well fitted with the actual mixing ratio. Particularly, it could be seen that when +1 charged parent ions were selected, the signal intensity of $y_S$ was specifically strongly displayed as described above, and therefore, the result of quantitative analysis could be obtained even at the mixing ratio up to 1:64. When +2 charged parent ions were selected for the quantitative analysis, a very good linearity was displayed at the mixing ratio up to 1:36. In consideration of the fact that when the existing $b_S$ quantitation signals having small mass were used, the limit of quantitation was about the mixing ratio of 1:16. By introducing $y_S$ the limit of quantitation was improved up to about 4 times.

6) Result of Tandem Mass Analysis for YGGFLK and LISFYAGK Coupled with Ethyl-Tag In case where methyl is utilized as the isotope encoding group $R_A$ and $R_C$, a difference in masses of quantitation signal ions is 3 Da and therefore there is a possibility of interference with $^H y_S$ quantitation signal ions by the natural isotope pattern of $^L y_S$ quantitation signal ions. Such problem can be overcome by using ethyl group as the isotope encoding group $R_A$ and $R_C$ to sufficiently increase a difference in masses of quantitation signal ions to 5 Da. For this, the model peptides were coupled with Ethyl-tag to conduct tandem mass spectrometry.

Figure 26:
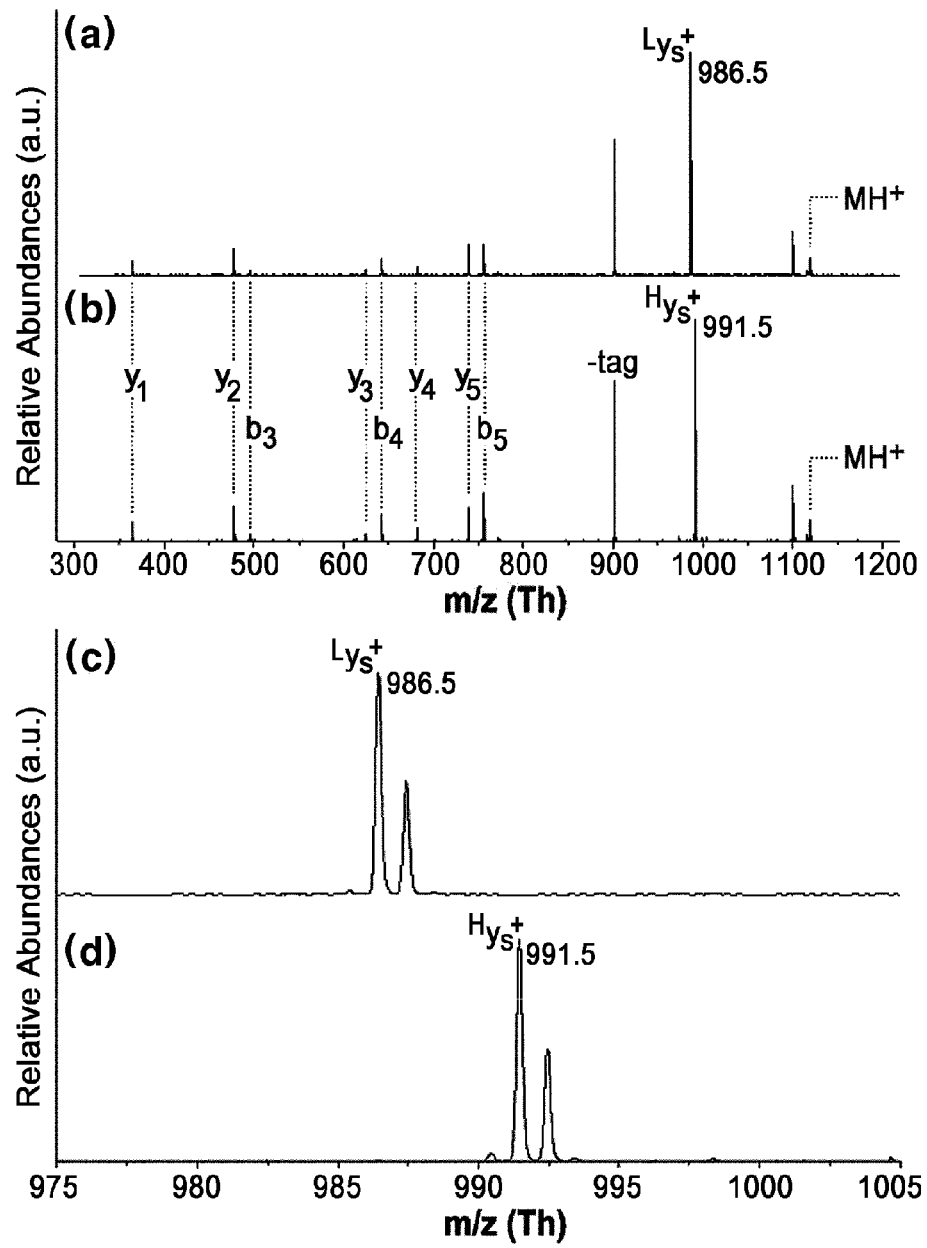
FIGS. 26(a) and 26(b) show the MS$^2$ tandem mass spectra obtained by selecting ions (MH$^+$) having +1 charge among parent ions formed from coupling peptide YGGFLK having one amine on each of N-terminal and lysine side chain for a total of two amines, with Ethyl-tag labeled with $^H$MBIT (FIG. 26(a)) or $^L$MBIT (FIG. 26(b)) in quadrupole ion trap, and then conducting resonant excitation collision-induced dissociation.
FIGS. 26(c) and 26(d) are the expanded drawings showing the range in which $y_S$ quantitation signal ions are produced in FIGS. 26(a) and 26(b).
Figure 27:
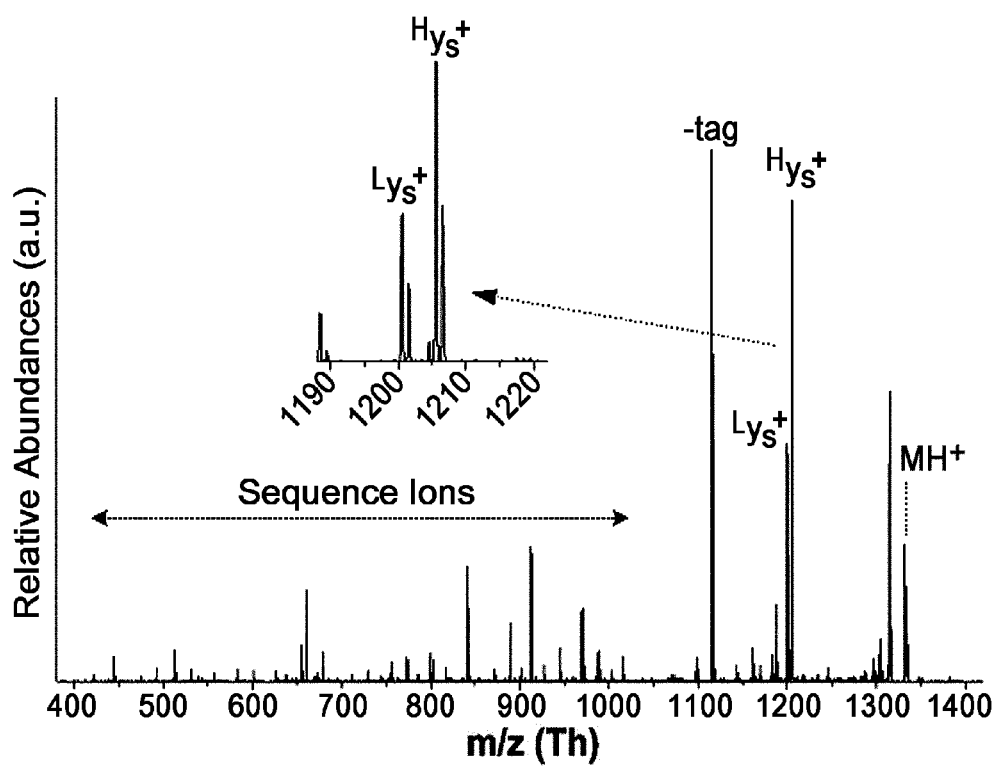
FIG. 27 shows the MS$^2$ tandem mass spectrum obtained by selecting ions having +1 charge among parent ions formed from coupling peptide LISFYAGK having one amine on each of N-terminal and lysine side chain for a total of two amines, with Ethyl-tag in quadrupole ion trap, and then conducting resonant excitation collision-induced dissociation, wherein peptide coupled with $^L$MBIT of Ethyl-tag and peptide coupled with $^H$MBIT of Ethyl-tag are mixed at the ratio of 2:1, and then subjected to tandem mass spectrometry.

The results of tandem mass analysis for YGGFLK coupled with Ethyl-tag were depicted in FIGS. 26 and 27. The result of tandem mass analysis for LISFYAGK coupled with Ethyl-tag was depicted in FIG. 28.

FIG. 26 showed the tandem mass spectra obtained by selecting +1 charged parent ion formed from coupling peptide YGGFLK having one amine on both the N-terminal and lysine side chain for a total of two amines, with Ethyl-tag labeled in quadrupole ion trap, and then conducting resonant excitation collision-induced dissociation. Among them, FIGS. 26(a) and 26(b) show the result of using Ethyl-tag labeled with $^H$MBIT or $^L$MBIT, respectively. In case where Ethyl-tag was labeled with $^H$MBIT, +1 charged $^L y_S$ ions were detected at the mass-to-charge ratio of 986.5 and in case labeled with $^L$MBIT, $^H y_S$ ions were detected at 991.5. FIGS. 26(c) and 26(d) are the expanded drawings showing the domain in which $y_S$ ions are detected, wherein it could be identified that $^L y_S$ and $^H y_S$ ions were not interfered each other due to a difference in masses of 5 Da.

FIG. 27 showed the tandem mass spectrum for the mixture comprising peptide having the sequence of LISFYAGK coupled with $^L$MBIT of Ethyl-tag and peptide coupled with $^H$MBIT of Ethyl-tag at the mixing ratio of 2:1. As the result of tandem mass analysis for +1 charged parent ions detected at the mass-to-charge ratio of 1332.6, +1 charged $^L y_S$ and $^H y_S$ ions were detected at the mass-to-charge ratios of 1200.6 and 1205.6 with the ratio of $[^H y_S]:[^L y_S]=2:1$ to successfully reproduce the mixing ratio of $^L$MBIT and $^H$MBIT.

7) Result of Quantitative Analysis of Mixed Protein Sample Using Gln-Tag

To practice the quantitative analysis of practical proteins using $y_S$ ions of MBIT, two kinds of the mixed protein samples (mixed samples A and B) comprising three kinds of proteins at the mixing ratios different from each other were prepared and then analyzed using Gln-tag. The samples were prepared in the manner that the quantities of bovine serum albumin, myoglobin, and ubiquitin in the mixed sample A were 2 times, four times and 0.5 times the quantities of bovine serum albumin, myoglobin, and ubiquitin in the mixed sample B, respectively. The mixed samples were enzymatically decomposed with trypsin, labeled with $^L$MBIT and $^H$MBIT of Gln-tag, and then quantitatively analyzed by liquid chromatography and tandem mass spectrometry. The result thereof was shown in FIG. 28.

Figure 28:
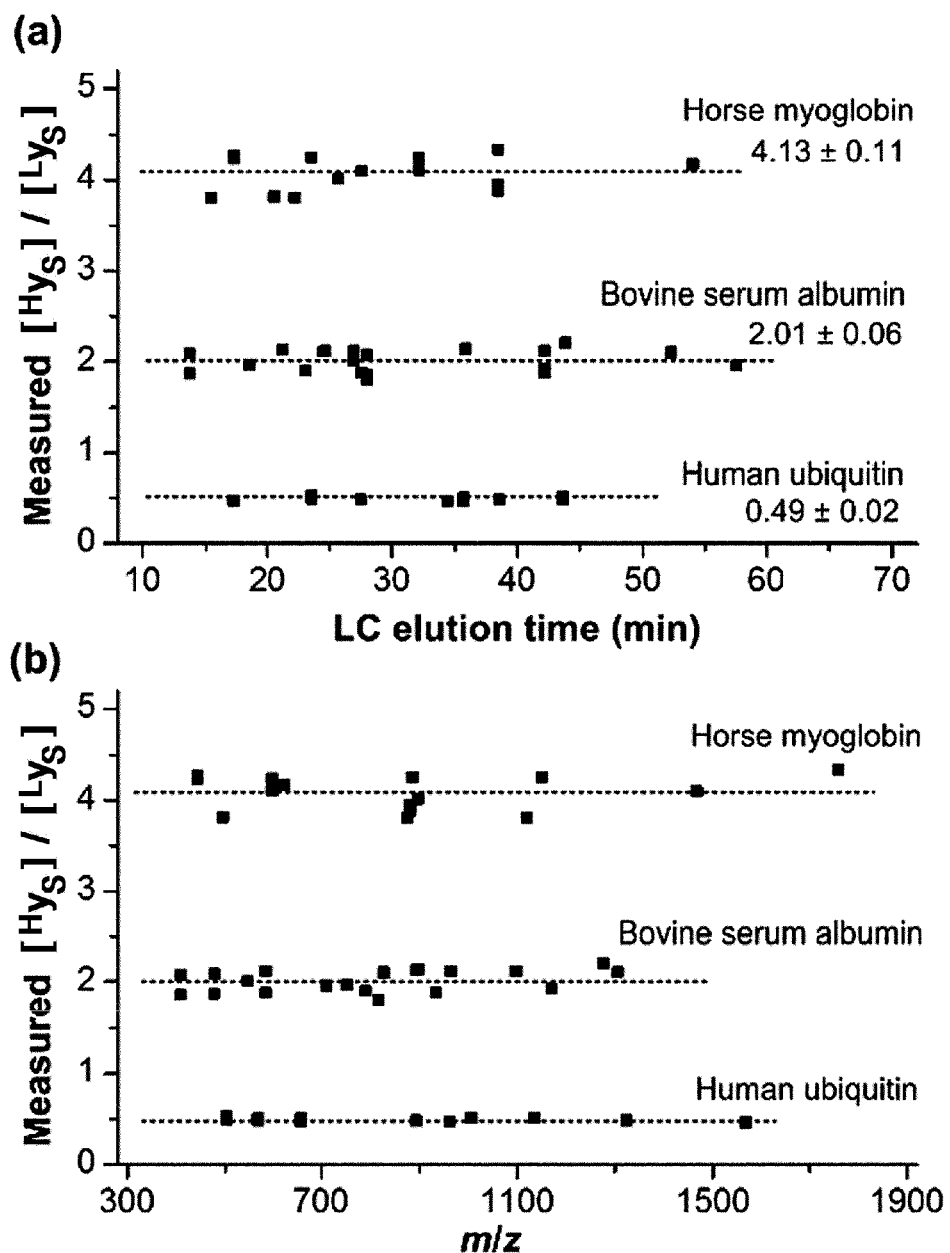
FIG. 28(a) is a drawing showing [$^H y_S$]:[$^L y_S$] ratio measured over the elution time of the detected peptides in liquid chromatography.
FIG. 28(b) is a drawing showing [$^H y_S$]:[$^L y_S$] ratio over the mass-to-charge ratio of detected peptides.

FIG. 28(*a*) is a drawing showing [$^H y_S$]:[$^L y_S$] ratio measured over the elution time of the detected peptides in liquid chromatography. FIG. 28(*b*) is a drawing showing [$^H y_S$]:[$^L y_S$] ratio over the mass-to-charge ratio of detected peptides. Peptide identified as being originated from bovine serum protein provided the result of [$^H y_S$]:[$^L y_S$]=2.01±0.06, myoglobin provided the result of [$^H y_S$]:[$^L y_S$]=4.13±0.11, and ubiquitin provided the result of [$^H y_S$]:[$^L y_S$]=0.49±0.02. This is the case where the quantitative analysis was successfully accomplished with the ratio of respective proteins in the mixed samples A and B within the error range of 5%.

The invention claimed is:

1. A compound represented by the following chemical formula 1:

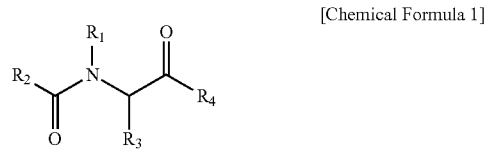

[Chemical Formula 1]

wherein, $R_1$ is $C_{1-10}$

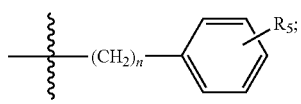

alkyl or $R_1$ is $C_{1-10}$

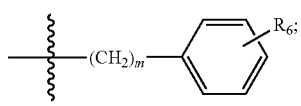

alkyl or $R_3$ is a side chain of an amino acid residue;

$R_4$ is hydroxy or a reactive linker;

$R_5$ is hydrogen, $C_{1-4}$ alkyl or $C_{2-4}$ alkynyl;

$R_6$ is hydrogen, $C_{1-4}$ alkyl or $C_{2-4}$ alkynyl;

n and m are independently of each other an integer of 1 to 4; and wherein said $R_1$ and $R_2$ can comprise deuterium.

2. The compound according to claim 1, characterized in that $R_1$ is $C_{6-9}$ alkyl or

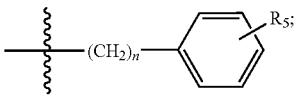

$R_2$ is $C_{6-9}$ alkyl or

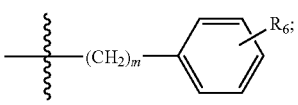

$R_5$ is hydrogen, propyl or prop-1-ynyl;
$R_6$ is hydrogen, propyl or prop-1-ynyl); and
n and m are independently of each other an integer of 1 to 4.

3. The compound according to claim 2, characterized in that $R_1$ is octyl; and $R_2$ is heptyl.

4. The compound according to claim 1, characterized in that $R_1$ is $C_{1-10}$ alkyl and $R_2$ is $C_{1-10}$ alkyl; or $R_1$ is

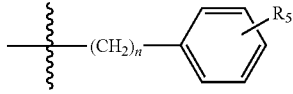

and $R_2$ is

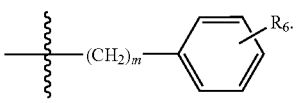

5. The compound according to claim 1, characterized in that $R_1$ and $R_2$ are
CH$_3$C≡CC$_6$H$_4$CH$_2$ and CD$_3$C≡CC$_6$H$_4$CD$_2$CH$_2$, respectively;
CH$_3$C≡CC$_6$H$_4$CD$_2$ and CD$_3$C≡CC$_6$H$_4$CH$_2$CH$_2$, respectively;
CD$_3$C≡CC$_6$H$_4$CH$_2$ and CH$_3$C≡CC$_6$H$_4$CD$_2$CH$_2$, respectively; or
CD$_3$C≡CC$_6$H$_4$CD$_2$ and CH$_3$C≡CC$_6$H$_4$CH$_2$CH$_2$, respectively.

6. The compound according to claim 1, characterized in that $R_3$ is a side chain of any one amino acid residue selected from the group consisting of glycine, alanine, serine, valine, leucine, isoleucine, methionine, glutamine, asparagine, cysteine, histidine, phenylalanine, arginine, tyrosine and tryptophan.

7. The compound according to claim 1, characterized in that $R_4$ is hydroxy, succinimid-N-oxy, 3-sulfosuccinimid-N-oxy, benzotriazol-1-yl-oxy, pentahalobenzyloxy, 4-nitrophenoxy or 2-nitrophenoxy.

8. The compound according to claim 1, characterized in that said compound is any one selected from the group consisting of:

1) 2-(N-(4-(prop-1-ynyl)benzyl)-3-(4-(prop-1-ynyl)phenyl)-propanamido)acetic acid;
2) 2-(N-(4-(prop-1-ynyl)benzyl)-3-(4-(prop-1-ynyl-3,3,3-$d_3$)-phenyl)propanamido-3,3-$d_2$)acetic acid;
3) 2-(N-(4-(prop-1-ynyl)benzyl-1,1-$d_2$)-3-(4-(prop-1-ynyl-3,3,3-$d_3$)phenyl)propanamido)acetic acid;
4) 2-(N-(4-(prop-1-ynyl-3,3,3-$d_3$)benzyl)-3-(4-(prop-1-ynyl)phenyl)propanamido-3,3-$d_2$)acetic acid;
5) 2-(N-(4-(prop-1-ynyl-3,3,3-$d_3$)benzyl-1,1-$d_2$)-3-(4-(prop-1-ynyl)phenyl)propanamido)acetic acid;
6) 2-(N-(4-propylbenzyl)-2-(4-propylphenyl)acetamido)acetic acid;
7) 2-(5-phenyl-N-(3-phenylpropyl)pentanamido)acetic acid; and
8) 2-(N-octyloctanamido)acetic acid.

9. A composition comprising two or more compounds according to claim 1.

10. The composition according to claim 9, characterized in that said two compounds have the same number of deuterium atoms.

11. The composition according to claim 9, characterized in that said composition comprises any one compound selected from the group consisting of:
1) 2-(N-(4-(prop-1-ynyl)benzyl)-3-(4-(prop-1-ynyl-3,3,3-$d_3$)-phenyl)propanamido-3,3-$d_2$)acetic acid;
2) 2-(N-(4-(prop-1-ynyl)benzyl-1,1-$d_2$)-3-(4-(prop-1-ynyl-3,3,3-$d_3$)phenyl)propanamido)acetic acid;
3) 2-(N-(4-(prop-1-ynyl-3,3,3-$d_3$)benzyl)-3-(4-(prop-1-ynyl)phenyl)propanamido-3,3-$d_2$)acetic acid; and
4) 2-(N-(4-(prop-1-ynyl-3,3,3-$d_3$)benzyl-1,1-$d_2$)-3-(4-(prop-1-ynyl)phenyl)propanamido)acetic acid.

* * * * *

UNITED STATES PATENT AND TRADEMARK OFFICE
CERTIFICATE OF CORRECTION

PATENT NO. : 8,809,012 B2
APPLICATION NO. : 13/818489
DATED : August 19, 2014
INVENTOR(S) : Seung Koo Shin et al.

It is certified that error appears in the above-identified patent and that said Letters Patent is hereby corrected as shown below:

On the Title Page

Left column, item (73), replace "Postach Academy-Industry" with --Postech Academy-Industry--.

Signed and Sealed this
Twenty-third Day of December, 2014

Michelle K. Lee
*Deputy Director of the United States Patent and Trademark Office*